(12) United States Patent
Housey

(10) Patent No.: US 10,471,065 B2
(45) Date of Patent: Nov. 12, 2019

(54) THERAMUTEIN MODULATORS

(71) Applicant: HMI Medical Innovations, LLC, Southfield, MI (US)

(72) Inventor: Gerard M. Housey, Southfield, MI (US)

(73) Assignee: HMI Medical Innovations, LLC, Southfield, MI (US)

( * ) Notice: Subject to any disclaimer, the term of this patent is extended or adjusted under 35 U.S.C. 154(b) by 0 days.

(21) Appl. No.: 15/789,476

(22) Filed: Oct. 20, 2017

(65) Prior Publication Data
US 2018/0042935 A1  Feb. 15, 2018

Related U.S. Application Data

(60) Division of application No. 15/399,543, filed on Jan. 5, 2017, now Pat. No. 9,795,610, which is a division
(Continued)

(51) Int. Cl.
| | | |
|---|---|---|
| *C07D 213/81* | (2006.01) | |
| *A61K 31/5377* | (2006.01) | |
| *C07D 213/87* | (2006.01) | |
| *C07D 215/50* | (2006.01) | |
| *C07D 231/14* | (2006.01) | |
| *C07D 239/42* | (2006.01) | |
| *C07D 239/48* | (2006.01) | |
| *C07D 239/84* | (2006.01) | |
| *C07D 253/065* | (2006.01) | |
| *C07D 401/12* | (2006.01) | |
| *C07D 405/12* | (2006.01) | |
| *C07D 409/12* | (2006.01) | |
| *G01N 33/574* | (2006.01) | |
| *C07C 243/38* | (2006.01) | |
| *C07D 213/77* | (2006.01) | |
| *C07D 213/86* | (2006.01) | |
| *C07D 215/38* | (2006.01) | |
| *C07D 253/075* | (2006.01) | |
| *C07D 403/12* | (2006.01) | |
| *G01N 33/573* | (2006.01) | |
| *A61K 31/47* | (2006.01) | |
| *A61K 31/4709* | (2006.01) | |
| *A61K 31/505* | (2006.01) | |
| *A61K 31/506* | (2006.01) | |
| *A61K 31/53* | (2006.01) | |
| *G01N 33/50* | (2006.01) | |
| *A61K 31/166* | (2006.01) | |

(Continued)

(52) U.S. Cl.
CPC ........ *A61K 31/5377* (2013.01); *A61K 31/166* (2013.01); *A61K 31/175* (2013.01); *A61K 31/195* (2013.01); *A61K 31/27* (2013.01); *A61K 31/415* (2013.01); *A61K 31/4196* (2013.01); *A61K 31/44* (2013.01); *A61K 31/444* (2013.01); *A61K 31/4436* (2013.01); *A61K 31/47* (2013.01); *A61K 31/4709* (2013.01); *A61K 31/495* (2013.01); *A61K 31/505* (2013.01); *A61K 31/506* (2013.01); *A61K 31/517* (2013.01); *A61K 31/53* (2013.01); *C07C 243/38* (2013.01); *C07D 213/77* (2013.01); *C07D 213/81* (2013.01); *C07D 213/86* (2013.01); *C07D 213/87* (2013.01); *C07D 215/38* (2013.01); *C07D 215/50* (2013.01); *C07D 231/14* (2013.01); *C07D 239/42* (2013.01); *C07D 239/48* (2013.01); *C07D 239/84* (2013.01); *C07D 253/065* (2013.01); *C07D 253/075* (2013.01); *C07D 401/12* (2013.01); *C07D 403/12* (2013.01); *C07D 405/12* (2013.01); *C07D 409/12* (2013.01); *G01N 33/502* (2013.01); *G01N 33/5011* (2013.01); *G01N 33/5041* (2013.01); *G01N 33/573* (2013.01); *G01N 33/574* (2013.01); *G01N 2500/00* (2013.01); *G01N 2500/10* (2013.01)

(58) Field of Classification Search
CPC .................................................. A61K 31/5377
See application file for complete search history.

(56) References Cited

U.S. PATENT DOCUMENTS

| | | |
|---|---|---|
| 3,647,858 A | 3/1972 | Hinkley et al. |
| 3,887,699 A | 6/1975 | Yolles |

(Continued)

FOREIGN PATENT DOCUMENTS

| | | |
|---|---|---|
| CA | 1176565 | 10/1984 |
| EP | 0058481 A1 | 8/1982 |

(Continued)

OTHER PUBLICATIONS

Akiyama, S., Yoshimura, A., Kikuchi, H., Sumizawa, T., Kuwano, M., Tahara, Y. (1989) Synthetic isoprenoid photoaffinity labeling of P glycoprotein specific to multidrug resistant cells. Mol. Pharmacol. Nov.;36:730 735.

(Continued)

*Primary Examiner* — Paul V Ward
(74) *Attorney, Agent, or Firm* — Mueting, Raasch & Gebhardt, P.A.

(57) ABSTRACT

This invention relates to agents that are inhibitors or activators of variant forms of endogenous proteins and novel methods of identifying such variants. Of particular interest are inhibitors and activators of endogenous protein variants, encoded by genes which have mutated, which variants often arise or are at least first identified as having arisen following exposure to a chemical agent which is known to be an inhibitor or activator of the corresponding unmutated endogenous protein.

16 Claims, 13 Drawing Sheets

Related U.S. Application Data of application No. 14/297,863, filed on Jun. 6, 2014, now Pat. No. 9,579,326, which is a continuation of application No. 13/758,422, filed on Feb. 4, 2013, now abandoned, which is a continuation of application No. 10/569,315, filed as application No. PCT/US2005/018412 on May 23, 2005, now Pat. No. 8,367,038.

(60) Provisional application No. 60/633,013, filed on Dec. 3, 2004, provisional application No. 60/573,962, filed on May 23, 2004.

(51) Int. Cl.
| | |
|---|---|
| A61K 31/175 | (2006.01) |
| A61K 31/195 | (2006.01) |
| A61K 31/27 | (2006.01) |
| A61K 31/415 | (2006.01) |
| A61K 31/4196 | (2006.01) |
| A61K 31/44 | (2006.01) |
| A61K 31/4436 | (2006.01) |
| A61K 31/444 | (2006.01) |
| A61K 31/495 | (2006.01) |
| A61K 31/517 | (2006.01) |

(56) References Cited

U.S. PATENT DOCUMENTS

| | | |
|---|---|---|
| 3,940,486 A | 2/1976 | Fitzi |
| 4,180,662 A | 12/1979 | Pfister et al. |
| 4,233,299 A | 11/1980 | Trummlitz et al. |
| 4,480,038 A | 10/1984 | Cheng |
| 4,500,637 A | 2/1985 | Neville et al. |
| 4,532,204 A | 7/1985 | Crespi et al. |
| 4,569,916 A | 2/1986 | Penman et al. |
| 4,695,459 A | 9/1987 | Steinman et al. |
| 4,701,406 A | 10/1987 | Chou |
| 4,714,613 A | 12/1987 | Shouval et al. |
| 4,736,866 A | 4/1988 | Leder et al. |
| 4,761,371 A | 8/1988 | Bell et al. |
| 4,857,637 A | 8/1989 | Hammonds et al. |
| 4,859,585 A | 8/1989 | Sonnenschein et al. |
| 4,859,609 A | 8/1989 | Dull et al. |
| 4,910,132 A | 3/1990 | Knight et al. |
| 4,929,616 A | 5/1990 | Binder et al. |
| 4,980,281 A | 12/1990 | Housey |
| 4,981,784 A | 1/1991 | Evans et al. |
| 4,981,790 A | 1/1991 | Haseltine |
| 4,985,352 A | 1/1991 | Julius et al. |
| 5,030,576 A | 7/1991 | Dull et al. |
| 5,057,417 A | 10/1991 | Hammonds et al. |
| 5,138,072 A | 8/1992 | Wagner |
| 5,145,842 A | 9/1992 | Driedger et al. |
| 5,260,200 A | 11/1993 | Kahn et al. |
| 5,266,464 A | 11/1993 | Housey |
| 5,380,738 A | 1/1995 | Norman et al. |
| 5,424,185 A | 6/1995 | Lam et al. |
| 5,506,107 A | 4/1996 | Cunningham et al. |
| 5,578,590 A | 11/1996 | Grunicke et al. |
| 5,665,543 A | 9/1997 | Foulkes et al. |
| 5,688,655 A | 11/1997 | Housey |
| 5,741,641 A | 4/1998 | Smart et al. |
| 5,821,072 A | 10/1998 | Schwartz et al. |
| 5,858,701 A | 1/1999 | White et al. |
| 5,877,007 A | 3/1999 | Housey |
| 6,004,931 A | 12/1999 | Cunningham et al. |
| 6,043,211 A | 3/2000 | Williams et al. |
| 6,110,737 A | 8/2000 | Escobedo et al. |
| 2003/0162222 A1 | 8/2003 | Warmuth et al. |

FOREIGN PATENT DOCUMENTS

| | | |
|---|---|---|
| EP | 0133988 A2 | 4/1985 |
| EP | 0158277 A2 | 10/1985 |
| EP | 0171496 A2 | 2/1986 |
| EP | 0214709 A2 | 4/1986 |
| EP | 0184187 A2 | 6/1986 |
| EP | 0187041 A1 | 7/1986 |
| EP | 0219106 A2 | 4/1987 |
| EP | 246 882 A2 | 11/1987 |
| EP | 0246882 A2 | 11/1987 |
| EP | 0247557 A2 | 12/1987 |
| EP | 0249390 A2 | 12/1987 |
| EP | 0251612 A2 | 1/1988 |
| EP | 325 849 B1 | 2/1988 |
| EP | 327 369 A2 | 8/1989 |
| EP | 0325849 B1 | 8/1989 |
| EP | 0327369 A2 | 8/1989 |
| EP | 0194276 B1 | 8/1993 |
| EP | 0695547 A1 | 2/1996 |
| WO | WO86/04613 | 8/1986 |
| WO | WO 88/03168 | 5/1988 |
| WO | WO 89/03687 | 5/1989 |
| WO | WO 89/07654 | 8/1989 |
| WO | WO 94/13635 | 6/1994 |
| WO | WO 94/15932 | 7/1994 |
| WO | WO 94/23714 | 10/1994 |
| WO | WO 94/26731 | 11/1994 |
| WO | WO 94/27980 | 12/1994 |
| WO | WO 02/102976 | 12/2002 |
| WO | WO 05/115992 | 5/2005 |

OTHER PUBLICATIONS

Alberts, T. (1994) Molecular Biology of the Cell, 3rd ed. (Garland Publishing, NY, USA) p. 1072.

Alberts, T. (1994) Molecular Biology of the Cell, 3rd ed. (Garland Publishing, NY, USA) pp. 1264-1265.

Angehrn, P. (1985) Antibacterial properties of carumonam (Ro 17 2301, AMA 1080), a new sulfonated monocyclic beta lactam antibiotic. Chemotherapy 31:440 450.

Armelin, H.A., Armelin, M.C., Kelly, K., Stewart, T., Leder, P., Cochran, B.H. and Stiles, C.D. (1984) Functional role for c myc in mitogenic response to platelet derived growth factor. Nature 310:655 660.

Ashendel, C.L. (1985) The phorbol ester receptor: a phospholipid regulated protein kinase. Biochim. Biophys. Acta 822:219 242.

Ashkenazi, A., Winslow, J.W., Peralta, E.G., Peterson, G.L., Schimerlik, M.I., Capon, D.J. and Ramachandran, J. (1987) An M2 muscarinic receptor subtype coupled to both adenylyl cyclase and phosphoinositide turnover. Science 238:672 675.

Balzarini, J., de Clercq, E., Ayusawa, D., Seno, T. (1985) Murine mammary FM3A carcinoma cells transformed with the herpes simplex virus type 1 thymidine kinase gene are highly sensitive to the growth-inhibitory properties of (E)-5-(2-bromovinyl)-2'-deoxyuridine and related compounds. FEBS Lett. 185:95-100.

Bardon, S., Vignon, F., Derocq, D., Rochefort, H. (1984) The antiproliferative effect of tamoxifen in breast cancer cells: mediation by the estrogen receptor. Mol. Cell. Endocrinol. 35:89 96.

Bardon, S., Vignon, F., Chalbos, D., Rochefort, H. (1985) RU486, a progestin and glucocorticoid antagonist, inhibits the growth of breast cancer cells via the progesterone receptor. J. Clin. Endocrinol. Metab. 60:692 697.

Beck, W.T., Mueller, T.J., Tanzer, L.R. (1979) Altered surface membrane glycoproteins in Vinca alkaloid resistant human leukemic lymphoblasts. Cancer Res. 39(6 Pt 1):2070 2076.

Beck, W.T., Cirtain, M.C., Look, A.T., Ashmun, R.A. (1986) Reversal of Vinca alkaloid resistance but not multiple drug resistance in human leukemic cells by verapamil. Cancer Res. 46:778 784.

Berkow, R.L., Dodson, R.W., Kraft, A.S. (1987) The effect of a protein kinase C inhibitor, H 7, on human neutrophil oxidative burst and degranulation. J. Leukoc. Biol. 41:441 446.

(56) References Cited

OTHER PUBLICATIONS

Berridge, M.J., Downes, C.P. and Hanley, M.R. (1982) Lithium amplifies agonist dependent phosphatidylinositol responses in brain and salivary glands. Biochem. J. 206:587 595.

Bollag, G.E., Roth, R.A., Beaudoin, J., Mochly Rosen, D. and Koshland, D.E. Jr. (1986) Protein kinase C directly phosphorylates the insulin receptor in vitro and reduces its protein tyrosine kinase activity. Proc. Natl. Acad. Sci. USA 83:5822 5824.

Boreiko, C., Mondal, S., Narayan, K.S. and Heidelberger, C. (1980) Effect of 12 O tetradecanoylphorbol 13 acetate on the morphology and growth of C3H/10T1/2 mouse embryo cells. Cancer Res. 40:4709 4716.

Brandt, S.J., Niedel, J.E., Bell, R.M. and Young, W.S. 3d (1987) Distinct patterns of expression of different protein kinase C mRNAs in rat tissues. Cell 49:57 63.

Brann, M.R., Buckley, N.J., Jones, S.V. and Bonner, T.I. (1987) Expression of a cloned muscarinic receptor in A9 L cells. Mol. Pharmacol. 32:450 455.

Camper, S.A., Yao, Y.A. and Rottman F.M. (1985) Hormonal regulation of the bovine prolactin promoter in rat pituitary tumor cells. J. Biol. Chem. 260:12246 12251.

Catino, J.J., Francher, D.M., Edinger, K.J. and Stringfellow, D.A. (1985) A microtitre cytotoxicity assay useful for the discovery of fermentation derived antitumor agents. Cancer Chemother. Pharmacol. 15:240 243.

Chen, C.J., Chin, J.E., Ueda, K., Clark, D.P., Pastan, I., Gottesman, M.M., Roninson, I.B. (1986) Internal duplication and homology with bacterial transport proteins in the mdr1 (P glycoprotein) gene from multidrug resistant human cells. Cell 47:381 389.

Chomczynski, P. and Sacchi, N. (1987) Single step method of RNA isolation by acid guanidinium thiocyanate phenol chloroform extraction. Anal. Biochem. 162:156 159.

Chou, C.K., Dull, T.J., Russell, D.S., Gherzi, R., Lebwohl, D., Ullrich, A. and Rosen, O.M. (1987) Human insulin receptors mutated at the ATP binding site lack protein tyrosine kinase activity and fail to mediate postreceptor effects of insulin. J. Biol. Chem. 262:1842 1847.

Ciardiello, F., Yanagihara, K., Tagliaferri, P., Bassin, R.H., Salomon D.S. (1987) Selective growth sensitivity to 4-cis-hydroxy-L-proline of rodent transformed cell lines and human tumor cell lines in vitro. Abstract 260, Proc. AACR 28:65.

Clauser, E., Ellis, L., Morgan, D., Edery, M., Roth, R.A. and Rutter, W.J. (1987) The human insulin receptor cDNA: a new tool to study the function of this receptor. J. Recept. Res. 7:377 404.

Connan, G., Rassoulzadegan, M. and Cuzin, F. (1985) Focus formation in rat fibroblasts exposed to a tumour promoter after transfer of polyoma plt and myc oncogenes. Nature 314:277 279.

Cornwell, M.M., Gottesman, M.M., Pastan, I.H. (1986) Increased vinblastine binding to membrane vesicles from multidrug resistant KB cells. J. Biol. Chem. 261:7921 7928.

Cornwell, M.M., Safa, A.R., Felsted, R.L., Gottesman, M.M., Pastan, I. (1986) Membrane vesicles from multidrug resistant human cancer cells contain a specific 150 to 170 kDa protein detected by photoaffinity labeling. Proc. Natl. Acad. Sci. USA 83:3847 3850.

Cornwell, M.M., Pastan, I., Gottesman, M.M. (1987) Certain calcium channel blockers bind specifically to multidrug resistant human KB carcinoma membrane vesicles and inhibit drug binding to P glycoprotein. J. Biol. Chem. 262:2166 2170.

Coussens, L., Parker, P.J., Rhee, L., Yang Feng, T.L., Chen, E., Waterfield, M.D., Francke, U. and Ullrich, A. (1986) Multiple, distinct forms of bovine and human protein kinase C suggest diversity in cellular signaling pathways. Science 233:859 866.

Croop, J.M., Guild, B.C., Gros, P. and Housman, D.E. (1987) Genetics of multidrug resistance: relationship of a cloned gene to the complete multidrug resistant phenotype. Cancer Res. 47:5982 5988.

Dailey, L. and Basilico, C. (1985) Sequences in the polyomavirus DNA regulatory region involved in viral DNA replication and early gene expression. J. Virol 54:739 749.

Daley, G.Q., McLaughlin, J., Witte, O.N. and Baltimore, D. (1987) The CML specific P210 bcr/abl protein, unlike v abl, does not transform NIH/3T3 fibroblasts. Science 237:532 535.

Dano K. (1973) Active outward transport of daunomycin in resistant Ehrlich ascites tumor cells. Biochim Biophys Acta. 323:466 483.

Darnell, J.E. et al. (1986) Molecular Cell Biology, Scientific American Books, Inc. p. 143.

Davis, R.J. and Czech, M.P. (1985) Platelet derived growth factor mimics phorbol diester action on epidermal growth factor receptor phosphorylation at threonine 654. Proc. Natl. Acad. Sci. USA 82:4080 4084.

Dean, M., Cleveland, J.L., Rapp, U.R. and Ihle, J.N. (1987) Role of myc in the abrogation of IL3 dependence of myeloid FDC P1 cells. Oncogene Res. 1:279 296.

Debouck, C., Gorniak, J.G., Strickler, J.E., Meek, T.D., Metcalf, B.W. and Rosenberg, M. (1987) Human immunodeficiency virus protease expressed in *Escherichia coli* exhibits autoprocessing and specific maturation of the gag precursor. Proc. Natl. Acad. Sci. USA 84:8903 8906.

De Brabander, M., Van de Veire, R., Aerts, F., Geuens, S., Hoebeke, J. (1976) A new culture model facilitating rapid quantitative testing of mitotic spindle inhibition in mammalian cells. J. Natl. Cancer. Inst. 56:357 363.

Depper, J.M., Leonard, W.J., Robb, R.J., Waldmann, T.A., Greene, W.C. (1983) Blockade of the interleukin 2 receptor by anti Tac antibody: inhibition of human lymphocyte activation. J. Immunol. 131:690 696.

DeSantis, R., Santer, U.V., Glick, M.C. (1987) NIH 3T3 cells transfected with human tumor DNA lose the transformed phenotype when treated with swainsonine. Biochem. Biophys. Res. Commun. 142:348 353.

Di Fiore, P.P., Pierce, J.H., Fleming, T.P., Hazan, R., Ullrich, A., King, C.R., Schlessinger, J. and Aaronson, S.A. (1987) Overexpression of the human EGF receptor confers an EGF dependent transformed phenotype to NIH 3T3 cells. Cell 51:1063 1070.

Di Fiore, P.P., Pierce, J.H., Kraus, M.H., Segatto, O., King, C.R., Aaronson, S.A. (1987) erbB 2 is a potent oncogene when overexpressed in NIH/3T3 cells. Science 237:178 182.

Dixon, R.A., Kobilka, B.K., Strader, D.J., Benovic, J.L., Dohlman, H.G., Frielle, T., Bolanowski, M.A., Bennett, C.D., Rands, E., Diehl, R.E., et al. (1986) Cloning of the gene and cDNA for mammalian beta adrenergic receptor and homology with rhodopsin. Nature 321(6065):75 79.

Dixon, R.A., Sigal, I.S., Candelore, M.R., Register, R.B., Scattergood, W., Rands, E., Strader, C.D. (1987) Structural features required for ligand binding to the beta adrenergic receptor. EMBO J. 6:3269 3275.

Dixon, R.A., Sigal, I.S., Rands, E., Register, R.B., Candelore, M.R., Blake, A.D. and Strader, C.D. (1987) Ligand binding to the beta adrenergic receptor involves its rhodopsin like core. Nature 326:73 77.

Dotto, G.P., Parada, L.F. and Weinberg, R.A. (1985) Specific growth response of ras transformed embryo fibroblasts to tumour promoters. Nature 318:472 475.

Drebin, J.A., Link, V.C., Stern, D.F., Weinberg, R.A. and Greene, M.I. (1985) Down modulation of an oncogene protein product and reversion of the transformed phenotype by monoclonal antibodies. Cell 41:695 706.

Druege, P.M., Klein Hitpass, L., Green, S., Stack, G., Chambon, P. and Ryffel, G.U. (1986) Introduction of estrogen responsiveness into mammalian cell lines. Nucleic Acids Res. 14:9329 9337.

Ebeling, J.G., Vandenbark, G.R., Kuhn, L.J., Ganong, B.R., Bell, R.M., Niedel, J.E. (1985) Diacylglycerols mimic phorbol diester induction of leukemic cell differentiation. Proc. Natl. Acad. Sci. USA 82:815 819.

Ebina, Y., Araki, E., Taira, M., Shimada, F., Mori, M., Craik, C.S., Siddle, K., Pierce, S.B., Roth, R.A. and Rutter, W.J. (1987) Replacement of lysine residue 1030 in the putative ATP binding region of the insulin receptor abolishes insulin and antibody stimulated glucose uptake and receptor kinase activity. Proc. Natl. Acad. Sci. USA 84(3):704 708.

Ebina, Y., Edery, M., Ellis, L., Standring, D., Beaudoin, J., Roth, R.A. and Rutter, W.J. (1985) Expression of a functional human

(56) References Cited

OTHER PUBLICATIONS insulin receptor from a cloned cDNA in Chinese hamster ovary cells. Proc. Natl. Acad. Sci. USA 82:8014 8018.
Elespuru, R.K. and White, R.J. (1983) Biochemical prophage induction assay: a rapid test for antitumor agents that interact with DNA. Cancer Res. 43:2819 2830.
Elespuru, R.K. and Yarmolinsky, M.B. (1979) A colorimetric assay of lysogenic induction designed for screening potential carcinogenic and carcinostatic agents. Environ. Mutagen. 1:65 78.
Ellis, L., Clauser, E., Morgan, D.O., Edery, M., Roth, R.A. and Rutter, W.J. (1986) Replacement of insulin receptor tyrosine residues 1162 and 1163 compromises insulin stimulated kinase activity and uptake of 2 deoxyglucose. Cell 45:721 732.
Erikson, R.L., Purchio, A.F., Erikson, E., Collett, M.S., Brugge, J.S. (1980) Molecular events in cells transformed by Rous Sarcoma virus. J. Cell Biol. 87:319 325.
Escobedo, J.A., Keating, M.T., Ives, H.E. and Williams, L.T. (1988) Platelet derived growth factor receptors expressed by cDNA transfection couple to a diverse group of cellular responses associated with cell proliferation. J. Biol. Chem. 263:1482 1487.
Fairbanks, K.P., Barbu, V.D., Witte, L.D., Weinstein, I.B. and Goodman, D.S. (1986) Effects of mevinolin and mevalonate on cell growth in several transformed cell lines. J. Cell. Physiol. 127:216 222.
Farmerie, W.G., Loeb, D.D., Casavant, N.C., Hutchison, C.A. 3d, Edgell, M.H. and Swanstrom, R. (1987) Expression and processing of the AIDS virus reverse transcriptase in *Escherichia coli*. Science 236:305 308.
Feramisco, J.R., Clark, R., Wong, G., Arnheim, N., Milley, R., McCormick, F. (1985) Transient reversion of ras oncogene induced cell transformation by antibodies specific for amino acid 12 of ras protein. Nature 314(6012):639 642.
Fojo, A., Akiyama, S., Gottesman, M.M., Pastan, I. (1985) Reduced drug accumulation in multiply drug resistant human KB carcinoma cell lines. Cancer Res. 45:3002 3007.
Fojo, A.T., Whang Peng, J., Gottesman, M.M., Pastan, I. (1985) Amplification of DNA sequences in human multidrug resistant KB carcinoma cells. Proc. Natl. Acad. Sci. USA. 82:7661 7665.
Fojo, A., Cornwell, M., Cardarelli, C., Clark, D.P., Richert, N., Shen, D.W., Ueda, K., Willingham, M., Gottesman, M.M., Pastan, I. (1987) Molecular biology of drug resistance. Breast Cancer Res. Treat. 9:5 16.
Fontana, S., Del Vecchio, L., Racioppi, L., Carbone, E., Pinto, A., Colletta, G., Zappacosta, S. (1987) Expression of major histocompatibility complex class I antigens in normal and transformed rat thyroid epithelial cell lines. Cancer Res. 47:4178 4183.
Fraser, C.M., Chung, F.Z. and Venter, J.C. (1987) Continuous high density expression of human beta 2 adrenergic receptors in a mouse cell line previously lacking beta receptors. J. Biol. Chem. 262:14843 14846.
Freedman, V.H. and Shin, S.I. (1974) Cellular tumorigenicity in nude mice: correlation with cell growth in semi solid medium. Cell 3:355 359.
Freeman, A.E., Price, P.J., Igel, H.J., Young, J.C., Maryak, J.M. and Huebner, R.J. (1970) Morphological transformation of rat embryo cells induced by dimethylnitrosamine and murine lukemia viruses. J. Natl. Cancer Inst. 44:65-78.
Friis, R.R., Schwarz, R.T., Schmidt, M.F. (1977) Phenotypes of Rous sarcoma virus transformed fibroblasts: an argument for a multifunctional Src gene product. Med. Microbiol. Immunol. (Berl). 164:155 165.
Fukazawa, H., Uehara, Y., Murakami, Y., Mizuno, S., Hamada, M. and Takeuchi, T. (1994) Labeling of v Src and BCR ABL tyrosine kinases with [14C]herbimycin A and its use in the elucidation of the kinase inactivation mechanism. FEBS Lett. 340:155 158.
Fukuda, K., Kubo, T., Akiba, I., Maeda, A., Mishina, M., Numa, S. (1987) Molecular distinction between muscarinic acetylcholine receptor subtypes. Nature 327:623 625.
Gallick et al. (1988) Specific Reduction in SRC Kinase Activity in HT 29 Humal Colorectal Carcinomal Cells Correlates with Growth Inhibition by Interperon and Tumor Necrosis Factor. UCLA Symposia on Melecular & Cellular Biology Abstract D 207, Jan. 17 Jan. 30, 1988.
Gerlach, J.H., Endicott, J.A., Juranka, P.F., Henderson, G., Sarangi, F., Deuchars, K.L., Ling, V. (1986) Homology between P glycoprotein and a bacterial haemolysin transport protein suggests a model for multidrug resistance. Nature 324(6096):485 489.
Gherzi, R., Russell, D.S., Taylor, S.I. and Rosen, O.M. (1987) Reevaluation of the evidence that an antibody to the insulin receptor is insulinmimetic without activating the protein tyrosine kinase activity of the receptor. J. Biol. Chem. 262:16900 16905.
Giguere, V., Hollenberg, S.M., Rosenfeld, M.G. and Evans, R.M. (1986) Functional domains of the human glucocorticoid receptor. Cell 46:645 652.
Gill, G.N., Santon, J.B., Bertics, P.J. (1987) Regulatory features of the epidermal growth factor receptor. J. Cell. Physiol. Suppl. 5:35 41.
Glick, M.C., De Santis, R., Santer, U.V. (1985) Glycosylation changes in membrane glycoproteins after transfection of NIH 3T3 with human tumor DNA. Prog. Clin. Biol. Res. 175:229 237.
Gooding, L.R., Geib, R.W., O'Connell, K.A. and Harlow, E. (1984) Antibody and cellular detection of SV40 T-antigenic determinants on the surfaces of transformed cells. In Levine, A.J. et al. (Eds), Cancer Cells 1: The Transformed Phenotype pp. 263-269. (Cold Spring Harbor Laboratory, Cold Spring Harbor, N.Y.).
Gorre, Mercedes E. et al. Clinical Reistaance to STI-571 Cancer Therapy Caused by BCR-ABL Gene Mutation or Amplification, Science (2001) vol. 293, pp. 876-880.
Gould, K.L., Woodgett, J.R., Cooper, J.A., Buss, J.E., Shalloway, D. and Hunter, T. (1985) Protein kinase C phosphorylates pp60src at a novel site. Cell 42:849 857.
Grabau, C.L. (1987) Genetic and biochemical characterization of the lipid protein interactions of pyruvate oxidase. U. of Illinois Ph.D. Dissertation.
Graham, F.L. and van der Eb, A.J. (1973) A new technique for the assay of infectivity of human adenovirus 5 DNA. Virology 52:456 467.
Green, S., Walter, P., Kumar, V., Krust, A., Bornert, J.M., Argos, P., Chambon, P. (1986) Human oestrogen receptor cDNA: sequence, expression and homology to v erb A. Nature. 320(6058):134 139.
Grieveson, A.P.H. (1987) Enhancement of extracellular enzyme secretion in Bacillus lichenformis NCIB 6346. Ph.D. Dissertation.
Gros, P., Ben Neriah, Y., Croop, J.M., Housman, D.E. (1986) Isolation and expression of a complementary DNA that confers multidrug resistance. Nature 323(6090):728 731.
Gros, P., Croop, J., Housman, D. (1986) Mammalian multidrug resistance gene: complete cDNA sequence indicates strong homology to bacterial transport proteins. Cell 47:371 380.
Guillem, J.G., O'Brian, C.A., Fitzer, C.J., Forde, K.A., LoGerfo, P., Treat, M., Weinstein, I.B. (1987) Altered levels of protein kinase C and Ca2+ dependent protein kinases in human colon carcinomas. Cancer Res. 47:2036 2039.
Gunter, K.C., Kroczek, R.A., Shevach, E.M. and Germain, R.N. (1986) Functional expression of the murine Thy 1.2 gene in transfected human T cells. J. Exp. Med. 163:285 300.
Hamada, H., Tsuruo, T. (1986) Functional role for the 170 to 180 kDa glycoprotein specific to drug resistant tumor cells as revealed by monoclonal antibodies. Proc. Natl. Acad. Sci. U S A. 83:7785 7789.
Hapel, A.J., Vande Woude, G., Campbell, H.D., Young, I.G. and Robins, T. (1986) Generation of an autocrine leukaemia using a retroviral expression vector carrying the interleukin 3 gene. Lymphokine Res. 5:249 254.
Hillova, J., Hill, M., Belehradek, J. Jr., Mariage Samson, R., Brada, Z. (1986) Loss of the oncogene from human H ras 1 transfected NIH/3T3 cells grown in the presence of excess methionine. J. Natl. Cancer Inst. 77:721 732.
Honegger, A.M., Szapary, D., Schmidt, A., Lyall, R., Van Obberghen, E., Dull, T.J., Ullrich, A. and Schlessinger, J. (1987) A mutant epidermal growth factor receptor with defective protein tyrosine kinase is unable to stimulate proto oncogene expression and DNA synthesis. Mol. Cell. Biol. 7:4568 4571.

(56) References Cited

OTHER PUBLICATIONS

Horgan, K., Cooke, E., Hallett, M.B., Mansel, R.E. (1986) Inhibition of protein kinase C mediated signal transduction by tamoxifen. Importance for antitumour activity. Biochem. Pharmacol. 35:4463 4465.

Horowitz, A.D., Greenebaum, E. and Weinstein, I.B. (1981) Identification of receptors for phorbol ester tumor promoters in intact mammalian cells and of an inhibitor of receptor binding in biologic fluids. Proc. Natl. Acad. Sci. USA 78:2315 2319.

Horwich, A.L., Fenton, W.A., Firgaira, F.A., Fox, J.E., Kolansky, D., Mellman, I.S., Rosenberg, L.E. (1985) Expression of amplified DNA sequences for ornithine transcarbamylase in HeLa cells: arginine residues may be required for mitochondrial import of enzyme precursor. J. Cell. Biol. 100:1515 1521.

Housey, G.M., Kirschmeier, P., Garte, S.J., Burns, F., Troll, W. and Weinstein, I.B. (1985) Expression of long terminal repeat (LTR) sequences in carcinogen induced murine skin carcinomas. Biochem. Biophys. Res. Commun. 127:391 398.

Housey, G.M., Johnson, M.D., Hsiao, W.L., O'Brian, C.A., Murphy, J.P., Kirschmeier, P. and Weinstein, I.B. (1988) Overproduction of protein kinase C causes disordered growth control in rat fibroblasts. Cell 52:343 354.

Hsiao, W.-L.W., Wu, T., and Weinstein, I.B. (1986) Oncogene induced transformation of a rat embryo fibroblast cell line is enhanced by tumor promoters. Mol. Cell. Biol. 6:1943 1950.

Hsiao, W.-L.W., Lopez. C.A., Weinstein, I.B. (1986) Tumor promoters and a serum factor enhance expression of the transformed phenotype in rat 6 fibroblasts transfected with an activated oncogene. In: Journal of Cellular Biochemistry, Supplement 10C: UCLA Symposia on Molecular & Cellular Biology, Abstract L155, Alan R. Liss, Inc., New York, p. 152.

Hsiao, W.L., Lopez, C.A., Wu, T., Weinstein, I.B. (1987) A factor present in fetal calf serum enhances oncogene induced transformation of rodent fibroblasts. Mol. Cell Biol. 7:3380 3385.

Huang, J.S., Huang, S.S. and Deuel, T.F. (1984) Transforming protein of simian sarcoma virus stimulates autocrine growth of SSV transformed cells through PDGF cell surface receptors. Cell 39:79 87.

Huang, K.-P., Nakabayashi, H. and Huang, F.L. (1986) Isozymic forms of rat brain Ca2+ activated and phospholipid dependent protein kinase. Proc. Natl. Acad. Sci. USA 83:8535 8539.

Huberman, E., Callaham, M.F. (1979) Induction of terminal differentiation in human promyelocytic leukemia cells by tumor promoting agents. Proc. Natl. Acad. Sci. USA 76:1293 1297.

Hudziak, R.M., Schlessinger, J. and Ullrich, A. (1987) Increased expression of the putative growth factor receptor p185HER2 causes transformation and tumorigenesis of NIH 3T3 cells. Proc. Natl. Acad. Sci. USA 84:7159 7163.

Hunter, T., Ling, N. and Cooper, J.A. (1984) Protein kinase C phosphorylation of the EGF receptor at a threonine residue close to the cytoplasmic face of the plasma membrane. Nature 311:480 483.

Jaken, S. and Kiley, S.C. (1987) Purification and characterization of three types of protein kinase C from rabbit brain cytosol. Proc. Natl. Acad. Sci. USA 84:4418 4422.

Jetten, A.M., Shirley, J.E. (1985) Inhibition of ornithine decarboxylase by retinoic acid and difluoromethylornithine in relation to their effects on differentiation and proliferation. Exp. Cell Res. 156:221 230.

Jetten, A.M., Barrett, J.C., Gilmer, T.M. (1986) Differential response to retinoic acid of Syrian hamster embryo fibroblasts expressing v src or v Ha ras oncogenes. Mol. Cell. Biol. 6:3341-3348.

Johnson, M.D., Housey, G.M., O'Brian, C.A., Kirschmeier, P.T., and Weinstein, I.B. (1987) Role of protein kinase C in regulation of gene expression and relevance to tumor promotion. Environ. Health. Perspect. 76:89 95.

Johnsson, A., Betsholtz, C., Heldin, C.H. and Westermark, B. (1985) Antibodies against platelet derived growth factor inhibit acute transformation by simian sarcoma virus. Nature 317:438 440.

Johnson, M.D., Housey, G.M., Kirschmeier, P.T. and Weinstein, I.B. (1987) Molecular cloning of gene sequences regulated by tumor promoters and mitogens through protein kinase C. Mol. Cell. Biol. 7:2821 2829.

Juliano, R.L., Ling, V. (1976) A surface glycoprotein modulating drug permeability in Chinese hamster ovary cell mutants. Biochim Biophys Acta. 455:152 162.

Julius, D., MacDermott, A.B., Axel, R. and Jessell, T.M. (1988) Molecular characterization of a functional cDNA encoding the serotonin 1c receptor. Science 241:558 564.

Julius, D., Livelli, T.J., Jessell, T.M. and Axel, R. (1989) Ectopic expression of the serotonin 1c receptor and the triggering of malignant transformation. Science 244:1057 1062.

Kahn, C.R. and White, M.F. (1988) The insulin receptor and the molecular mechanism of insulin action. J. Clin. Invest.82:1151 1156.

Kara, J., Vacha, P., Holy, A. (1979) 9 (S) (2,3 Dihydroxypropyl)adenine inhibits the transformation of chick embryo fibroblasts infected with Rous sarcoma virus: Evidence for inhibition of enzymatic activity of isolated cellular protein kinases by the drug. FEBS Lett. 107:187 192.

Kasuga, M., Karlsson, F.A. and Kahn, C.R. (1982) Insulin stimulates the phosphorylation of the 95,000 dalton subunit of its own receptor. Science 215:185 187.

Kawamoto, S. and Hidaka, H. (1984) 1 (5 Isoquinolinesulfonyl) 2 methylpiperazine (H 7) is a selective inhibitor of protein kinase C in rabbit platelets. Biochem. Biophys. Res. Commun. 125:258 264.

Kikkawa, U., Takai, Y., Minakuchi, R., Inohara, S. and Nishizuka, Y. (1982) Calcium activated, phospholipid dependent protein kinase from rat brain. Subcellular distribution, purification, and properties. J. Biol. Chem. 257:13341 13348.

Kirschmeier, P.T., Housey, G.M., Johnson, M.D., Perkins, A.S. and Weinstein, I.B. (1988) Construction and characterization of a retroviral vector demonstrating efficient expression of cloned cDNA sequences. DNA 7:219 225.

Klohs, W.D., Steinkampf, R.W., Havlick, M.J., Jackson, R.C. (1986) Resistance to anthrapyrazoles and anthracyclines in multidrug resistant P388 murine leukemia cells: reversal by calcium blockers and calmodulin antagonists. Cancer Res.46:4352 4356.

Knopf, J.L., Lee, M.H., Sultzman, L.A., Kriz, R.W., Loomis, C.R., Hewick, R.M. and Bell, R.M. (1986) Cloning and expression of multiple protein kinase C cDNAs. Cell 46:491 502.

Kobilka, B.K., MacGregor, C., Daniel, K., Kobilka, T.S., Caron, M.G., Lefkowitz, R.J., et al. (1987) Functional activity and regulation of human β2 adrenergic receptors expressed in Xenopus oocytes. J. Biol. Chem. 262:15796 15802.

Kolata, G. (1986) Why do cancer cells resist drugs? Science 231(4735):220 221.

Kraft, A.S., Reeves, J.A. and Ashendel, C.L. (1988) Differing modulation of protein kinase C by bryostatin 1 and phorbol esters in JB6 mouse epidermal cells. J. Biol. Chem. 263:8437 8442.

Kraft, A.S. and Anderson, W.B. (1983) Characterization of cytosolic calcium activated phospholipid dependent protein kinase activity in embryonal carcinoma cells. Effect of retinoic acid induced differentiation of F9 cells to parietal endoderm. J. Biol. Chem. 258:9178 9183.

Krishan, A., Sauerteig, A., Gordon, K., Swinkin, C. (1986) Flow cytometric monitoring of cellular anthracycline accumulation in murine leukemic cells. Cancer Res. 46(4 Pt 1):1768 1773.

Laemmli, U. K. (1970) Cleavage of Structural Proteins during the Assembly of the Head of Bacteriophage T4. Nature 227, 680-685.

Laker, C., Stocking, C., Bergholz, U., Hess, N., De Lamarter, J.F., Ostertag, W. (1987) Autocrine stimulation after transfer of the granulocyte/macrophage colony stimulating factor gene and autonomous growth are distinct but interdependent steps in the oncogenic pathway. Proc. Natl. Acad. Sci. U S A 84:8458 8462.

Lang, R.A., Metcalf, D., Gough, N.M., Dunn, A.R. and Gonda, T.J. (1985) Expression of a hemopoietic growth factor cDNA in a factor dependent cell line results in autonomous growth and tumorigenicity. Cell 43:531 542.

Leach, K.L., James, M.L. and Blumberg, P.M. (1983) Characterization of a specific phorbol ester aporeceptor in mouse brain cytosol. Proc. Natl. Acad. Sci. USA 80:4208 4212.

(56) References Cited

OTHER PUBLICATIONS

Lee, F., Yokota, T., Otsuka, T., Gemmell, L., Larson, N., Luh, J., Arai, K. and Rennick, D. (1985) Isolation of cDNA for a human granulocyte macrophage colony stimulating factor by functional expression in mammalian cells. Proc. Natl. Acad. Sci. USA 82:4360 4364.
Lippman, S.M., Kessler, J.F. and Meyskens, F.L. Jr. (1987) Retinoids as preventive and therapeutic anticancer agents (Part I). Cancer Treat. Rep. 71:391 405.
Livneh, E., Prywes, R., Kashles, O., Reiss, N., Sasson, I., Mory, Y., Ullrich, A. and Schlessinger, J. (1986) Reconstitution of human epidermal growth factor receptors and its deletion mutants in cultured hamster cells. J. Biol. Chem. 261:12490 12497.
Loosfelt, H., Atger, M., Misrahi, M., Guiochon Mantel, A., Meriel, C., Logeat, F., Benarous, R., Milgrom, E. (1986) Cloning and sequence analysis of rabbit progesterone receptor complementary DNA. Proc. Natl. Acad. Sci. U S A. 83:9045 9049.
Lusky, M. and Botchan, M. (1981) Inhibition of SV40 replication in simian cells by specific pBR322 DNA sequences. Nature 293:79 81.
Maddon, P.J., Dalgleish, A.G., McDougal, J.S., Clapham, P.R., Weiss, R.A. and Axel, R. (1986) The T4 gene encodes the AIDS virus receptor and is expressed in the immune system and the brain. Cell 47:333 348.
Makowske, M., Birnbaum, M.J., Ballester, R. and Rosen, O.M. (1986) A cDNA encoding protein kinase C identifies two species of mRNA in brain and GH3 cells. J. Biol. Chem. 261:13389 13392.
Mann, R., Mulligan, R.C. and Baltimore, D. (1983) Construction of a retrovirus packaging mutant and its use to produce helper free defective retrovirus. Cell 33:153 159.
Masui, T., Wakefield, L.M., Lechner, J.F., LaVeck, M.A., Sporn, M.B. and Harris, C.C. (1986) Type beta transforming growth factor is the primary differentiation inducing serum factor for normal human bronchial epithelial cells. Proc. Natl. Acad. Sci. USA 83:2438 2442.
McConlogue, L., Dana, S.L., Coffino, P. (1986) Multiple mechanisms are responsible for altered expression of ornithine decarboxylase in overproducing variant cells. Mol. Cell. Biol. 6:2865 2871.
Meijlink, F., Curran, T., Miller, A.D. and Verma, I.M. (1985) Removal of a 67 base pair sequence in the noncoding region of protooncogene fos converts it to a transforming gene. Proc. Natl. Acad. Sci. USA 82:4987 4991.
Metcalf, D. (1985) The granulocyte macrophage colony stimulating factors. Science 229:16 22.
Metcalf, D., Roberts, T.M., Cherington, and V. Dunn, A.R. (1987) The in vitro behavior of hemopoietic cells transformed by polyoma middle T antigen parallels that of primary human myeloid leukemic cells. EMBO J. 6:3703 3709.
Nakagawa, M., Akiyama, S., Yamaguchi, T., Shiraishi, N., Ogata, J., Kuwano, M. (1986) Reversal of multidrug resistance by synthetic isoprenoids in the KB human cancer cell line. Cancer Res. 46:4453 4457.
Nichols, E.J., Manger, R., Hakomori, S.I., Rohrschneider, L.R. (1987) Transformation by the oncogene v fms: the effects of castanospermine on transformation related parameters. Exp. Cell Res. 173:486 495.
Nishikawa, M., Uemura, Y., Hidaka, H., Shirakawa, S. (1986) 1 (5 Isoquinolinesulfonyl) 2 methylpiperazine(H 7), a potent inhibitor of protein kinases, inhibits the differentiation of HL 60 cells induced by phorbol diester. Life Sci. 39:1101 1107.
Nishizuka, Y. (1984) The role of protein kinase C in cell surface signal transduction and tumour promotion. Nature 308:693 698.
Nishizuka, Y. (1986) Studies and perspectives of protein kinase C. Science 233:305 312.
O'Brian, C.A., Lawrence, D.S., Kaiser, E.T. and Weinstein, I.B. (1984) Protein kinase C phosphorylates the synthetic peptide Arg Arg Lys Ala Ser Gly Pro Pro Val in the presence of phospholipid plus either Ca2+ or a phorbol ester tumor promoter. Biochem. Biophys. Res. Commun. 124:296 302.
O'Brian, C.A., Arcoleo, J.P., Housey, G.M. and Weinstein, I.B. (1985) Studies on protein kinase C and their relevance to tumor promotion. In Levine, A.J. et al. (Eds), Cancer Cells 3: Growth Factors and Transformation pp. 359-363. (Cold Spring Harbor Laboratory, Cold Spring Harbor, N.Y.).
O'Brian, C.A., Liskamp, R.M., Solomon, D.H. and Weinstein, I.B. (1985) Inhibition of protein kinase C by tamoxifen. Cancer Res. 45:2462 2465.
O'Brian, C.A., Liskamp, R.M., Solomon, D.H., Weinstein, I.B. (1986) Triphenylethylenes: a new class of protein kinase C inhibitors. J. Natl. Cancer Inst. 76:1243 1246.
O'Brian et al., "Specific and Direct Binding Of Protein Kinase C to an Immobilized Tamoxifen Analogue", 1988, cancer Reserch, 48:3626-29.
O'Hara, C.J., Grover, J., Price, G.B. (1984) Cells resistant to cytotoxic drugs are recognized by monoclonal antibody. J. Clin. Immunol. 4:403 411.
Ohno, S., Kawasaki, H., lmajoh, S., Suzuki, K., Inagaki, M., Yokokura, H., Sakoh, T. and Hidaka, H. (1987) Tissue specific expression of three distinct types of rabbit protein kinase C. Nature 325:161 166.
Ono, Y., Kurokawa, T., Fujii, T., Kawahara, K., Igarashi, K., Kikkawa, U., Ogita, K. and Nishizuka, Y. (1986) Two types of complementary DNAs of rat brain protein kinase C. Heterogeneity determined by alternative splicing. FEBS Lett. 206:347 352.
Ono, Y., Kikkawa, U., Ogita, K., Fujii, T., Kurokawa, T., Asaoka, Y., Sekiguchi, K., Ase, K., Igarashi, K. and Nishizuka, Y. (1987) Expression and properties of two types of protein kinase C: alternative splicing from a single gene. Science 236:1116 1120.
Palaszynski, E.W., Ihle, J.N. (1984) Evidence for specific receptors for interleukin 3 on lymphokine dependent cell lines established from long term bone marrow cultures. J. Immunol. 132:1872 1878.
Parker, P.J., Coussens, L., Totty, N., Rhee, L., Young, S., Chen, E., Stabel, S., Waterfield, M.D. and Ullrich, A. (1986) The complete primary structure of protein kinase C the major phorbol ester receptor. Science 233:853 859.
Pauwels, R., De Clercq, E., Desmyter, J., Balzarini, J., Goubau, P., Herdewijn, P., Vanderhaeghe, H., Vandeputte, M. (1987) Sensitive and rapid assay on MT 4 cells for detection of antiviral compounds against the AIDS virus. J. Virol. Methods 16:171 185.
Perkins, A.S., Kirschmeier, P.T., Gattoni Celli, S. and Weinstein, I.B. (1983) Design of a retrovirus derived vector for expression and transduction of exogenous genes in mammalian cells. Mol. Cell. Biol. 3:1123 1132.
Persons, D.A., Wilkison, W.O., Bell, R.M., Finn, O.J. (1988) Altered growth regulation and enhanced tumorigenicity of NIH 3T3 fibroblasts transfected with protein kinase C I cDNA. Cell 52:447 458.
Pontremoli, S., Melloni, E., Michetti, M., Sparatore, B., Salamino, F., Sacco, O. and Horecker, B.L. (1987) Phosphorylation and proteolytic modification of specific cytoskeletal proteins in human neutrophils stimulated by phorbol 12 myristate 13 acetate. Proc. Natl. Acad. Sci. USA 84:3604 3608.
Pritchett, D.B., Bach, A.W., Wozny, M., Taleb, O., Dal Toso, R., Shih, J.C. and Seeburg, P.H. (1988) Structure and functional expression of cloned rat serotonin 5HT 2 receptor. EMBO J. 7:4135 4140.
Prywes, R., Livneh, E., Ullrich, A. and Schlessinger, J. (1986) Mutations in the cytoplasmic domain of EGF receptor affect EGF binding and receptor internalization. EMBO J. 5:2179 2190.
Quillardet, P., Huisman, O., D'Ari, R. and Hofnung, M. (1982) SOS chromotest, a direct assay of induction of an SOS function in *Escherichia coli* K 12 to measure genotoxicity. Proc. Natl. Acad. Sci. USA 79:5971 5975.
Racker, E., Resnick, R.J., Feldman, R.. (1985) Glycolysis and methylaminoisobutyrate uptake in rat 1 cells transfected with ras or myc oncogenes. Proc. Natl. Acad. Sci. U S A. 82:3535 3538.
Riedel, H., Schlessinger, J., Ullrich, A. (1987) A chimeric, ligand binding v erbB/EGF receptor retains transforming potential. Science 236:197 200.
Roninson, I.B., Abelson, H.T., Housman, D.E., Howell, N., Varshavsky, A. (1984) Amplification of specific DNA sequences correlates with multi drug resistance in Chinese hamster cells. Nature 309(5969):626 628.
Roninson, I.B., Chin, J.E., Choi, K.G., Gros, P., Housman, D.E., Fojo, A., Shen, D.W., Gottesman, M.M., Pastan, I. (1986) Isolation

(56) References Cited

OTHER PUBLICATIONS of human mdr DNA sequences amplified in multidrug resistant KB carcinoma cells. Proc. Natl. Acad. Sci. USA 83:4538 4542.
Roninson, I.B., Chin, J.E., Choi, K. (1986) Mdr gene amplification in multidrug-resistant cells. In: Journal of Cellular Biochemistry, Supplement 10A: UCLA Symposia on Molecular & Cellular Biology, Abstract A18, Alan R. Liss, Inc., New York, p. 12.
Roninson, I.B. (1987) Molecular mechanism of multidrug resistance in tumor cells. Clin. Physiol. Biochem. 5:140 151.
Rosenthal, A., Lindquist, P.B., Bringman, T.S., Goeddel, D.V. and Derynck, R. (1986) Expression in rat fibroblasts of a human transforming growth factor alpha cDNA results in transformation. Cell 46:301 309.
Rovera, G., Santoli, D., Damsky, C. (1979) Human promyelocytic leukemia cells in culture differentiate into macrophage like cells when treated with a phorbol diester. Proc. Natl. Acad. Sci. USA. 76:2779 2783.
Riordan, J.R., Deuchars, K., Kartner, N., Alon, N., Trent, J., Ling, V. (1985) Amplification of P glycoprotein genes in multidrug resistant mammalian cell lines. Nature 316(6031):817 819.
Roth, C.W., Singh, T., Pastan, I. and Gottesman, M.M. (1982) Rous sarcoma virus transformed cells are resistant to cyclic AMP. J. Cell Physiol. 111:42 48.
Rubin, L.A., Hoekzema, G.S., Nelson, D.L., Greene, W.C. and Jay, G. (1987) Reconstitution of a functional interleukin 2 receptor in a nonlymphoid cell. J. Immunol. 139:2355 2360.
Safa, A.R., Glover, C.J., Sewell, J.L., Meyers, M.B., Biedler, J.L., Felsted, R.L. (1987) Identification of the multidrug resistance related membrane glycoprotein as an acceptor for calcium channel blockers. J. Biol. Chem. 262:7884 7888.
Safa, A.R. (1988) Photoaffinity labeling of the multidrug resistance related P glycoprotein with photoactive analogs of verapamil. Proc. Natl. Acad. Sci. U S A. 85:7187 7191.
Sakai, Y., Kimura, and H. Okamoto, K. (1986) Pharmacological characterization of serotonin receptor induced by rat brain messenger RNA in Xenopus oocytes. Brain Res. 362:199 203.
Salomon, D.S., Perroteau, I., Kidwell, W.R., Tam, J., Derynck, R. (1987) Loss of growth responsiveness to epidermal growth factor and enhanced production of alpha transforming growth factors in ras transformed mouse mammary epithelial cells. J. Cell. Physiol. 130:397 409.
Samid, D., Chang, E.H., Friedman, R.M. (1984) Biochemical correlates of phenotypic reversion in interferon treated mouse cells transformed by a human oncogene. Biochem. Biophys. Res. Commun. 119:21 28.
Samid, D., Chang, E.H., Friedman, R.M. (1985) Development of transformed phenotype induced by a human ras oncogene is inhibited by interferon. Biochem. Biophys. Res. Commun. 126:509 516.
Shah, D.M., Horsch, R.B., Klee, H.J., Kishore, G.M., Winter, J.A., Tumer, H.J., Hironaka, C.M., Sanders, P.R., Gasser, C.S., Aykent, S., Sigel, N.R., Rogers, S.G. and Fraley, R.T. (1986) Engineering herbicide tolerance in transgenic plants. Science 233:478-481.
Shen, D.W., Cardarelli, C., Hwang, J., Cornwell, M., Richert, N., Ishii, S., Pastan, I., Gottesman, M.M. (1986) Multiple drug resistant human KB carcinoma cells independently selected for high level resistance to colchicine, adriamycin, or vinblastine show changes in expression of specific proteins. J. Biol. Chem. 261:7762 7770.
Shen, D.W., Fojo, A., Chin, J.E., Roninson, I.B., Richert, N., Pastan, I., Gottesman, M.M. (1986) Human multidrug resistant cell lines: increased mdr1 expression can precede gene amplification. Science 232(4750):643 645.
Shiroki, K., Hashimoto, S., Saito, I., Fukui, Y., Fukui, Y., Kato, H. and Shimojo, H. (1984) Expression of the E4 gene is required for establishment of soft agar colony forming rat cell lines transformed by the adenovirus 12 E1 gene. J. Virol. 50:854 863.
Sibley, D.R., Benovic, J.L., Caron, M.G. and Lefkowitz, R.J. (1987) Regulation of transmembrane signaling by receptor phosphorylation. Cell 48:913 922.
Sorrentino, V., Drozdoff, V., McKinney, M.D., Zeitz, L. and Fleissner, E. (1986) Potentiation of growth factor activity by exogenous c myc expression. Proc. Natl. Acad. Sci. USA 83:8167 8171.
Stabel, S., Rodriguez Pena, A., Young, S., Rozengurt, E. and Parker, P.J. (1987) Quantitation of protein kinase C by immunoblot expression in different cell lines and response to phorbol esters. J. Cell. Physiol. 130:111 117.
Stern, D.F., Roberts, A.B., Roche, N.S., Sporn, M.B. and Weinberg, R.A. (1986) Differential responsiveness of myc and ras transfected cells to growth factors: selective stimulation of myc transfected cells by epidermal growth factor. Mol. Cell. Biol. 6:870 877.
Strader, C.D., Sigal, I.S., Register, R.B., Candelore, M.R., Rands, E., Dixon, R.A. (1987) Identification of residues required for ligand binding to the beta adrenergic receptor. Proc. Natl. Acad. Sci. U S A. 84:4384 4388.
Strader, C.D., Sigal, I.S., Blake, A.D., Cheung, A.H., Register, R.B., Rands, E., Zemcik, B.A., Candelore, M.R., Dixon, R.A. (1987) The carboxyl terminus of the hamster beta adrenergic receptor expressed in mouse L cells is not required for receptor sequestration. Cell 49:855 863.
Strader, C.D., Dixon, R.A., Cheung, A.H., Candelore, M.R., Blake, A.D., Sigal, I.S. (1987) Mutations that uncouple the beta adrenergic receptor from Gs and increase agonist affinity. J. Biol. Chem. 262:16439 16443.
Strader, C.D., Candelore, M.R., Rands, E., Dixon, R.A. (1987) Beta adrenergic receptor subtype is an intrinsic property of the receptor gene product. Mol. Pharmacol. 32:179 183.
Stryer, L. (1981) Biochemistry pp. 854-855.
Stumpo, D.J., Stewart, T.N., Gilman, M.Z., Blackshear, P.J. (1988) Identification of c fos sequences involved in induction by insulin and phorbol esters. J. Biol. Chem. 263:1611 1614.
Takahashi, T., Kuno, M., Mishina, M., Numa, S. (1985) A physiological study on acetylcholine receptor expressed in Xenopus oocytes from cloned cDNAs. J. Physiol. (Paris) 80:229 232.
Takeuchi, M., Sato, Y. and Nitta, K. (1984) An in vitro screening method for antitumor and/or antitumorigenic substances involving the transformation of chick embryo fibroblasts infected with Rous sarcoma virus. J. Antibiot. (Tokyo) 37:235 238.
Taparowsky, E., Suard, Y., Fasano, O., Shimizu, K., Goldfarb, M., Wigler, M. (1982) Activation of the T24 bladder carcinoma transforming gene is linked to a single amino acid change. Nature 300(5894):762 765.
Tseng, A. Jr., Lee, W.M., Jakobovits, E.B., Kirsten, E., Hakam, A., McLick, J., Buki, K., Kun, E. (1987) Prevention of tumorigenesis of oncogene transformed rat fibroblasts with DNA site inhibitors of poly(ADP ribose) polymerase. Proc. Natl. Acad. Sci. USA 84:1107 1111.
Tsuruo, T., Iida, H., Tsukagoshi, S., Sakurai, Y. (1981) Overcoming of vincristine resistance in P388 leukemia in vivo and in vitro through enhanced cytotoxicity of vincristine and vinblastine by verapamil. Cancer Res. 41:1967 1972.
Tsuruo, T., Iida, H., Tsukagoshi, S., Sakurai, Y. (1983) Potentiation of vincristine and Adriamycin effects in human hemopoietic tumor cell lines by calcium antagonists and calmodulin inhibitors. Cancer Res. 43:2267 2272.
Tsuruo, T., Kawabata, H., Nagumo, N., Iida, H., Kitatani, Y., Tsukagoshi, S., Sakurai, Y. (1985) Potentiation of antitumor agents by calcium channel blockers with special reference to cross resistance patterns. Cancer Chemother. Pharmacol. 15:16 19.
Ueda, K., Cornwell, M.M., Gottesman, M.M., Pastan, I., Roninson, I.B., Ling, V., Riordan, J.R. (1986) The mdr1 gene, responsible for multidrug resistance, codes for P glycoprotein. Biochem. Biophys. Res. Commun. 141:956 962.
Ueda, K., Cardarelli, C., Gottesman, M.M., Pastan, I. (1987) Expression of a full length cDNA for the human "MDR1" gene confers resistance to colchicine, doxorubicin, and vinblastine. Proc. Natl. Acad. Sci. U S A. 84:3004 3008.
Uehara, Y., Hori, M., Takeuchi, T. and Umezawa, H. (1985) Screening of agents which convert 'transformed morphology' of Rous sarcoma virus infected rat kidney cells to 'normal morphology': identification of an active agent as herbimycin and its inhibition of intracellular src kinase. Jpn. J. Cancer Res. 76:672 675.

(56) References Cited

OTHER PUBLICATIONS

Uehara, Y., Hori, M., Takeuchi, T. and Umezawa, H. (1986) Phenotypic change from transformed to normal induced by benzoquinonoid ansamycins accompanies inactivation of p60src in rat kidney cells infected with Rous sarcoma virus. Mol. Cell. Biol. 6:2198 2206.
Uehara, Y. (1986) Cancer gene inhibitor and its screening. Oncologia 19:90-93. (in Japanese with accompanying English translation).
Uehara, Y. and Hori, Y. (1987) An approach to developing anti tumor agents by using the cells expressing particular oncogenes. Taisha 24:197-203. (in Japanese with accompanying English translation).
Uehara, Y., Murakami, Y., Mizuno, S., Kawai, S. (1988) Inhibition of transforming activity of tyrosine kinase oncogenes by herbimycin A. Virology 164:294 298.
Uehara, Y., Fukazawa, H., Murakami, Y. and Mizuno, S. (1989) Irreversible inhibition of v src tyrosine kinase activity by herbimycin A and its abrogation by sulfhydryl compounds. Biochem. Biophys. Res. Commun. 163:803 809.
Ullrich, A., Coussens, L., Hayflick, J.S., Dull, T.J., Gray, A., Tam, A.W., Lee, J., Yarden, Y., Libermann, T.A., Schlessinger, J., Downward, J., Mayes, E.L.V., Whittle, N., Waterfield, M.D. and Seeburg, P.H. (1984) Human epidermal growth factor receptor cDNA sequence and aberrant expression of the amplified gene in A431 epidermoid carcinoma cells. Nature 309:418 425.
Umbach, J.A., Gundersen, C.B. (1987) Expression of an omega-conotoxin-sensitive calcium channel in Xenopus oocytes injected with mRNA from Torpedo electric lobe. Proc. Natl. Acad. Sci. USA 84:5464-5468.
Umezawa, H., Imoto, M., Sawa, T., Isshiki, K., Matsuda, N., Uchida, T., Iinuma, H., Hamada, M., Takeuchi, T., (1986) Studies on a new epidermal growth factor-receptor kinase inhibitor, erbstatin, produced by MH435-hF3. J. Antibiot. (Tokyo) 39:170-3.
Von Hoff, D.D., Forseth, B. and Warfel, L.E. (1985) Use of a radiometric system to screen for antineoplastic agents: correlation with a human tumor cloning system. Cancer Res. 45:4032 4038.
Von Meyenburg, K., Jorgensen, B.B., Michelsen, O., Sorensen, L., McCarthy, J.E. (1985) Proton conduction by subunit a of the membrane-bound ATP synthase of *Escherichia coli* revealed after induced overproduction. EMBO J. 4:2357-2363.
Weinstein, I.B., Gattoni-Celli, S., Kirschmeier, P., Lambert, M., Hsiao, W., Backer, J. and Jeffrey, A. (1984) Multistage carcinogenesis involves multiple genes and multiple mechanisms. In Levine, A.J. et al. (Eds), Cancer Cells 1: The Transformed Phenotype pp. 229-237 (Cold Spring Harbor Laboratory, Cold Spring Harbor, N.Y.).
Weinstein I.B., O'Brian, C.A., Housey, G.M., Johnson, M.D., Kirschmeier, P. and Hsiao, W. (1987) Studies on the mechanism of action of protein kinase C and the isolation of molecular clones encoding the enzyme. Symp. Fundam. Cancer Res. 39:173 183.
Weinstein, I.B. (1987) Growth factors, oncogenes, and multistage carcinogenesis. J. Cell. Biochem. 33:213 224.
Weiss, A.A., Imboden, J., Shoback, D., Stobo, J. (1984) Role of T3 surface molecules in human T cell activation: T3 dependent activation results in an increase in cytoplasmic free calcium. Proc. Natl. Acad. Sci. U S A 81:4169 4173.
White, M.F., Livingston, J.N., Backer, J.M., Lauris, V., Dull, T.J., Ullrich, A. and Kahn, C.R. (1988) Mutation of the insulin receptor at tyrosine 960 inhibits signal transmission but does not affect its tyrosine kinase activity. Cell 54:641 649.
Wigler, M., Silverstein, S., Lee, L.-S., Pellicer, A., Cheng, Y.-C. and Axel, R. (1977) Transfer of purified herpes virus thymidine kinase gene to cultured mouse cells. Cell 11:223 232.
Willingham, M.C., Cornwell, M.M., Cardarelli, C.O., Gottesman, M.M., Pastan, I. (1986) Single cell analysis of daunomycin uptake and efflux in multidrug resistant and sensitive KB cells: effects of verapamil and other drugs. Cancer Res. 46:5941 5946.
Woodgett, J.R., Gould, K.L. and Hunter, T. (1986) Substrate specificity of protein kinase C. Use of synthetic peptides corresponding to physiological sites as probes for substrate recognition requirements. Eur. J. Biochem. 161:177 184.
Yamamoto, K.R., Alberts, B.M. (1976) Steroid receptors: elements for modulation of eukaryotic transcription. Annu. Rev. Biochem . 45:721 746.
Yanovich, S., Preston, L. (1984) Effects of verapamil on daunomycin cellular retention and cytotoxicity in P388 leukemic cells. Cancer Res. 44:1743 1747.
Yokota, T., Lee, F., Rennick, D., Hall, C., Arai, N., Mosmann, T., Nabel, G., Cantor, H. and Arai, K. (1984) Isolation and characterization of a mouse cDNA clone that expresses mast cell growth factor activity in monkey cells. Proc. Natl. Acad. Sci. USA 81:1070 1074.
Yu, V.C., Richards, M.L. and Sadee, W. (1986) A human neuroblastoma cell line expresses mu and delta opioid receptor sites. J. Biol. Chem. 261:1065 1070.
Adcock, I.M., Lane, S.J. Mechanisms of Steroid Action and Resistance in Inflammation. Journal of Endocrinology, vol. 178 (Sep. 2003) pp. 347-355.
Allen, P.B., Wiedemann, L.M. An Activating Mutation in the ATP Binding Site of the ABL Kinase Domain. The Journal of Biological Chemistry, vol. 271 (Aug. 9, 1996) pp. 19585-19591.
Barthe, C., Cony-Makhoul, P., Melo, J.V., Reiffers, J., Mahon, F,X. Roots of Clinical Resistance to STI-571 Cancer Therapy. Science, vol. 293 (Sep. 21, 2001) p. 2163a.
Berge, S.M., Bighley, L.D., Monkhouse, D.C. Pharmaceutical salts. Journal of Pharmaceutical Science, vol. 66:1 (Jan. 1977) pp. 1-19.
Bolstad, B.M., Irizarry, R.A., Astrand, M., Speed, T.P. A Comparison of Normalization Methods for High Density Oligonucleotide Array Data Based on Variance and Bias. Bioinformatics, vol. 19 (Jan. 22, 2003) pp. 185-193.
Branford, S., Rudzki, Z., Walsh, S., Grigg, A., Arthur, C., Taylor, K., Hermann, R., Lynch, K.P., Hughes, T.P. High Frequency of Point Mutations Clustered Within the Adenosine Triphosphate-Binding Region of BCR/ABL in Patients with Chronic Myeloid Leukemia or Ph-positive Acute Lymphoblastic Leukemia Who Develop Imatinib (STI571) Resistance. Blood, vol. 99 (May 1, 2002) pp. 3472-3475.
Breshears, S.R., Wang, S.S., Bechtolt, S.G., Christensen, B.E. Purines. VIII: The Aminolysis of Certain Chlorosubstituted Purines. Journal of the American Chemical Society, vol. 81 (Jul. 20, 1959) pp. 3789-3792.
Burbaum, J.J., Ohlmeyer, M.H., Reader, J.C., Henderson, I., Dillard, L.W., Li, G., Randle, T.L., Sigal, N.H., Chelsky, D., Baldwin, J.J. A paradigm for drug discovery employing encoded combinatorial libraries. Proceedings of the National Academy of Science U S A, vol. 92 (Jun. 20, 1995) pp. 6027-6031.
Capps, T.M., Heard, N.E., Simmons, D.P., Connor, C.L. Identification and Synthesis of a Unique Disulfide Dimeric Metabolite of Primisulfuron-methyl in the Mouse. Journal of Agricultural and Food Chemistry, vol. 41 (1993) pp. 2411-2415.
Corbin, A.S., Buchdunger, E., Pascal, F., Druker, B.J. Analysis of the Structural Basis of Specificity of Inhibition of the Abl Kinase by STI571. The Journal of Biological Chemistry, vol. 277 (Aug. 30, 2002) pp. 32214-32219.
Daley, G.Q., Van Etten, R.A., Baltimore, D. Induction of Chronic Myelogenous Leukemia in Mice by the P210$^{brc/abl}$ Gene of the Philadelphia Chromosome. Science, vol. 247 (Feb. 16, 1990) pp. 824-830.
Davis, T.L. The Mechanism of Reactions in the Urea Series. Proceedings of the National Academy of Sciences of the United States of America, vol. 11 (1925) pp. 68-73.
Druker, B.J., M.D., Sawyers, C.L., M.D., Kantarjian, H., M.D., Resta, D. J., R.N., Reese, S.F., M.D., Ford, J.M., M.D., Capdeville, R., M.D., Talpaz, M., M.D. Activity of a Specific Inhibitor of the BCR-ABL Tyrosine Kinase in the Blast Crisis of Chronic Myeloid Leukemia and Acute Lymphoblastic Leukemia with the Philadelphia Chromosome. The New England Journal of Medicine, vol. 344 (Apr. 5, 2001) pp. 1038-1042.
Druker, B.J., M.D., Talpaz, M., M.D., Resta, D.J., R.N., Peng, B., Ph.D., Buchdunger, E., Ph.D., Ford, J.M., M.D., Lydon, N.B., Ph.D., Kantarjian, H., M.D., Capdeville, R., M.D., Ohno-Jones, S., B.S., Sawyers, C. L., M.D. Efficacy and Safety of a Specific

(56) References Cited

OTHER PUBLICATIONS

Inhibitor of the BCR-ABL Tyrosine Kinase in Chronic Myeloid Leukemia. The New England Journal of Medicine, vol. 344 (Apr. 5, 2001) pp. 1031-1037.

Druker, B.J., Tamura, S., Buchdunger, E., Ohno, S., Segal, G.M., Fanning, S., Zimmermann, J., Lydon, N.B. Effects of a Selective Inhibitor of the Abl Tyrosine Kinase on the Growth of Bcr-Abl Positive Cells. Nature Medicine, vol. 2:5 (May 1996) pp. 561-566.

Faderl, S., M.D., Talpaz, M., M.D., Estrov, Z., M.D., O'Brien, S., M.D., Kurzrock, R., M.D., Kantarjian, H. M., M.D. The Biology of Chronic Myeloid Leukemia. The New England Journal of Medicine, vol. 341 (Jul. 15, 1999) pp. 164-172.

Gambacorti-Passerini, C., Barni, R., Le Coutre, P., Zucchetti, M., Cabrita, G., Cleris, L., Rossi, F., Gianazza, E., Brueggen, J., Cozens, R., Pioltelli, P., Pogliani, E., Corneo, G., Formelli, F., D'Incalci, M. Role of α1 Acid Glycoprotein in the In Vivo Resistance of Human BCR-ABL$^+$ Leukemic Cells to the Abl Inhibitor STI571. Journal of the National Cancer Institute, vol. 92 (Oct. 18, 2000) pp. 1641-1650.

Gineinah, M.M., El-Sherbeny, M.A., Nasr, M.N., Maarouf, A.R. Synthesis and Antiinflammatory Screening of Some Quinazoline and Quinazolyl-4-oxoquinazoline Derivatives. Archiv der Pharmazie—Pharmaceutical and Medicinal Chemistry, vol. 335 (2002) pp. 556-562.

Goodnow, R.A., Jr., Guba, W., Haap, W. Library design practices for success in lead generation with small molecule libraries. Combinatorial Chemistry and High Throughput Screening, vol. 6 (Nov. 2003) pp. 649-660.

Gorre, M.E., Mohammed, M., Ellwood, K., Hsu, N., Paquette, R., Rao, P.N., Sawyers, C.L. Clinical Resistance to STI-571 Cancer Therapy Caused by BCR-ABL Gene Mutation or Amplification. Science, vol. 293 (Aug. 3, 2001) pp. 876-880.

Hanke, J.H., Gardner, J.P., Dow, R.L., Changelian, P.S., Brissette, W.H., Weringer, E.J., Pollok, B.A., Connelly, P.A. Discovery of a novel, potent, and Src family-selective tyrosine kinase inhibitor. Study of Lck- and FynT-dependent T cell activation. Journal of Biological Chemistry, vol. 271:2 (Jan. 1996) pp. 695-701.

Hofmann, W.K., Jones, L.C., Lemp, N.A., DeVos, S., Gschaidmeier, H., Hoelzer, D., Ottmann, O.G., Koeffler, H. P. Ph$^+$ Acute Lymphoblastic Leukemia Resistant to the Tyrosine Kinase Inhibitor STI571 has a Unique BCR-ABL Gene Mutation. Blood, vol. 99 (Mar. 1, 2002) pp. 1860-1862.

Hou, Y.Y., Tan, Y.S., Sun, M.H., Wei, Y.K., Xu, J.F., Lu, S.H., A-Ke-Su, S.J., Zhou, Y.N., Gao, F., Zheng, A.H., Zhang, T.M., Hou, W.Z., Wang, J., Du, X., Zhu, X.Z. C-kit Gene Mutation in Human Gastrointestinal Stromal Tumors. World Journal of Gastroenterology, vol. 10 (May 1, 2004) pp. 1310-1314.

Housey, G.M. The Role of Protein Kinase C in Growth Control and Tumor Promotion. Ph.D. Dissertation, (1988).

Huang, M.T., Ma, W., Yen, P., Xie, J.G., Han, J., Frenkel, K., Grunberger, D., Conney, A.H. Inhibitory effects of caffeic acid phenethyl ester (CAPE) on 12-O-tetradecanoylphorbol-13-acetate-induced tumor promotion in mouse skin and the synthesis of DNA, RNA and protein in HeLa cells. Carcinogenesis, Apr. 1996;17(4):761-5.

Huron, D.R., Gorre, M.E., Kraker, A.J., Sawyers, C.L., Rosen, N., Moasser, M.M. A Novel Pyridopyrimidine Inhibitor of Abl Kinase is a Picomolar Inhibitor of Bcr-Abl-driven K562 Cells and is Effective Against STI571-resistant Bcr-Abl Mutants. Clinical Cancer Research, vol. 9 (Apr. 2003) pp. 1267-1273.

La Rosee, P., Corbin, A.S., Stoffregen, E.P., Deininger, M.W., Druker, B.J. Activity of the Bcr-Abl Kinase Inhibitor PD180970 Against Clinically Relevant Bcr-Abl Isoforms That Cause Resistance to Imatinib Mesylate (Gleevec, STI-571). Cancer Research, vol. 62 (Dec. 15, 2002) pp. 7149-7153.

Latham, H.G. Jr., May, E.L., Mosettig, E. Amino- and Guanidino-Phenylglucosides. Journal of Organic Chemistry, vol. 15 (1950) pp. 884-889.

Le Coutre, P., Tassi, E., Varella-Garcia, M., Barni, R., Mologni, L., Cabrita, G., Marchesi, E., Supino, R., Gambacorti-Passerini, C. Induction of Resistance to the Abelson Inhibitor STI571 in Human Leukemic Cells Through Gene Amplification. Blood, vol. 95:5 (Mar. 1, 2000) pp. 1758-1766.

Lee, S.P., Jun, G., Yoon, E.J. Park, S., Yang, C.H. Inhibitory Effect of Methyl Caffeate on Fos-Jun-DNA ComplexFormation and Suppression of Cancer Cell Growth Bull. Korean Chem. Soc. 2001, vol. 22, No. 10 1131.

Leonard, G.D., Fojo, T., Bates, S.E. The Role of ABC Transporters in Clinical Practice. The Oncologist, vol. 8 (2003) pp. 411-424.

Loutfy, M.R., Walmsley, S.L. Salvage Antiretroviral Therapy in HIV Infection. Expert Opinion, vol. 3 (Feb. 2002) pp. 81-90.

Lynch, T.J., M.D., Bell, D.W., Ph.D., Sordella, R., Ph.D., Gurubhagavatula, S., M.D., Okimoto, R.A., B.S., Brannigan, B.W., B.A., Harris, P.L., M.S., Haserlat, S.M., B.A., Supko, J.G., Ph.D., Haluska, F.G., M.D., Ph.D., Louis, D.N., M.D., Christiani, D.C., M.D., Settleman, J., Ph.D., Haber, D.A., M.D., Ph.D. Activating Mutations in the Epidermal Growth Factor Receptor Underlying Responsiveness of Non-Small-Cell Lung Cancer to Gefitinib. The New England Journal of Medicine, vol. 350:21 (May 20, 2004) pp. 2129-2139.

Mahon, F.X., Deininger, M.W.N., Schultheis, B., Chabrol, J., Reiffers, J., Goldman, J.M., Melo, J.V. Selection and Characterization of BCR-ABL Positive Cell Lines with Differential Sensitivity to the Tyrosine Kinase Inhibitor STI571: Diverse Mechanisms of Resistance. Blood, vol. 96:3 (Aug. 1, 2000) pp. 1070-1079.

Mansky, L.M., Temin, H.M. Lower In Vivo Mutation Rate of Human Immunodeficiency Virus Type 1 than that Predicted from the Fidelity of Purified Reverse Transcriptase. Journal of Virology, vol. 69 (Aug. 1995) pp. 5087-5094.

Marshall, J.R., Walker, J. Experimental Study of Some Potentially Tautomeric 2- and 4(6)-Substituted Pyrimidines. Journal of the Chemical Society, (1951) pp. 1004-1017.

Marx, J. Why a New Cancer Drug Works Well in Some Patients. Science, vol. 304 (Apr. 30, 2004) pp. 658-659.

Melo, J.V., Myint, H., Galton, D.A., Goldman, J.M. P190BCR-ABL chronic myeloid leukaemia: the missing link with chronic myelomonocytic leukaemia? Leukemia, vol. 8 (Jan. 1994) pp. 208-211.

Nair, M.D., Mehta, S.R. Syntheses and Reactions of Condensed Isoquinolines—Imidazo, Pyrimido, Triazolo and Tetrazolo Isoquinolines. Indian Journal of Chemistry, vol. 5 (Sep. 1967) pp. 403-408.

Noble, M.E.M., Endicott, J.A., Johnson, L.N. Protein Kinase Inhibitors: Insights into Drug Design from Structure. Science, vol. 303 (Mar. 19, 2004) pp. 1800-1805.

O'Hare, T., Pollock, R., Stoffregen, E.P., Keats, J.A., Abdullah, O.M., Moseson, E.M., Rivera, V.M., Tang, H., Metcalf, C.A. 3rd, Bohacek, R.S., Wang, Y., Sundaramoorthi, R., Shakespeare, W.C., Dalgarno, D., Clackson, T., Sawyer, T.K., Deininger, M.W., Druker, B.J. Inhibition of wild-type and mutant Bcr-Abl by AP23464, a potent ATP-based oncogenic protein kinase inhibitor: implications for CML. Blood, vol. 104:8 (Oct. 15, 2004) pp. 2532-2539.

Paez, J.G., Jänne, P.A., Lee, J.C., Tracy, S., Greulich, H., Gabriel, S., Herman, P., Kaye, F.J., Lindeman, N., Boggon, T.J., Naoki, K., Sasaki, H., Fujii, Y., Eck, M.J., Sellers, W.R., Johnson, B.E., Meyerson, M. EGFR Mutations in Lung Cancer: Correlation with Clinical Response to Gefitinib Therapy. Sciencexpress (Apr. 29, 2004) pp. 1-4.

Ravandi, F., Cortes, J., Albitar, M., Arlinghaus, R., Qiang, Guo J., Talpaz, M., Kantarjian, H.M. Chronic myelogenous leukaemia with p185(BCR/ABL) expression: characteristics and clinical significance. British Journal of Haematology, vol. 107 (Dec. 1999) pp. 581-586.

Sawyers,C.L. M.D. Chronic Myeloid Leukemia. The New England Journal of Medicine, vol. 340 (Apr. 29, 1999) pp. 1330-1340.

Schindler, T., Bornmann,W., Pellicena, P., Miller, W.T., Clarkson, B., Kuriyan, J. Structural Mechanism for STI-571 Inhibition of Abelson Tyrosine Kinase. Science, vol. 289 (Sep. 15, 2000) pp. 1938-1942.

Senechal, K., Halpern, J., Sawyers, C.L. The CRKL Adaptor Protein Transforms Fibroblasts and Functions in Transformation by the BCR-ABL Oncogene. The Journal of Biological Chemistry, vol. 271:38 (Sep. 20, 1996) pp. 23255-23261.

Senechal, K., Heaney, C., Druker, B., Sawyers, C.L. Structural Requirements for Function of the Crkl Adapter Protein in Fibro-

(56) References Cited

OTHER PUBLICATIONS blasts and Hematopoietic Cells. Molecular and Cellular Biology, vol. 18:9 (Sep. 1998) pp. 5082-5090.
Shah, N.P., Tran, C., Lee, F.Y., Chen, P., Norris, D., Sawyers, C.L. Overriding Imatinib Resistance with a Novel ABL Kinase Inhibitor. Science, vol. 305 (Jul. 16, 2004) pp. 399-401.
Shearer, B.G., Lee, S., Franzmann, K.W., White, H.A.R., Sanders, D.C.J., Kiff, R.J., Garvey, E.P., Furfine, E.S. Conformationally Restricted Arginine Analogues as Inhibitors of Human Nitric Oxide Synthase. Bioorganic and Medicinal Chemistry Letters, vol. 7 (Jul. 8, 1997) pp. 1763-1768.
Tipping, A.J., Baluch, S., Barnes, D.J., Veach, D.R., Clarkson, B.M., Bornmann, W.G., Mahon, F.X., Goldman, J.M., Melo, J.V. Efficacy of dual-specific Bcr-Abl and Src-family kinase inhibitors in cells sensitive and resistant to imatinib mesylate. Leukemia, vol. 18 (Aug. 2004) pp. 1352-1356.
Von Bubnoff, N., Schneller, F., Peschel, C., Duyster, J. BCR-ABL Gene Mutations in Relation to Clinical Resistance of Philadelphia-Chromosome-Positive Leukemia to STI571: A Prospective Study. The Lancet, vol. 359 (Feb. 9, 2002) pp. 487-491.
Von Bubnoff, N., Veach, D.R., Van Der Kuip, H., Aulitzky, W.E., Sanger, J., Seipel, P., Bornmann, W.G., Peschel, C., Clarkson, B., Duyster, J. A cell-based screen for resistance of Bcr-Abl positive leukemia identifies the mutation pattern for PD166326, an alternative Abl kinase inhibitor. Blood, vol. 105 (Feb. 15, 2005) pp. 1652-1659.
Wakai, T., Kanda, T., Hirota, S., Ohashi, A., Shirai, Y. Hatakeyama, K. Late Resistance to Imatinib Therapy in a Metastatic Gastrointestinal Stromal Tumour is Associated With a Second KIT Mutation. British Journal of Cancer, vol. 90 (Jun. 1, 2004) pp. 2059-2061.
Weigel, U., Meyer, M., Sebald, W. Mutant Proteins of Human Interleukin 2: Renaturation Yield, Proliferative Activity and Receptor Binding. European Journal of Biochemistry, vol. 180 (Mar. 15, 1989) pp. 295-300.
Weisberg, E., Catley, L., Kujawa, J., Atadja, P., Remiszewski, S., Fuerst, P., Cavazza, C., Anderson, K., Griffin, J.D. Histone deacetylase inhibitor NVP-LAQ824 has significant activity against myeloid leukemia cells in vitro and in vivo. Leukemia, vol. 18 (Dec. 2004) pp. 1951-1963.
Weisberg, E., Griffin, J.D. Mechanism of Resistance to the ABL Tyrosine Kinase Inhibitor STI 571 in BCR/ABL-Transformed Hematopoietic Cell Lines. Blood, vol. 95:11 (Jun. 1, 2000) pp. 3498-3505.
Weisberg, E., Manley, P.W., Breitenstein, W., Bruggen, J., Cowan-Jacob, S.W., Ray, A., Huntly, B., Fabbro, D., Fendrich, G., Hall-Meyers, E., Kung, A.L., Mestan, J., Daley, G.Q., Callahan, L., Catley, L., Cavazza, C., Azam, M., Neuberg, D., Wright, R.D., Gilliland, D.G., Griffin, J.D. Characterization of AMN107, a selective inhibitor of native and mutant Bcr-Abl. Cancer Cell, vol. 7 (Feb. 2005) pp. 129-141.
Wu, M.T., MacCoss, M., Ikeler, T.J., Hirshfield, J., Arison, B.H., Tolman, R.L. Annelated Piperazinyl-7,8-dihydro-6H-thiopyrano[3,2-d]pyrimidines. Journal of Heterocyclic Chemistry, vol. 27 (1990) pp. 1559-1563.
Xue, Y., Hang, C. Study of the anti-carcinogenic effects of three compounds in *Kaempferia galanga* L. WeiSheng Yan Jiu, vol. 31 (2002), pp. 247-248.
Akiyama, S., et al., "Isolation and genetic characterization of human KB cell lines resistant to multiple drugs." Somat Cell Mol Genet (1985), vol. 11(2), pp. 117-126.
Ammann, A.J., et al., "Acquired immune dysfunction in homosexual men: immunologic profiles." Clin. Immunol. Immunopathol. (1983), vol. 27(3), pp. 315-325.
Ayusawa, D., et al., "Selection of mammalian thymidine auxotrophic cell mutants defective in thymidylate synthase by their reduced sensitivity to methotrexate." Somatic Cell Genet (1981), vol. 7, pp. 523-534.
Ayusawa, D. et al., "Single step selection of mouse FM3A cell mutants defective in thymidylate synthetase." Somatic Cell Genet. (1980), vol. 6, pp. 261-270.

Balzarini, J. et al., "Strategies for the measurement of the inhibitory effects of thymidine analogs on the activity of thymidylate synthase in intact murine leukemia L1210 cells." Biochim Biophys Acta (1984), vol. 785, pp. 36 45.
Balzarini, J. et al., "Thymidylate synthetase positive and negative murine mammary FM3A carcinoma cells as a useful system for detecting thymidylate synthetase inhibitors." FEBS Lett. (1984), vol. 173, pp. 227 232.
Balzarini, J. et al., "Thymidylate synthetase deficient mouse FM3A mammary carcinoma cell line as a tool for studying the thymidine salvage pathway and the incorporation of thymidine analogues into host cell DNA." Biochem. J. (1984), vol. 217, pp. 245-252.
Balzarini, J. et al., "Thymidylate synthase is the principal target enzyme for the cytostatic activity of (E) 5 (2 bromovinyl) 2' deoxyuridine against murine mammary carcinoma (FM3A) cells transformed with the herpes simplex virus type 1 or type 2 thymidine kinase gene." Mol. Pharmacol. (1987), vol. 32, pp. 410-416.
Barre Sinoussi, F. et al., "Isolation of a T lymphotropic retrovirus from a patient at risk for acquired immune deficiency syndrome (AIDS)." Science (1983) vol. 220(4599), pp. 868-871.
Bartus, H.R. et al., "Improved genetically modified *Escherichia coli* strain for prescreening antineoplastic agents." Antimicrob. Agents Chemother. (1984), vol. 25, pp. 622-625.
Beck, W.T., "Cellular pharmacology of Vinca alkaloid resistance and its circumvention." Adv. Enzyme Regul. (1984), vol. 22, pp. 207-227.
Bender, P.E. et al., "5,6 Diaryl 2,3 dihydroimidazo[2,1 b]thiazoles: a new class of immunoregulatory antiinflammatory agents." J. Med. Chern. (1985), vol. 28, pp. 1169-1177.
Bignami, M. et al., "Tumor promoters enhance v myc induced focus formation in mammalian cell lines." Ann. N.Y. Acad. Sci. (1987), vol. 511, pp. 343-349.
Binder, D. et al., "Analogues and derivatives of tenoxicam. 1. Synthesis and antiinflammatory activity of analogues with different residues on the ring nitrogen and the amide nitrogen." J. Med. Chem. (1987), vol. 30, pp. 678-682.
Blythin, D.J. et al., "Antiinflammatory activity of substituted 6 hydroxypyrimido[2,1 f]purine-2,4,8(1H,3H,9H) triones. Atypical nonsteroidal antiinflammatory agents." J. Med. Chem. (1986), vol. 29, pp. 1099-1113.
Boulianne, G.L. et al., "Production of functional chimaeric mouse/ human antibody." Nature (1984), vol. 312(5995), pp. 643-646.
Bowen, D.L. et al., "Immunopathogenesis of the acquired immunodeficiency syndrome." Ann. Intern. Med. (1985), vol. 103, pp. 704-709.
Bradford, M.M. et al., "A rapid and sensitive method for the quantitation of microgram quantities of protein utilizing the principle of protein-dye binding." Anal. Biochem. (1976), vol. 72, pp. 248-254.
Brooks, K.H. et al., "Recombinant IL 2 but not recombinant interferon gamma stimulates both proliferation and IgM secretion in a Ly 1+ clone of neoplastic murine B cells (BCL1)." J. Immunol. (1986), vol. 137, pp. 3205-3210.
Buzas, A. et al., "Sur la chlorosulfonylation du thiophene et de quelques uns de ses derives substitues." Bulletin De la Societe Francaise de Cancerologie (1960) pp. 793-803.
Chiaini, J. et al., "Excretion and metabolism of a nonsteroidal antiinflammatory agent, 4 hydroxy 2 methyl 2H 1,2 benzothiazine-3 carboxanilide 1,1 dioxide, in rat, dog, monkey, and man." J. Med. Chem. (1971), vol. 14, pp. 1175-1177.
Chakrabarty, S.et al., "Restoration of normal growth control and membrane antigen composition in malignant cells by N,N dimethylformamide." Cancer Res. (1984) vol. 44, pp. 2181-2185.
Chanh, T.C. et al., "Induction of anti HIV neutralizing antibodies by synthetic peptides." EMBO J. (1986), vol. 5, pp. 3065-3071.
Chen, Y.C. et al., "Properties of mammalian cells transformed by temperature sensitive mutants of avian sarcoma virus." Cell (1977), vol. 11, pp. 513-521.
Chen, W-T.et al., "Regulation of fibronectin receptor distribution by transformation, exogenous fibronectin, and synthetic peptides." J. Cell Biol. (1986), vol. 103, pp. 1649-1661.

(56) References Cited

OTHER PUBLICATIONS

Cole, S.P.C. et al., "The EBV-Hybridoma Technique and its Application to Human Lung Cancer." In: Monoclonal Antibodies and Cancer Therapy, pp. 77-96 (R. Reisfeld & S. Sell, eds., Alan R. Liss, N.Y. 1985).
Collard, J.G. et al., "Invasive and metastatic potential induced by ras transfection into mouse BW5147 T lymphoma cells." Cancer Res. (1987), vol. 47, pp. 754-759.
Consonni, R. et al., "Reactivity of 2-Methyl-4-(1-pyrrolidinyl)-2H-1,2-benzothiazine 1,1-dioxide towards p-Toluenesulphonyl Azide." J. Heterocyclic Chem. (1990), vol. 27, pp. 427-430.
Crofford, L.J. "COX 1 and COX 2 tissue expression: implications and predictions." J. Rheumatol. (1997) 24 Suppl 49, pp. 15-19.
Cunningham Rundles, "Serum suppression of lymphocyte activation in vitro in acquired immunodeficiency disease." J. Clin. Immunol. (1983), vol. 3, pp. 156-165.
Cuttitta, F. et al., "Bombesin like peptides can function as autocrine growth factors in human small cell lung cancer." Nature (1985), vol. 316(6031), pp. 823-826.
Dalgleish, A.G.et al., "The CD4 (T4) antigen is an essential component of the receptor for the AIDS retrovirus." Nature (1984), vol. 312(5996), pp. 763-767.
Davies, T. "Magic bullets." Nature (1981), vol. 289(5793), pp. 12-13.
De Clercq, E. et al., "Potent activity of 5 fluoro 2' deoxyuridine and related compounds against thymidine kinase deficient (TK) herpes simplex virus: targeted at thymidylate synthase." Mol. Pharmacol. (1987), vol. 32, pp. 286-292.
Declercq, E.et al., "Thymidylate synthetase as target enzyme for the inhibitory activity of 5 substituted 2' deoxyuridines on mouse leukemia L1210 cell growth." Mol. Pharmacol. (1981), vol. 19, pp. 321-330.
Delclos, K.B. et al., "Specific labeling of mouse brain membrane phospholipids with [20-3H]phorbol 12-p-azidobenzoate 13-benzoate, a photolabile phorbol ester." Proc. Natl. Acad. Sci. USA (1983), vol. 80, pp. 3054-3058.
Dutta-Roy, A.K. et al., "Prostacyclin stimulation of the activation of blood coagulation factor X by platelets." Science (1986), vol. 231(4736), pp. 385-388.
Elroy-Stein, O. et al., "Overproduction of human Cu/Zn superoxide dismutase in transfected cells: extenuation of paraquat mediated cytotoxicity and enhancement of lipid peroxidation." EMBO J. (1986), vol. 5, pp. 615-622.
Erikson, R.L., Towards a biochemical description of malignant transformation. Identification and functional characterization of the Rous sarcoma virus transforming gene product. Cancer (1984), vol. 53, pp. 2041-2045.
Fauci, A.S., "Immunologic abnormalities in the acquired immunodeficiency syndrome (AIDS)." Clin. Res. (1984), vol. 32, pp. 491-499.
Fisher, P.B. et al., "Modulation of differentiation in murine and human cells by interferon and phorbol ester tumor promoters." In: Pigment Cell 1985. Biological, Molecular and Clinical Aspects of Pigmentation (Bagnara, J., Klaus, S. N., Paul, E. & Schartl, M. eds., University of Tokyo Press) p. 325-332.
Fisher, P.B. et al., "Interactions between initiating chemical carcinogens, tumor promoters, and adenovirus in cell transformation." Teratog. Carcinog. Mutagen. (1980) vol. 1, pp. 245-257.
Fraga, C.A.M. et al., "The synthesis of a new benzothiazine derivative, related to oxicams, synthesized from natural safrole." J. Heterocyclic Chem (1992), vol. 29, pp. 1667-1669.
Fu, J.Y. et al., "The induction and suppression of prostaglandin H2 synthase (cyclooxygenase) in human monocytes." J. Biol. Chem. (1990), vol. 265(28), pp. 16737-16740.
Fukazawa, H. et al., "Effects of herbimycin A and various SH-reagents on p60v-src kinase activity in vitro." Biochem Biophys Res Commun. (1990), vol. 173(1), pp. 276-282.
Fukazawa, H. et al., "Specific inhibition of cytoplasmic protein tyrosine kinases by herbimycin A in vitro." Biochem. Pharmacol. (1991), vol. 42(9), pp. 1661-1671.

Fulton, R.J. et al., "Purification of ricin A1, A2, and B chains and characterization of their toxicity." J. Biol. Chem. (1986), vol. 261, pp. 5314-5319.
Fung, M.S.C. et al., "Monoclonal antibodies that neutralize HIV-1 virions and inhibit syncytium formation by infected cells." Bio/technology (1987), vol. 5, pp. 940-946.
Gallo, R.C. et al., "Frequent detection and isolation of cytopathic retroviruses (HTLV III) from patients with AIDS and at risk for AIDS." Science (1984), vol. 224(4648), pp. 500-503.
Gill, G.N. et al., "Monoclonal anti epidermal growth factor receptor antibodies which are inhibitors of epidermal growth factor binding and antagonists of epidermal growth factor binding and antagonists of epidermal growth factor stimulated tyrosine protein kinase activity." J. Biol. Chem. (1984), vol. 259, pp. 7755-7760.
Gohji, K. et al., "Enhanced inhibition of colony formation of human renal cell carcinoma in soft agar by the combination of alpha difluoromethylornithine and recombinant gamma interferon." Cancer Res. (1986), vol. 46, pp. 6264-6268.
Goodman & Gilman, The Pharmacological Basis of Therapeutics, 9th ed. (1996) Chapter 2.
Goto, R. et al., "Characteristics of D leucine uptake by mouse Ehrlich ascites tumor cells." J. Biochem. (1979) (Tokyo), vol. 86, pp. 363-369.
Goustin, A.S. et al., "Growth factors and cancer." Cancer Res. (1986), vol. 46, pp. 1015-1029.
Gros, P. et al., "Chromosome mediated gene transfer of multidrug resistance." Mol. Cell Biol. (1986), vol. 6, pp. 3785-3790.
Guadagno, T.M. et al., "A link between cyclin A expression and adhesion-dependent cell cycle progression." Science (1993), vol. 262(5139), pp. 1572-1575.
Hakomori, S., "Tumor associated carbohydrate antigens." Annu. Rev. Immunol. (1984), vol. 2, pp. 103-126.
Hallek, M. et al., "Signal transduction of interleukin-6 involves tyrosine phosphorylation of multiple cytosolic proteins and activation of Src-family kinases Fyn, Hck, and Lyn in multiple myeloma cell lines." Exp Hematol. (1997), vol. 25(13), pp. 1367-1377.
Hibshoosh, H. et al., "Effects of overexpression of ornithine decarboxylase (ODC) on growth control and oncogene-induced cell transformation." Oncogene (1991), vol. 6(5), pp. 739-743.
Hori, M. et al., "Antibiotics Inhibiting Oncogene Functions." Gann Monograph on Cancer Research (1989), vol. 36, pp. 193-201.
Housey, G. M., et al. "Isolation and nucleotide sequence analysis of cDNA clones from rat brain using oligonucleotide probes to protein kinase C and protein kinase A." In: Journal of Cellular Biochemistry, Supplement 10C: UCLA Symposia on Molecular & Cellular Biology, Abstract L95, Alan R. Liss, Inc., New York, p. 132, (1986).
Housey, G.M., et al., "Isolation of cDNA clones encoding protein kinase C: evidence for a protein kinase C related gene family." Proc. Natl. Acad. Sci. USA (1987), vol. 84, pp. 1065-1069.
Housey, G.M. et al., "Structural and functional studies of protein kinase C. Adv. Exp." Med. Biol. (1988), vol. 234, pp. 127-140.
Housey, G.M. et al., "Altered Growth Control and Enhanced Morphologic Response to Tumor Promoters in Rat Fibroblasts Stably Overproducing Protein Kinase C." In: Journal of Cellular Biochemistry, Supplement 12A: UCLA Symposia on Molecular & Cellular Biology, (Jan. 17-Jan. 30, 1988), Abstract C224, Alan R. Liss, Inc., New York, p. 105.
Hsiao, W.-L.W. et al., "Oncogene induced transformation of C3H 10T1/2 cells is enhanced by tumor promoters." Science (1984), vol. 226, pp. 552-555.
Hsyu, P.H. et al., "Pharmacokinetics and cyclooxygenase inhibition of itazigrel in normal volunteers after single oral doses." J. Pharm. Sci. (1994), vol. 83, pp. 1747-1750.
Huisgen, R. et al., "Diphenyl-nitrilimin und seine 1,3-dipolaren additionen an alkene und alkine." Tetrahedron (1962), vol. 17, pp. 3-29. (in German with English abstract).
Inaba, M. et al., "Reversal of multidrug resistance by non antitumor anthracycline analogs." Gann (1984), vol. 75, pp. 1049-1052.
Ingram, V.M. "Sequence Methods." Meth. Enzymol. (1963), vol. 6, pp. 831-848.
Ikeda, T. et al., "Anti-allergic and anti-inflammatory actions of 2'-(tetrazole-5-yl) 4-hydroxy-2-methyl-2H-1,2-benzothiazine 1,1-dioxide." Bioorg. Med. Chem. Lett. (1992), vol. 2, pp. 709-714.

(56) References Cited

OTHER PUBLICATIONS

Jeng, A.Y. et al., "Phosphorylation of ras oncogene product by protein kinase C." Biochem. Biophys. Res. Commun. (1987), vol. 145, pp. 782-788.

Jenkins, F.J. et al., "Effect of ribavirin on Rous sarcoma virus transformation." Antimicrob. Agents Chemother. (1981), vol. 19, pp. 364-368.

Jung-Testas, I. et al., "Effects of steroid hormones and antihormones in cultured cells." Exp. Clin. Endocrinol. (1985), vol. 86, pp. 151-164.

Kahana, C. et al., "Isolation of cloned cDNA encoding mammalian ornithine decarboxylase." Proc. Natl. Acad. Sci. USA(1984), vol. 81, pp. 3645-3649.

Kahana, C. et al., "Nucleotide sequence of murine ornithine decarboxylase mRNA." Proc. Natl. Acad. Sci. USA(1985), vol. 82, pp. 1673-1677.

Kajikawa, N. et al., "Ca2+ dependent neutral protease and proteolytic activation of Ca2+ activated, phospholipid dependent protein kinase." Methods. Enzymol. (1983), vol. 102, pp. 279-290.

Kamata, N. et al., "Growth inhibitory effects of epidermal growth factor and overexpression of its receptors on human squamous cell carcinomas in culture." Cancer Res. (1986), vol. 46, pp. 1648-1653.

Kartner, N. et al., "Cell surface P glycoprotein associated with multidrug resistance in mammalian cell lines." Science (1983), vol. 221, pp. 1285-1288.

Kartner, N. et al., "Detection of P glycoprotein in multidrug resistant cell lines by monoclonal antibodies." Nature (1985), vol. 316(6031), pp. 820-823.

Kavanagh, T.J. et al., "Characterization of a human teratocarcinoma cell assay for inhibitors of metabolic cooperation." Cancer Res. (1986), vol. 46, pp. 1359-1366.

Kikkawa, U. et al., "Protein Kinase C and the Mechanism of Action of Tumor Promoters." In Levine, A.J. et al. (Eds), Cancer Cells 1: The Transformed Phenotype, pp. 239-244. (Cold Spring Harbor Laboratory, Cold Spring Harbor, N.Y. 1984).

Kirstein et al. "Tumor necrosis factor stimulates proliferation of human gastrosarcoma cells and transcription of Myc messenger RNA." UCLA Symposia on Molecular & Cellular Biology Abstract D 209, Jan. 17-Jan. 30, 1988.

Klatzmann, D. et al., "HIV infection: facts and hypotheses." Immunol. Today (1986), vol. 7, pp. 291-296.

Klatzmann, D. et al., "T lymphocyte T4 molecule behaves as the receptor for human retrovirus LAV." Nature (1984), vol. 312(5996), pp. 767-768.

Knowles, P.P. et al., "Purification of immunotoxins containing ricin A chain and abrin A chain using blue sepharose CL 6B." Anal. Biochem. (1987), vol. 160, pp. 440-443.

Koenig, S. et al., "Detection of AIDS virus in macrophages in brain tissue from AIDS patients with encephalopathy." Science (1986), vol. 233(4768), pp. 1089-1093.

Kohler, G. et al., "Derivation of specific antibody producing tissue culture and tumor lines by cell fusion." Eur. J. Immunol. (1976), vol. 6, pp. 511-519.

Koprowski, H. et al., "Human anti idiotype antibodies in cancer patients: Is the modulation of the immune response beneficial for the patient?" Proc. Natl. Acad. Sci. USA (1984), vol. 81, pp. 216-219.

Kraft, A.S. et al., "Overexpression of protein kinase C beta 1 is not sufficient to induce factor independence in the interleukin-3-dependent myeloid cell line FDC-P1." Oncogene (1990), vol. 5(8), pp. 1243-1246.

Krauss, R.S. et al., "Disturbances in growth control and gene expression in a C3H/10T1/2 cell line that stably overproduces protein kinase C." Oncogene (1989), vol. 4, pp. 991-998.

Kronke, M. et al., "Adult T cell leukemia: a potential target for ricin A chain immunotoxins." Blood (1985), vol. 65, pp. 1416-1421.

Kronke, M. et al., "Selective killing of human T lymphotropic virus I infected leukemic T cells by monoclonal anti interleukin 2 receptor antibody ricin A chain conjugates: potentiation by ammonium chloride and monensin." Cancer Res. (1986), vol. 46, pp. 3295-3298.

Kuczek, T. et al., "Tumor cell heterogeneity: divided colony assay for measuring drug response." Proc. Natl. Acad. Sci. USA (1987), vol. 84, pp. 4490-4494.

Kuwano, M. et al., "Techniques to reverse or circumvent drug resistance in vitro." Prog. Clin. Biol. Res. (1986), vol. 223, pp. 163-171.

Lane, H.C. et al., "Qualitative analysis of immune function in patients with the acquired immunodeficiency syndrome. Evidence for a selective defect in soluble antigen recognition." N. Engl. J. Med. (1985), vol. 313, pp. 79-84.

Lane, H.C. et al., "Abnormalities of B cell activation and immunoregulation in patients with the acquired immunodeficiency syndrome." N. Engl. J. Med. (1983), vol. 309, pp. 453-458.

Langer, R. "Controlled release of macromolecules." Chemtech (1982), vol. 12, pp. 98-105.

Lasky, L.A. et al., "Neutralization of the AIDS retrovirus by antibodies to a recombinant envelope glycoprotein." Science (1986), vol. 233(4760), pp. 209-212.

Lerner, R.A. "Tapping the immunological repertoire to produce antibodies of predetermined specificity." Nature (1982), vol. 299(5884), pp. 592-596.

Lester, H.A., "Heterologous expression of excitability proteins: route to more specific drugs?" Science(1988), vol. 241(4869), pp. 1057-1063.

Levy, J.A. et al., "AIDS associated retroviruses (ARV) can productively infect other cells besides human T helper cells." Virology (1985), vol. 147, pp. 441-448.

Lombardino, J.G. et al., "Synthesis and antiinflammatory activity of some 3-carboxamides of 2-alkyl-4-hydroxy-2H-1,2-benzothiazine 1,1-dioxide." J. Med. Chem. (1971), vol. 14, pp. 1171-1175.

Lombardino, J.G. et al., "Antiinflammatory 3,4-dihydro-2-alkyl-3-oxo-2H-1,2-benzothiazine-4-carboxamide-1,1-dioxides." J. Med. Chem. (1971), vol. 14, pp. 973-977.

Lombardino, J.G. et al., "Preparation and antiinflammatory activity of some nonacidic trisubstituted imidazoles." J. Med. Chem. (1974), vol. 17, pp. 1182-1188.

Lombardino, J.G. et al., "New synthetic approaches to 3-carboxamides of 4-hydroxy-2H-1,2-benzothiazine 1,1-dioxide." J. Heterocyclic. Chem. (1976), vol. 13, pp. 333-335.

Lombardino, J.G., "Synthesis and antiinflammatory activity of metabolites of piroxicam." J. Med. Chem. (1981), vol. 24, pp. 39-42.

Long, S.D. et al., "Protease inhibitor antipain suppresses 12 O tetradecanoyl phorbol 13 acetate induction of plasminogen activator in transformable mouse embryo fibroblasts." Carcinogenesis (1981), vol. 2, pp. 933-936.

Lyerly, H.K. et al., "Human T cell lymphotropic virus IIIB glycoprotein (gp120) bound to CD4 determinants on normal lymphocytes and expressed by infected cells serves as target for immune attack." Proc. Natl. Acad. Sci. USA (1987), vol. 84, pp. 4601-4605.

MacLeod, C.L. et al., "EGF induces cell cycle arrest of A431 human epidermoid carcinoma cells." J. Cell. Physiol. (1986), vol. 127, pp. 175-182.

Maier, P. et al., "A two parameter flow cytometry protocol for the detection and characterization of the clastogenic, cytostatic and cytotoxic activities of chemicals." Mutat. Res. (1986), vol. 164, pp. 369-379.

Matthews, J.T. et al., "12-O-tetradecanoylphorbol-13-acetate stimulates phosphorylation of the 58,000-Mr form of polyomavirus middle T antigen in vivo: implications for a possible role of protein kinase C in middle T function." J. Virol. (1986), vol. 58(2), pp. 239-246.

McDougal, J.S. et al., "Binding of HTLV III/LAV to T4+ T cells by a complex of the 110K viral protein and the T4 molecule." Science (1986), vol. 231(4736), pp. 382-385.

McDougal, J.S. et al, "Binding of the human retrovirus HTLV III/LAV/ARV/HIV to the CD4 (T4) molecule: conformation dependence, epitope mapping, antibody inhibition, and potential for idiotypic mimicry." J. Immunol. (1986), vol. 137, pp. 2937-2944.

Mehra, V. et al., "Efficient mapping of protein antigenic determinants." Proc. Natl. Acad. Sci. USA(1986), vol. 83, pp. 7013-7017.

Modrow, S. et al., "Computer assisted analysis of envelope protein sequences of seven human immunodeficiency virus isolates: pre-

(56) References Cited

OTHER PUBLICATIONS diction of antigenic epitopes in conserved and variable regions." J. Virol. (1987), vol. 61, pp. 570-578.
Moolten, F.L., "Tumor chemosensitivity conferred by inserted herpes thymidine kinase genes: paradigm for a prospective cancer control strategy." Cancer Res. (1986), vol. 46, pp. 5276-5281.
Morrison, S.L. et al., "Chimeric human antibody molecules: mouse antigen binding domains with human constant region domains." Proc. Natl. Acad. Sci. USA (1984), vol. 81, pp. 6851-6855.
Mougneau, E. et al., "Biological activities of v myc and rearranged c myc oncogenes in rat fibroblast cells in culture." Proc. Natl. Acad. Sci. USA (1984), vol. 81, pp. 5758-5762.
Murphy, L.C. et al., "Differential effects of tamoxifen and analogs with nonbasic side chains on cell proliferation in vitro." Endocrinology (1984), vol. 116, pp. 1071-1078.
Murray, H.W. et al., "Impaired production of lymphokines and immune (gamma) interferon in the acquired immunodeficiency syndrome." N. Engl. J. Med. (1984), vol. 310(14), pp. 883-889.
Mutschler, E., Effects of Pharmaceutical Preparations (1975) pp. 231-235. (with translation).
Nakadate, T. et al., "Inhibition of 12 O tetradecanoylphorbol 13 acetate induced tumor promotion and epidermal ornithine decarboxylase activity in mouse skin by palmitoylcarnitine." Cancer Res. (1986), vol. 46, pp. 1589-1593.
Nakamura, G.R. et al., "Monoclonal Antibodies to the Extracellular Domain of HIV-1IIIB gp160 that Neutralize Infectivity, Block Binding to CD4, and React with Diverse Isolates." AIDS Res. and Human Retroviruses (1992), vol. 8(11), pp. 1875-1885.
Nepom, G.T. et al., "Induction of immunity to a human tumor marker by in vivo administration of anti idiotypic antibodies in mice." Proc. Natl. Acad. Sci. USA (1984), vol. 81, pp. 2864-2867.
Neuberger, M.S. et al., "Recombinant antibodies possessing novel effector functions." Nature (1984), vol. 312(5995), pp. 604-608.
Noda, M. et al., "Expression of functional sodium channels from cloned cDNA." Nature (1986), vol. 322, pp. 826-828.
Noguchi, S. et al., "Expression of functional (Na+ + K+)-ATPase from cloned cDNAs." FEBS Lett. (1987), vol. 225, pp. 27-32.
O'Brian, C.A. et al., "Current concepts of tumor promotion by phorbol esters and related compounds." In: New Insights into Cell and Membrane Transport Processes (1986) (Poste, G. and Crooke, S. T., eds., Plenum Publishing Co., New York, NY) pp. 261-274.
Oi, V.T. et al., "Immunoglobulin-producing hybrid cell lines." In: Selected Methods in Cellular Immunology (Mishell, B.B. And Shiigi, S.M., eds., W.H. Freeman & Co., San Francisco, CA), (1980) pp. 351-372.
Ogawara, H. et al., "A specific inhibitor for tyrosine protein kinase from Pseudomonas." J. Antibiot. (1986) (Tokyo), vol. 39, pp. 606-608.
Pastan, et al. "Multidrug resistance." UCLA Symposia on Molecular & Cellular Biology Abstract A13, Jan. 1986.
Perez, P. et al., "Specific targeting of cytotoxic T cells by anti T3 linked to anti target cell antibody." Nature(1985), vol. 316(6026), pp. 354-356.
Popovic, M. et al., "Detection, isolation, and continuous production of cytopathic retroviruses (HTLV III) from patients with AIDS and pre AIDS." Science (1984), vol. 224(4648), pp. 497-500.
Putney, S.D. et al., "HTLV III/LAV neutralizing antibodies to an *E. coli* produced fragment of the virus envelope." Science (1986), vol. 234(4782), pp. 1392-1395.
Rahaingoson, F. et al., "On epot synthesis of furyl α-bromoketones from furyl ketones using the A-162 Br3-resin/CH3NO2 system." Synth. Comm. (1992), vol. 22, pp. 1923-1927.
Ratner, L. et al., "Complete nucleotide sequence of the AIDS virus, HTLV III." Nature (1985), vol. 313(6000), pp. 277-284.
Reddel, R.R. et al., "Differential sensitivity of human breast cancer cell lines to the growth inhibitory effects of tamoxifen." Cancer Res. (1985) , vol. 45, pp. 1525-1531.
Reddy, E.P. et al., "Complete nucleotide sequence and organization of the Moloney murine sarcoma virus genome." Science (1981), vol. 214(4519), pp. 445-450.

Reinecke, M.G. et al., "An improved synthesis of thiophene-2,3-dicarboxylic acid by sequential carboxylation." Synthesis (Apr. 1980), pp. 327-329.
Richert, N. et al., "Inhibition of the transformation specific kinase in ASV transformed cells by N alpha tosyl L lysyl chloromethyl ketone." Cell (1979), vol. 18, pp. 369-374.
Rizzino, A. et al., "Induction and modulation of anchorage independent growth by platelet derived growth factor, fibroblast growth factor, and transforming growth factor beta." Cancer Res. (1986), vol. 46, pp. 2816-2820.
Roberts, A.B. et al., "Selective inhibition of the anchorage independent growth of myc transfected fibroblasts by retinoic acid." Nature (1985), vol. 315(6016), pp. 237-239.
Robey, W.G. et al., "Prospect for prevention of human immunodeficiency virus infection: purified 120 kDa envelope glycoprotein induces neutralizing antibody." Proc. Natl. Acad. Sci. USA (1986), vol. 83, pp. 7023-7027.
Rook, A.H. et al., "Interleukin 2 enhances the depressed natural killer and cytomegalovirus specific cytotoxic activities of lymphocytes from patients with the acquired immune deficiency syndrome." J. Clin. Invest. (1983), vol. 72, pp. 398-403.
Roy, S.K. et al., "High performance immunosorbent purification of recombinant leukocyte A interferon" J. Chromatogr. (1984), vol. 303, pp. 225-228.
Sandstrom, E.G. et al., "Inhibition of human T-cell lymphotropic virus type III in vitro by phosphonoformate." Lancet (1985), vol. 1(8444), pp. 1480-1482.
Sarngadharan, M.G. et al., "Antibodies reactive with human T lymphotropic retroviruses (HTLV III) in the serum of patients with AIDS." Science (1984), vol. 224(4648), pp. 506-508.
Schaeffer, W.I. et al., "Efficient detection of soft agar grown colonies using a tetrazolium salt." Cancer Lett. (1976), vol. 1, pp. 259-262.
Schleicher, R.L. et al., "Inhibition of hamster melanoma growth by estrogen." Cancer Res. (1987), vol. 47, pp. 453-459.
Schupbach, J. et al., "Serological analysis of a subgroup of human T lymphotropic retroviruses (HTLV III) associated with AIDS." Science (1984), vol. 224(4648), pp. 503-505.
Schweigerer, L. et al., "Capillary endothelial cells express basic fibroblast growth factor, a mitogen that promotes their own growth." Nature (1987), vol. 325(6101), pp. 257-259.
Senga, T. et al., "Clustered cysteine residues in the kinase domain of v-Src: critical role for protein stability, cell transformation and sensitivity to herbimycin A." Oncogene (2000), vol. 19(2), pp. 273-279.
Shalaby, M.R. et al., "The effects of human immunodeficiency virus recombinant envelope glycoprotein on immune cell functions in vitro." Cell. Immunol. (1987), vol. 110, pp. 140-148.
Sidman, K.R. et al., "Controlled release of macromolecules and pharmaceuticals from synthetic polypeptides based on glutamic acid." Biopolymers (1983), vol. 22(1), pp. 547-556.
Siegel, J.P. et al., "Sera from patients with the acquired immunodeficiency syndrome inhibit production of interleukin 2 by normal lymphocytes." J. Clin. Invest. (1985), vol. 75, pp. 1957-1964.
Sistonen, L. et al., "Dose effects of transfected c Ha rasVal 12 oncogene in transformed cell clones." Exp. Cell Res. (1987), vol. 168, pp. 518-530.
Skovsgaard, T. et al., "Chemosensitizers counteracting acquired resistance to anthracyclines and vinca alkaloids in vivo. A new treatment principle." Cancer Treat. (1984), Rev. 11 Suppl A:63-72.
Smith, D.H. et al., "Blocking of HIV 1 infectivity by a soluble, secreted form of the CD4 antigen." Science (1987), vol. 238(4834), pp. 1704-1707.
Stabel, S. et al. "Protein kinase C—structural and functional characterization." In: Journal of Cellular Biochemistry, Supplement 10C: UCLA Symposia on Molecular & Cellular Biology, (1986) Abstract L318, Alan R. Liss, Inc., New York, p. 206.
Stahl, R.E. et al., "Immunologic abnormalities in homosexual men. Relationship to Kaposi's sarcoma." Am. J. Med. (1982), vol. 73(2), pp. 171-178.
Steinkamp, J.A. et al., "Phagocytosis: flow cytometric quantitation with fluorescent microspheres." Science (1982) , vol. 215(4528), pp. 64-66.

(56) References Cited

OTHER PUBLICATIONS

Storer, R.D. et al., "Malignant transformation of a preneoplastic hamster epidermal cell line by the Ej c Ha ras oncogene." Cancer Res. (1986), vol. 46, pp. 1458-1464.
Sullivan, L.M. et al., "An anticatalytic monoclonal antibody to avian plasminogen activator: its effect on behavior of RSV transformed chick fibroblasts." Cell (1986), vol. 45, pp. 905-915.
Tagliaferri, P. et al., "Effects of ouabain on NIH/3T3 cells transformed with retroviral oncogenes and on human tumor cell lines." Int. J. Cancer (1987), vol. 40, pp. 653-658.
Takeda, S. et al., "Construction of chimaeric processed immunoglobulin genes containing mouse variable and human constant region sequences." Nature (1985), vol. 314(6010), pp. 452-454.
Tanaka, K. et al, "Pharmacological studies of the new antiinflammatory agent 3 formylamino-7 methylsulfonylamino 6 phenoxy 4' 1 benzopyran 4 one. 2nd communication: effect on the arachidonic acid cascades." Arzneimittelforschung (1992), vol. 42, pp. 945-950.
Tanaka, A. et al., "Antiplatelet agents based on cyclooxygenase inhibition without ulcerogenesis. Evaluation and synthesis of 4,5 bis(4 methoxyphenyl) 2 substituted thiazoles." J. Med. Chem. (1994), vol. 37, pp. 1189-1199.
Thalacker, F.W. et al., "Specific induction of secreted proteins by transforming growth factor beta and 12 O tetradecanoylphorbol 13 acetate. Relationship with an inhibitor of plasminogen activator." J. Biol. Chem. (1987), vol. 262, pp. 2283-2290.
Thorpe, P.E. et al., "Modification of the carbohydrate in ricin with metaperiodate cyanoborohydride mixtures. Effects on toxicity and in vivo distribution." Eur. J. Biochem. (1985), vol. 147, pp. 197-206.
Tseng et al., Prevention of anchorage independent colony growth of inducible EJ ras oncogene transfected RAT 1 fibroblasts by drugs that interact with the poly (ADP ribose) polymerase system. (1986) Abstract. Clin Res (1986). vol. 34(1).
Tsuruo, T. et al., "Enhancement of vincristine and adriamycin induced cytotoxicity by verapamil in P388 leukemia and its sublines resistant to vincristine and adriamycin." Biochem. Pharmacol. (1982), vol. pp. 31, pp. 3138-3140.
Uehara, Y. et al., "Specific increase in thymidine transport at a permissive temperature in the rat kidney cells infected with srcts Rous sarcoma virus." Biochem. Biophys. Res. Commun. (1984), vol. 125, pp. 129-134.
Uehara, Y. et al., "Differential sensitivity of RSVts (temperature sensitive Rous sarcoma virus) infected rat kidney cells to nucleoside antibiotics at permissive and non permissive temperatures." Biochem. J. (1985), vol. 232, pp. 825-831.
Uehara, Y. et al., "Increased sensitivity to oxanosine, a novel nucleoside antibiotic, of rat kidney cells upon expression of the integrated viral src gene." Cancer Res. (1985), vol. 45, pp. 5230-5234.
Uehara, Y. et al., "Morphological changes from 'transformed' to 'normal' by benzoquinoid ansamycins accompany the inhibition of pp60src in rat kidney cells infected with srcts-Rous Sarcoma Virus." Recent Adv. Chemother., Proc. Int. Congr. Chemother., 14th, vol. Anticancer Sect. 1 (Ishigami, Joji, ed., Univ. Tokyo, 1985), pp. 219-220.
Uehara, Y. et al., "Mechanism of reversion of Rous sarcoma virus transformation by herbimycin A: reduction of total phosphotyrosine levels due to reduced kinase activity and increased turnover of p60v src1." Cancer Res. (1989), vol. 49, pp. 780-785.
Uehara, Y. et al., "Use and selectivity of herbimycin A as inhibitor of protein-tyrosine kinases." Methods Enzymol. (1991), vol. 201:370-9.
Vane, J. "Towards a better aspirin." Nature (1994), vol. 367(6460), pp. 215-216.
Verma, A.K. et al, "Involvement of protein kinase C activation in ornithine decarboxylase gene expression in primary culture of newborn mouse epidermal cells and in skin tumor promotion by 12 O tetradecanoylphorbol 13 acetate." Cancer Res. (1986) vol. 46, pp. 6149-6155.
Vilmer, E. et al., "Isolation of new lymphotropic retrovirus from two siblings with haemophilia B, one with AIDS." Lancet (1984), vol. 1(8380), pp. 753-757.
Vitetta, E.S. et al., "Redesigning nature's poisons to create anti tumor reagents." Science (1987), vol. 238(4830), pp. 1098-1104.
Walton, G.M. et al., "A three step purification procedure for protein kinase C: characterization of the purified enzyme." Anal. Biochem. (1987), vol. 161, pp. 425-437.
Weinstein, I.B. et al., "Initial cellular targets and eventual genomic changes in multistage carcinogenesis." In: Models, Mechanisms and Etiology of Tumour Promotion (Borzsonyi, M., Lapis, K., Day, N.E., Yamasaki, H. eds., International Agency for Research on Cancer, Lyon, France, 1984) pp. 277-297.
Weinstein, I.B. et al., "Multistage carcinogenesis involves multiple genes and multiple mechanisms." J. Cell. Physiol. (1984), Suppl. 3, pp. 127-137.
Weinstein, I.B. et al., "Molecular mechanisms in multistage chemical carcinogenesis." In: Biochemical Basis of Carcinogenesis (Greim, H., Jung, R., Kramer, M., Marquardt, H., Oesch, F. eds., Raven Press, New York, NY 1984) pp. 193-212.
Weltman, J.K. et al., "Rapid screening with indirect immunotoxin for monoclonal antibodies against human small cell lung cancer." Cancer Res. (1987), vol. 47, pp. 5552-5556.
Willey, J.C. et al., "Relationship of ornithine decarboxylase activity and cAMP metabolism to proliferation of normal human bronchial epithelial cells." J. Cell. Physiol. (1985), vol. 124, pp. 207-212.
Wood, P.A. et al., "Expression of human argininosuccinate synthetase after retroviral mediated gene transfer." Somat. Cell Mol. Genet. (1986), vol. 12, pp. 493-500.
Work, T.S. et al., Work E., Laboratory Techniques in Biochemistry and Molecular Biology, Elsevier Biomedical Press (1982).
Young, R.A. et al, "Dissection of *Mycobacterium tuberculosis* antigens using recombinant DNA." Proc. Natl. Acad. Sci. USA. (1985), vol. 82(9), pp. 2583-2587.
Young, S. et al., "Down regulation of protein kinase C is due to an increased rate of degradation." Biochem. J. (1987), vol. 244, pp. 775-779.
Yoshikawa, M. et al., "Analysis of proteolytic processing during specific antigen presentation." Cell. Immunol. (1987), vol. 110, pp. 431-435.

THERAMUTEIN MODULATORS

CROSS REFERENCE TO RELATED APPLICATIONS

This application is a divisional of U.S. patent application Ser. No. 15/399,543, filed on Jan. 5, 2017; which is a divisional of U.S. patent application Ser. No. 14/297,863, filed on Jun. 6, 2014, now U.S. Pat. No. 9,579,326, issued on Feb. 28, 2017; which is a continuation of U.S. patent application Ser. No. 13/758,422, filed on Feb. 4, 2013; which is a continuation of U.S. patent application Ser. No. 10/569,315, filed on Apr. 28, 2008, now U.S. Pat. No. 8,367,038, issued on Feb. 5, 2013; which is the U.S. National Phase of International Application No. PCT/US05/18412, filed on May 23, 2005; and claims priority to U.S. Provisional Application No. 60/633,013, filed on Dec. 3, 2004, and U.S. Provisional Application No. 60/573,962, filed on May 23, 2004, the contents of which applications are incorporated by reference herein.

BACKGROUND OF THE INVENTION

The progressive development of drug resistance in a patient is the hallmark of chronic treatment with many classes of drugs, especially in the therapeutic areas of cancer and infectious diseases. Molecular mechanisms have been identified which mediate certain types of drug resistance phenomena, whereas in other cases the mechanisms of acquired as well as de novo resistance remain unknown today.

One mechanism of induced (acquired) drug resistance originally thought to be relevant in the area of cancer therapy involves increased expression of a protein known as P-glycoprotein (P-gp). P-gp is located in the cell membrane and functions as a drug efflux pump. The protein is capable of pumping toxic chemical agents, including many classical anti-cancer drugs, out of the cell. Consequently, upregulation of P-glycoprotein usually results in resistance to multiple drugs. Upregulation of P-glycoprotein in tumor cells may represent a defense mechanism which has evolved in mammalian cells to prevent damage from toxic chemical agents. Other related drug resistance proteins have now been identified with similar functions to P-gp, including multi-drug-resistance-associated protein family members such as MRP1 and ABCG2. In any event, with the advent of the development of compounds that are specific for a given target protein, and less toxic, the importance of P-glycoprotein and related ATP-binding cassette (ABC) transporter proteins in clinically significant drug resistance has lessened.

Another possible molecular mechanism of acquired drug resistance is that alternative signal pathways are responsible for continued survival and metabolism of cells, even though the original drug is still effective against its target. Furthermore, alterations in intracellular metabolism of the drug can lead to loss of therapeutic efficacy as well. In addition, changes in gene expression as well as gene amplification events can occur, resulting in increased or decreased expression of a given target protein, and frequently requiring increasing dosages of the drug to maintain the same effects. (Adcock and Lane, 2003)

Mutation induced drug resistance is a frequently occurring event in the infectious disease area. For example, several drugs have been developed that inhibit either the viral reverse transcriptase or the viral protease encoded in the human immunodeficiency (HIV) viral genome. It is well established in the literature that repeated treatment of HIV-infected AIDS patients using, for example, a reverse transcriptase inhibitor eventually gives rise to mutant forms of the virus that have reduced sensitivity to the drug which resulted from mutations that have occurred in the gene encoding reverse transcriptase that render the mutant form of the enzyme less affected by the drug.

The appearance of drug resistance during the course of HIV treatment is not surprising considering the rate at which errors are introduced into the HIV genome. The HIV reverse transcriptase enzyme is known to be particularly error prone, with a forward mutation rate of about $3.4 \times 10^{-5}$ mutations per base pair per replication cycle (Mansky et al., *J. Virol.* 69:5087-94 (1995)). However, analogous mutation rates for endogenous genes encoded in mammalian cells are more than an order of magnitude lower.

New evidence shows that drug resistance can also arise from a mutational event involving the gene encoding the drug target (Gorre et al., Science, 2001; PCT/US02/18729). In this case, exposure of the patient to a specific therapeutic substance such as a given cancer drug that targets a specific protein-of-interest (POI, or "target" protein) may be followed by the outgrowth of a group of cells harboring a mutation occurring in the gene encoding the protein that is the target of the therapeutic substance. Whether the outgrowth of this population of cells results from a small percentage of pre-existing cells in the patient which already harbor a mutation which gives rise to a drug-resistant POI, or whether such mutations arise de novo during or following exposure of the animal or human being to a therapeutic agent capable of activating or inhibiting said POI, is presently unknown. In either case, such mutation events may result in a mutated protein (defined below as a theramutein) which is less affected, or perhaps completely unaffected, by said therapeutic substance.

Chronic myelogenous leukemia (CML) is characterized by excess proliferation of myeloid progenitors that retain the capacity for differentiation during the stable or chronic phase of the disease. Multiple lines of evidence have established deregulation of the Abl tyrosine kinase as the causative oncogene in certain forms of CML. The deregulation is commonly associated with a chromosomal translocation known as the Philadelphia chromosome (Ph), which results in expression of a fusion protein comprised of the BCR gene product fused to the Abelson tyrosine kinase, thus forming $p210^{Bcr-Abl}$ which has tyrosine kinase activity. A related fusion protein, termed $p190^{Bcr-Abl}$ that arises from a different breakpoint in the BCR gene, and has been shown to occur in patients with Philadelphia chromosome positive (Ph+) Acute Lymphoblastic Leukemia (ALL) (Melo, 1994; Ravandi et al., 1999). Transformation appears to result from activation of multiple signal pathways including those involving RAS, MYC, and JUN. Imatinib mesylate ("STI-571" or "Gleevec®") is a 2-phenylamino pyrimidine that targets the ATP binding site of the kinase domain of Abl (Druker et al, NEJM 2001, p. 1038). Subsequently it has also been found by other methods to be an inhibitor of platelet-derived growth factor (PDGF) β receptor, and the Kit tyrosine kinase, the latter of which is involved in the development of gastrointestinal stromal tumors (see below).

Until recently, it had not been observed that during the course of treatment with a specific inhibitor of a given endogenous cellular protein that a mutation in its corresponding endogenous gene could lead to the expression of protein variants whose cellular functioning was resistant to the inhibitor. Work by Charles Sawyers and colleagues (Gorre et al., Science 293:876-80 (2001); PCT/US02/18729)

demonstrated for the first time that treatment of a patient with a drug capable of inhibiting the p210$^{Bcr\text{-}Abl}$ tyrosine kinase (i.e., STI-571) could be followed by the emergence of a clinically significant population of cells within said patient harboring a mutation in the gene encoding the p210$^{Bcr\text{-}Abl}$ cancer causing target protein which contains the Abelson tyrosine kinase domain. Various such mutations gave rise to mutant forms of p210$^{Bcr\text{-}Abl}$ which were less responsive to Gleevec treatment than was the original cancer causing version. Notably, the mutations that emerged conferred upon the mutant protein a relative resistance to the effects of the protein kinase inhibitor drug, while maintaining a certain degree of the original substrate specificity of the mutant protein kinase. Prior to Gorre et al.'s work, it was generally believed by those skilled in the art that the types of resistance that would be observed in patients exposed to a compound which inhibited the Abelson protein kinase, such as STI-571, would have resulted from one or more of the other mechanisms of drug resistance listed above, or by some other as yet unknown mechanism, but that in any event said resistance would involve a target (protein or otherwise) which was distinct from the drug's target POI.

Accordingly, the ability to treat clinically relevant resistant mutant forms of proteins that are otherwise the targets of an existing therapy would be extremely useful. Such mutated proteins (theramuteins as defined below) are beginning to be recognized and understood to be important targets in recurring cancers, and will become important in other diseases as well. There exists a need for therapeutic agents that are active against such drug resistant variant forms of cellular proteins that may arise before, during or following normally effective drug therapies. A key purpose of this invention is to provide compounds that may serve as potential therapeutic agents useful in overcoming mutation-induced drug resistance in endogenously occurring proteins.

BRIEF SUMMARY OF THE INVENTION

This invention relates to agents that are inhibitors or activators of variant forms of endogenous proteins and novel methods of identifying such variants. Of particular interest are inhibitors and activators of endogenous protein variants, encoded by genes which have mutated, which variants often arise or are at least first identified as having arisen following exposure to a chemical agent which is known to be an inhibitor or activator of the corresponding unmutated endogenous protein. Such protein variants (mutant proteins) are herein termed "theramuteins," may occur either spontaneously in an organism (and be pre-existing mutations in some cases), or said mutants may arise as a result of selective pressure which results when the organism is treated with a given chemical agent capable of inhibiting the non-mutated form of said theramutein (herein termed a "prototheramutein"). It will be understood that in some cases a prototheramutein may be a "wild type" form of a POI (e.g., a protein that gives rise to a disease due to disregulation). In other cases, the prototheramutein will be a disease causing variant of a "wild type" protein, having already mutated and thereby contributing to the development of the diseased state as a result of said prior mutation. One example of the latter type of prototheramutein is the P210$^{BCR\text{-}ABL}$ oncoprotein, and a mutant form of this protein harboring a threonine (T) to isoleucine (I) mutation at position 315 is termed P210$^{BCR\text{-}ABL\text{-}T315I}$ and is one example of a theramutein. As used herein, the designation "P210$^{BCR\text{-}ABL}$" is synonymous with the term "p210$^{Bcr\text{-}Abl}$", the "wild-type Bcr-Abl protein", and the like.

Theramuteins are a rare class of endogenous proteins that harbor mutations that render said proteins resistant to drugs that are known to inhibit or activate in a therapeutically effective manner their non-mutated counterparts. The endogenous genes encoding a few such proteins are presently known to exhibit such mutations under certain circumstances. This Invention is directed toward compositions that inhibit certain drug-resistant mutants (theramuteins) of the Abelson tyrosine kinase protein, originally termed P210-Bcr-Abl in the literature, that is involved in the development of chronic myelogenous leukemia. The invention is also directed toward general methods of identifying compounds that inhibit or activate any theramutein.

The present method is particularly directed toward the identification of specific inhibitors or specific activators of theramuteins. Use of the term "specific" in the context of the terms "inhibitor" or "activator" (see definitions below) means that said inhibitor or activator binds to the theramutein and inhibits or activates the cellular functioning of the theramutein without also binding to and activating or inhibiting a wide variety of other proteins or non-protein targets in the cell. The skilled investigator is well aware that there is a certain degree of variability in the medical literature with respect to the concept of a specific inhibitor or a specific activator, and of the related concept of target protein "specificity" when discussing the actions of inhibitors or activators of a protein. Accordingly, for the purposes of this Invention, a substance is a specific inhibitor or a specific activator of a given theramutein if said substance is capable of inhibiting or activating said theramutein at a given concentration such that a corresponding phenoresponse is modulated in the appropriate manner, without having an appreciable effect at the same given concentration upon the phenoresponse of a corresponding control cell that essentially does not express either the theramutein or its corresponding prototheramutein.

In certain embodiments, a substance may be a modulator of the prototheramutein as well as the theramutein. In other embodiments, in addition to being a modulator of the prototheramutein and theramutein, a substance may also modulate the activities of proteins that have similar functions. As discussed above, in addition to inhibiting the p210$^{Bcr\text{-}Abl}$ tyrosine kinase, imatinib mesylate is also capable of inhibiting the c-kit oncogene product (also a tyrosine kinase) which is overexpressed in certain gastrointestinal stromal tumors, as well as the PDGF β receptor (also a tyrosine kinase), which is expressed in certain chronic myelomonocytic leukemias (CMML). Such a compound is sometimes termed a "moderately specific" inhibitor.

The invention also provides a general method that can be used to identify substances that will activate or inhibit a theramutein, to the same extent, and preferably to an even greater extent than a known drug substance is capable of inhibiting the corresponding "wild type" form of that protein. (The skilled artisan is well aware, however, that said "wild type" forms of such proteins may have already mutated in the course of giving rise to the corresponding disease in which said protein participates.)

In a preferred embodiment, the present invention provides inhibitors of the P210$^{BCR\text{-}ABL\text{-}T315I}$ theramutein having the formula I

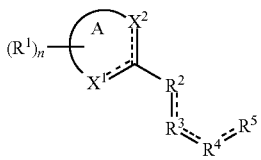

(I)

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
  each $R^{11}$ is independently selected from H, alkyl, cycloalkyl, alkenyl, alkynyl, aralkyl, aryl, and a heterocyclic ring;
  each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
  p is 0 to 4;
  q is 0 to 4;
$R^2$ is selected from —$CR^{21}_a$—, —$NR^{22}_b$—, and —(C=$R^{23}$)—;
  each $R^{21}$ is independently selected from H, halo, —$NH_2$, —N(H)($C_{1-3}$ alkyl), —N($C_{1-3}$ alkyl)$_2$, —O—($C_{1-3}$ alkyl), OH and $C_{1-3}$ alkyl;
  each $R^{22}$ is independently selected from H and $C_{1-3}$ alkyl;
  $R^{23}$ is selected from O, S, N—$R^0$, and N—$OR^0$;
$R^3$ is selected from $CR^{31}_c$—, —$NR^{32}_d$—, and —(C=$R^{33}$)—;
  each $R^{31}$ group is selected from H, halo, —$NH_2$, —N(H)($R^0$), —N($R^0$)$_2$, —O—$R^0$, OH and $C_{1-3}$ alkyl;
  each $R^{32}$ group is selected from H, alkyl, cycloalkyl, alkenyl, alkynyl, aralkyl, $CO_2R^0$, $C(O)R^0$, aryl, and a heterocyclic ring;
  $R^{33}$ is selected from O, S, N—$R^{34}$, and N—$OR^0$;
  $R^{34}$ is selected from H, $NO_2$, CN, alkyl, cycloalkyl, alkenyl, alkynyl, aralkyl, aryl and a heterocyclic ring;
$R^4$ is selected from $CR^{41}_e$—, —$NR^{42}_f$—, —(C=$R^{43}$)—, and —O—;
  each $R^{41}$ is selected from H, alkyl, cycloalkyl, alkenyl, alkynyl, $CO_2R^0$, $C(O)R^0$, aralkyl, aryl, and a heterocyclic ring;
  each $R^{42}$ group is selected from H, alkyl, cycloalkyl, alkenyl, alkynyl, aralkyl, $CO_2R^0$, $C(O)R^0$, aryl, and a heterocyclic ring;
  each $R^{43}$ is selected from O, S, N—$R^0$, and N—$OR^0$;
with the provisos that when $R^2$ is $NR^{22}_b$— and $R^4$ is $NR^{42}_f$—, then $R^3$ is not $NR^{32}_d$—; and that both $R^3$ and $R^4$ are not simultaneously selected from —(C=$R^{33}$)— and —(C=$R^{43}$)—, respectively;

$R^5$ is selected from —Y—$R^6$ and —Z—$R^7$;
Y is selected from a chemical bond, O, $NR^0$,
$R^6$ is selected from alkyl, cycloalkyl, alkenyl, alkynyl, aralkyl, aryl, and a heterocyclic ring;
Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;
$R^7$ is H or is selected from aryl and a heterocyclic ring;
each $R^0$ is independently selected from H, alkyl, cycloalkyl, aralkyl, aryl and a heterocyclic ring;
a is 1 or 2;
b is 0 or 1;
c is 1 or 2;
d is 0 or 1;
e is 1 or 2; and
f is 0 or 1.

The invention provides for a fundamentally new way of treating cancer and other diseases where treatment with an existing drug compound, by whatever mechanism, is followed by identifiable (clinically significant) theramutein-mediated drug resistance, by providing alternative drugs that can be administered as theramuteins arise and are identified as such (Wakai et al., 2004, reports an example wherein a theramutein may arise during the course of an on-going treatment regimen), or preemptively before the outgrowth of clinically significant populations of theramutein expressing cells. Further, where a drug treatment for a particular disease is less effective in a subset of individuals that express a certain theramutein of a protein that the drug targets, the invention enables the tailoring of treatments for those subjects by providing alternative drug substances that will be effective against said theramutein.

1. The invention provides a method of determining whether a chemical agent is at least as effective a modulator of a theramutein in a cell as a known substance is a modulator of a corresponding prototheramutein. One embodiment of the method involves contacting a control cell that expresses the prototheramutein and is capable of exhibiting a responsive phenotypic characteristic (linked to the functioning of the prototheramutein in the cell) with the known modulator of the prototheramutein, contacting a test cell that expresses the theramutein and is also capable of exhibiting the responsive phenotypic characteristic (linked to the functioning of the theramutein in the cell) with the chemical agent, and comparing the response of the treated test cell with the response of the treated control cell; to determine that the chemical agent is at least as effective a modulator of the theramutein as the known substance is a modulator of the prototheramutein. In certain other embodiments, one type of control cell may not express the prototheramutein at all. In other embodiments, the control cell may express about the same amount of the prototheramutein as the test cell expresses of the theramutein. In still other embodiments, the control cell may be capable of exhibiting the responsive phenotypic characteristic to about the same extent as the test cell under certain conditions.

2. Theramuteins of the invention that are of particular interest are those involved in regulatory function, such as enzymes, protein kinases, tyrosine kinases, receptor tyrosine kinases, serine threonine protein kinases, dual specificity protein kinases, proteases, matrix metalloproteinases, phosphatases, cell cycle control proteins, docking proteins such as the IRS family members, cell-surface receptors, G-proteins, ion channels, DNA- and RNA-binding proteins, polymerases, and the like. No limitation is intended on the type of theramutein that may be used in the invention. At the present time, three theramuteins are known: BCR-ABL, c-Kit, and EGFR.

3. Any responsive phenotypic characteristic that can be linked to the presence of the theramutein (or prototheramutein) in the cell can be employed for use in the method, including, for example, growth or culture properties, the phosphorylation state (or other modification) of a substrate of the theramutein, and any type of transient characteristic of the cell, as will be defined and discussed in detail

DETAILED DESCRIPTION OF THE INVENTION

Figure 1:
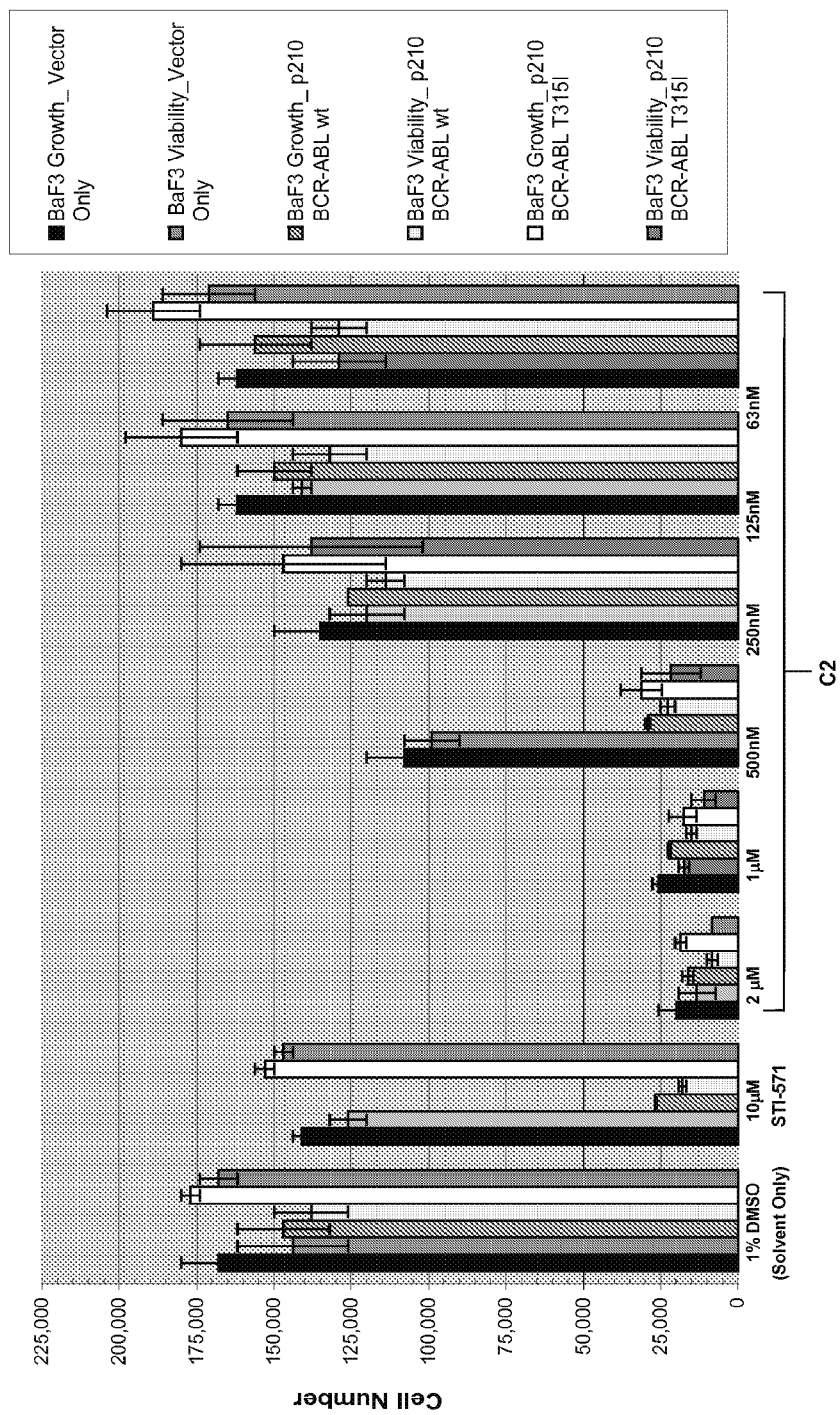
FIG. 1 shows the effect on growth and viability of different concentrations of Compound 2 (C2) for non-transformed vector control Ba/F3 cells (which are IL-3 dependent) as well as Ba/F3 cells expressing the "wild type" $p210^{Bcr-Abl}$ (designated $p210^{Bcr-Abl-wt}$), and Ba/F3 cells expressing the $p210^{Bcr-Abl-T315I}$ drug resistant mutant. Cell counts and viability were determined on an automated cell counter as discussed in detail in the specification. Cell counts are shown by the solid color bars; cell viability is shown by the hashed bars. Note that STI-571 potently inhibits growth of the P210 cell line (grey bar) whereas it is unable to inhibit the growth of the T315I cell line (white bar) even at 10 μM concentration. 500 nM C2 shows the largest specificity gap within this dose-response series. Compare STI-571 at 10 μM to C2 at 500 nM on the T315I cell line (white bars). Abbreviations: DMSO: dimethylsulfoxide (solvent used for drug dissolution).

The term "halo" or "halogen" as used herein includes fluorine, chlorine, bromine and iodine.

The term "alkyl" as used herein contemplates substituted and unsubstituted, straight and branched chain alkyl radicals having from 1 to 6 carbon atoms. Preferred alkyl groups include methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $C(O)NR_2$, $NR_2$, cyclic-amino, $NO_2$, and OR.

The term "cycloalkyl" as used herein contemplates substituted and unsubstituted cyclic alkyl radicals. Preferred cycloalkyl groups are those with a single ring containing 3 to 7 carbon atoms and includes cyclopropyl, cyclopentyl, cyclohexyl, and the like. Other cycloalkyl groups may be selected from $C_7$ to $C_{10}$ bicyclic systems or from $C_9$ to $C_{14}$ tricyclic systems. Additionally, the cycloalkyl group may be optionally substituted with one or more substituents selected from halo, CN, $CO_2R$, C(O)R, $C(O)NR_2$, $NR_2$, cyclic-amino, $NO_2$, and OR.

The term "alkenyl" as used herein contemplates substituted and unsubstituted, straight and branched chain alkene radicals. Preferred alkenyl groups are those containing two to six carbon atoms. Additionally, the alkenyl group may be optionally substituted with one or more substituents selected from halo, CN, $CO_2R$, C(O)R, $C(O)NR_2$, $NR_2$, cyclic-amino, $NO_2$, and OR.

The term "alkynyl" as used herein contemplates substituted and unsubstituted, straight and branched chain alkyne radicals. Preferred alkynyl groups are those containing two to six carbon atoms. Additionally, the alkynyl group may be optionally substituted with one or more substituents selected from halo, CN, $CO_2R$, C(O)R, $C(O)NR_2$, $NR_2$, cyclic-amino, $NO_2$, and OR.

The term "aralkyl" as used herein contemplates an alkyl group which has as a substituent an aromatic group, which aromatic group may be substituted and unsubstituted. The aralkyl group may be optionally substituted on the aryl with one or more substituents selected from halo, CN, $CF_3$, $NR_2$, cyclic-amino, $NO_2$, OR, $CF_3$, —$(CH_2)_xC(O)(CH_2)_yR$, —$(CH_2)_xC(O)N(R')(R'')$, —$(CH_2)_xC(O)O(CH_2)_yR$, —$(CH_2)_xN(R')(R'')$, —$N(R)SO_2R$, —$O(CH_2)_xC(O)N(R')(R'')$, —$SO_2N(R')(R'')$, —$(CH_2)_xN(R)$—$(CH_2)_y$—R, —$(CH_2)_xN(R)$—C(O)—$(CH_2)_y$—R, —$(CH_2)_xN(R)$—C(O)—O—$(CH_2)_y$—R, —$(CH_2)_x$—C(O)—N(R)—$(CH_2)_y$—R, —$(CH_2)_xC(O)N(R)$—$(CH_2)_y$—R, —O—$(CH_2)_x$—C(O)—N(R)—$(CH_2)_y$—R, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one of more halo, CN, $CF_3$, $CO_2R$, C(O)R, $C(O)NR_2$, $NR_2$, cyclic-amino, $NO_2$, and OR.

The term "heterocyclic group" or "heterocyclic ring" as used herein contemplates aromatic and non-aromatic cyclic radicals having at least one heteroatom as a ring member. Preferred heterocyclic groups are those containing 5 or 6 ring atoms which includes at least one hetero atom, and includes cyclic amines such as morpholino, piperidino, pyrrolidino, and the like, and cyclic ethers, such as tetrahydrofuran, tetrahydropyran, and the like. Aromatic heterocyclic groups, also termed "heteroaryl" groups contemplates single-ring hetero-aromatic groups that may include from one to three heteroatoms, for example, pyrrole, furan, thiophene, imidazole, oxazole, thiazole, triazole, pyrazole, pyridine, pyrazine, pyridazine, pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, tetrahydroisoquinoline, quinoxaline, quinaxoline, benzimidazole, benzofuran, purine, imidazopyridine, benzotriazole, and the like. Additionally, the heterocyclic groups may be optionally substituted with halo, CN, $CF_3$, $NR_2$, cyclic-amino, $NO_2$, OR, $CF_3$, —$(CH_2)_xC(O)(CH_2)_yR$, —$(CH_2)_xC(O)N(R')(R'')$, —$(CH_2)_xC(O)O(CH_2)_yR$, —$(CH_2)_xN(R')(R'')$, —N(R)$SO_2R$, —$O(CH_2)_yC(O)N(R')(R'')$, —$SO_2N(R')(R'')$, —$(CH_2)_xN(R)$—$(CH_2)_y$—R, —$(CH_2)_xN(R)$—C(O)—$(CH_2)_y$—R, —$(CH_2)_xN(R)$—C(O)—O—$(CH_2)_y$—R, —$(CH_2)_x$—C(O)—N(R)—$(CH_2)_y$—R, —$(CH_2)_xC(O)N(R)$—$(CH_2)_y$—R, —O—$(CH_2)_x$—C(O)—N(R)—$(CH_2)_y$—R, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one of more halo, CN, $CF_3$, $CO_2R$, C(O)R, $C(O)NR_2$, $NR_2$, cyclic-amino, $NO_2$, and OR.

The term "aryl" or "aromatic group" as used herein contemplates single-ring aromatic groups (for example, phenyl, pyridyl, pyrazole, etc.) and polycyclic ring systems (naphthyl, quinoline, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. Additionally, the aryl groups may be optionally substituted with one or more substituents selected from halo, CN, $CF_3$, $NR_2$, cyclic-amino, $NO_2$, OR, $CF_3$, —$(CH_2)_xC(O)(CH_2)_yR$, —$(CH_2)_xC(O)N(R')(R'')$, —$(CH_2)_xC(O)O(CH_2)_yR$, —$(CH_2)_xN(R')(R'')$, —N(R)$SO_2R$, —$O(CH_2)C(O)N(R')(R'')$, —$SO_2N(R')(R'')$, —$(CH_2)_xN(R)$—$(CH_2)_y$—R, —$(CH_2)_xN(R)$—C(O)—$(CH_2)_y$—R, —$(CH_2)_xN(R)$—C(O)—O—$(CH_2)_y$—R, —$(CH_2)_x$—C(O)—N(R)—$(CH_2)_y$—R, —$(CH_2)_xC(O)N(R)$—$(CH_2)_y$—R, —O—$(CH_2)_x$—C(O)—N(R)—$(CH_2)_y$—R, substituted and unsubstituted alkyl, substituted and unsubstituted cycloalkyl, substituted and unsubstituted aralkyl, substituted and unsubstituted alkenyl, substituted and unsubstituted alkynyl, substituted and unsubstituted aryl, and a substituted and unsubstituted heterocyclic ring, wherein the substituted alkyl, substituted cycloalkyl, substituted aralkyl, substituted alkenyl, substituted alkynyl, substituted aryl, and substituted heterocyclic ring may be substituted with one of more halo, CN, $CF_3$, $CO_2R$, C(O)R, $C(O)NR_2$, $NR_2$, cyclic-amino, $NO_2$, and OR.

The term "heteroatom", particularly as a ring heteroatom, refers to N, O, and S.

Each R is independently selected from H, substituted and unsubstituted alkyl, substituted and unsubstituted cycloalkyl, substituted and unsubstituted aralkyl, substituted and unsubstituted aryl and a substituted and unsubstituted heterocyclic ring, wherein the substituted alkyl, substituted cycloalkyl, substituted aralkyl, substituted aryl and substituted heterocyclic ring may be substituted with one or more halo, CN, $CF_3$, OH, $CO_2H$, $NO_2$, $C_{1-6}$alkyl, —O—($C_{1-6}$ alkyl), —$NH_2$, —NH($C_{1-6}$alkyl) and N($C_{1-6}$ alkyl)$_2$. Each R' and R" are independently selected from H, or substituted and unsubstituted alkyl, substituted and unsubstituted cycloalkyl, substituted and unsubstituted aralkyl, substituted and unsubstituted aryl and a substituted and unsubstituted heterocyclic ring, wherein the substituted alkyl, substituted cycloalkyl, substituted aralkyl, substituted aryl and substituted heterocyclic ring may be substituted with one or more halo, CN, $CF_3$, OH, $CO_2H$, $NO_2$, $C_{1-6}$alkyl, —O—($C_{1-6}$ alkyl), —$NH_2$, —NH($C_{1-6}$alkyl) and N($C_{1-6}$ alkyl)$_2$; or R' and R" may be taken together with the nitrogen to which they are attached form a 5- to 7-membered ring which may optionally contain up to three further heteroatoms. Each x and each y are independently selected from 0 to 4.

In a preferred embodiment, the present invention provides inhibitors of the $P210^{BCR-ABL-T315I}$ theramutein having the formula I

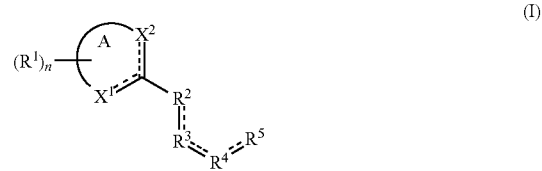

(I)

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;
$R^2$ is selected from $—CR^{21}{}_a—$, $—NR^{22}{}_b—$, and $—(C=R^{23})—$;
  each $R^{21}$ is independently selected from H, halo, $—NH_2$, $—N(H)(C_{1-3}$ alkyl), $—N(C_{1-3}$ alkyl$)_2$, $—O—(C_{1-3}$ alkyl), OH and $C_{1-3}$ alkyl;
  each $R^{22}$ is independently selected from H and $C_{1-3}$ alkyl;
  $R^{23}$ is selected from O, S, N—$R^0$, and N—$OR^0$;
$R^3$ is selected from $CR^{31}{}_c—$, $—NR^{32}{}_d—$, and $—(C=R^{33})—$;
  each $R^{31}$ group is selected from H, halo, $—NH_2$, $—N(H)(R^0)$, $—N(R^0)_2$, $—O—R^0$, OH and $C_{1-3}$ alkyl;
  each $R^{32}$ group is selected from H, alkyl, cycloalkyl, alkenyl, alkynyl, aralkyl, $CO_2R^0$, $C(O)R^0$, aryl, and a heterocyclic ring;
  $R^{33}$ is selected from O, S, N—$R^{34}$, and N—$OR^0$;
  $R^{34}$ is selected from H, $NO_2$, CN, alkyl, cycloalkyl, alkenyl, alkynyl, aralkyl, aryl and a heterocyclic ring;
$R^4$ is selected from $CR^{41}{}_e—$, $—NR^{42}{}_f$, $—(C=R^{43})—$, and $—O—$;
  each $R^{41}$ is selected from H, alkyl, cycloalkyl, alkenyl, alkynyl, $CO_2R^0$, $C(O)R^0$, aralkyl, aryl, and a heterocyclic ring;
  each $R^{42}$ group is selected from H, alkyl, cycloalkyl, alkenyl, alkynyl, aralkyl, $CO_2R^0$, $C(O)R^0$, aryl, and a heterocyclic ring;
  each $R^{43}$ is selected from O, S, N—$R^0$, and N—$OR^0$;
with the provisos that when $R^2$ is $NR^{22}{}_b—$ and $R^4$ is $NR^{42}{}_f—$, then $R^3$ is not $NR^{32}{}_d—$; and that both $R^3$ and $R^4$ are not simultaneously selected from $—(C=R^{33})—$ and $—(C=R^{43})—$, respectively; $R^5$ is selected from $—Y—R^6$ and $—Z—R^7$;
Y is selected from a chemical bond, O, $NR^0$,
$R^6$ is selected from alkyl, cycloalkyl, alkenyl, alkynyl, aralkyl, aryl, and a heterocyclic ring;
Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;
$R^7$ is H or is selected from aryl and a heterocyclic ring;
each $R^0$ is independently selected from H, alkyl, cycloalkyl, aralkyl, aryl and a heterocyclic ring;
a is 1 or 2;
b is 0 or 1;
c is 1 or 2;
d is 0 or 1;
e is 1 or 2; and
f is 0 or 1.

An important component and conceptual teaching of the Invention described herein is that neither the $R^2$ nor the $R^3$ positions of the compounds of this invention are members of any aromatic or non-aromatic ring structure. We have discovered that compounds having the $R^2$ and/or the $R^3$ positions as members of any aromatic or non-aromatic ring structure do not effectively inhibit the T315I theramutein, whereas the compounds of the invention that lack such a ring component at these positions, in addition to having other preferred chemical groups, are potent inhibitors of the T315I theramutein.

In preferred embodiments of the invention, ring A is an aromatic ring.

In preferred embodiments of the invention, $X^1$ or $X^2$ is N. In another preferred embodiment, both $X^1$ and $X^2$ are N. In particularly preferred embodiments of the invention Ring A is a pyridine ring or a pyrimidine ring. In still further preferred embodiments, Ring A is selected from the structures provided below:

In a preferred embodiment, if $R^2$ or $R^4$ is selected to be $—NR^{22}{}_b—$ or $—NR^{42}—$, respectively, then $R^{31}$ is not selected from halo, $—NH_2$, $—N(H)(R^0)$, $—N(R^0)_2$, $—O—R^0$, or OH.

In a further preferred embodiment, the present invention provides inhibitors of the $P210^{BCR-ABL-T315I}$ theramutein having the formula $I_a$ $$(I_a)$$

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, $—(CH_2)_pC(O)(CH_2)_qR^{11}$, $—(CH_2)_pC(O)N(R^{12})(R^{13})$, $—(CH_2)_pC(O)O(CH_2)_qR^{11}$, $—(CH_2)_pN(R^{11})C(O)R^{11}$, $—(CH_2)_pN(R^{12})(R^{13})$, $—N(R^{11})SO_2R^{11}$, $—OC(O)N(R^{12})(R^{13})$, $—SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
  each $R^{11}$ is independently selected from H, alkyl, cycloalkyl, alkenyl, alkynyl, aralkyl, aryl, and a heterocyclic ring;
  each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;
each $R^{22}$ is independently selected from H and $C_{1-3}$ alkyl;
$R^3$ is selected from $CR^{31}{}_c—$, $—NR^{32}{}_d—$, and $—(C=R^{33})—$;
  each $R^{31}$ group is selected from H, halo, $—NH_2$, $—N(H)(R^0)$, $—N(R^0)_2$, $—O—R^0$, OH and $C_{1-3}$ alkyl;

each $R^{32}$ group is selected from H, alkyl, cycloalkyl, alkenyl, alkynyl, aralkyl, $CO_2R^0$, $C(O)R^0$, aryl, and a heterocyclic ring;

$R^{33}$ is selected from O, S, N—$R^{34}$, and N—$OR^0$;

$R^{34}$ is selected from H, $NO_2$, CN, alkyl, cycloalkyl, alkenyl, alkynyl, aralkyl, aryl and a heterocyclic ring;

$R^4$ is selected from $CR^{41}{}_e$—, —$NR^{42}{}_f$—, —(C=$R^{43}$)—, and —O—;

each $R^{41}$ is selected from H, alkyl, cycloalkyl, alkenyl, alkynyl, $CO_2R^0$, $C(O)R^0$, aralkyl, aryl, and a heterocyclic ring;

each $R^{42}$ group is selected from H, alkyl, cycloalkyl, alkenyl, alkynyl, aralkyl, $CO_2R^0$, $C(O)R^0$, aryl, and a heterocyclic ring;

each $R^{43}$ is selected from O, S, N—$R^0$, and N—$OR^0$;

with the provisos that when $R^4$ is —$NR^{42}{}_f$—, then $R^3$ is not —$NR^{32}{}_d$—; and that both $R^3$ and $R^4$ are not simultaneously selected from —(C=$R^{33}$)— and —(C=$R^{43}$)—, respectively;

$R^5$ is selected from —Y—$R^6$ and —Z—$R^7$;

Y is selected from a chemical bond, O, N—$R^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^7$ is H or is selected from aryl and a heterocyclic ring;

each $R^0$ is independently selected from H, alkyl, cycloalkyl, aralkyl, aryl and a heterocyclic ring;

a is 1 or 2;
b is 0 or 1;
c is 1 or 2;
d is 0 or 1;
e is 1 or 2; and
f is 0 or 1.

In a further preferred embodiment, the present invention provides inhibitors of the $P210^{BCR-ABL-T315I}$ theramutein having the formula $I_b$

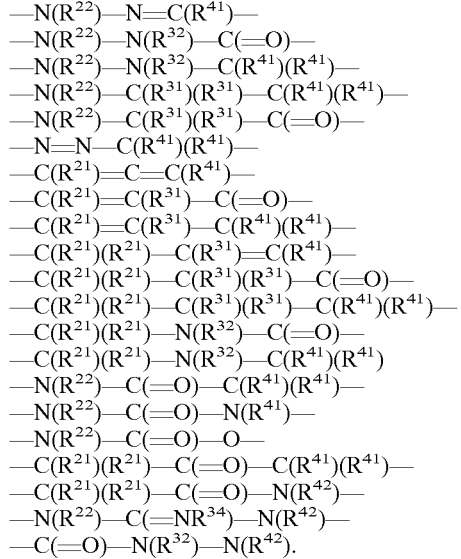

wherein:
ring A is a 5-, 6-, or 7-membered ring or a 7- to 12-membered fused bicyclic ring;

$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;
q is 0 to 4;
each $R^{22}$ is independently selected from H and $C_{1-3}$ alkyl;
each $R^{32}$ group is selected from H, alkyl, cycloalkyl, alkenyl, alkynyl, aralkyl, $CO_2R^0$, $C(O)R^0$, aryl, and a heterocyclic ring;

$R^4$ is selected from —$CR^{41}{}_e$—, —(C=$R^{43}$)—, and —O—;

each $R^{41}$ is selected from H, alkyl, cycloalkyl, alkenyl, alkynyl, $CO_2R^0$, $C(O)R^0$, aralkyl, aryl, and a heterocyclic ring;

each $R^{43}$ is selected from O, S, N—$R^0$, and N—$OR^0$;

$R^5$ is selected from —Y—$R^6$ and —Z—$R^7$;

Y is selected from a chemical bond, O, N—$R^0$, $R^6$ is selected from alkyl, cycloalkyl, alkenyl, alkynyl, aralkyl, aryl, and a heterocyclic ring;

Z is a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^7$ is H or is selected from aryl and a heterocyclic ring;

each $R^0$ is independently selected from H, alkyl, cycloalkyl, aralkyl, aryl and a heterocyclic ring;

a is 1 or 2;
b is 0 or 1;
c is 1 or 2;
d is 0 or 1;
e is 1 or 2; and
f is 0 or 1.

In preferred embodiments of the invention, $R^2$, $R^3$ and $R^4$ of formula I are selected to give the following chemical groups:

—$N(R^{22})$—N=C($R^{41}$)—
—$N(R^{22})$—$N(R^{32})$—C(=O)—
—$N(R^{22})$—$N(R^{32})$—C($R^{41}$)($R^{41}$)—
—$N(R^{22})$—C($R^{31}$)($R^{31}$)—C($R^{41}$)($R^{41}$)—
—$N(R^{22})$—C($R^{31}$)($R^{31}$)—C(=O)—
—N=N—C($R^{41}$)($R^{41}$)—
—C($R^{21}$)=C=C($R^{41}$)—
—C($R^{21}$)=C($R^{31}$)—C(=O)—
—C($R^{21}$)=C($R^{31}$)—C($R^{41}$)($R^{41}$)—
—C($R^{21}$)($R^{21}$)—C($R^{31}$)=C($R^{41}$)—
—C($R^{21}$)($R^{21}$)—C($R^{31}$)($R^{31}$)—C(=O)—
—C($R^{21}$)($R^{21}$)—C($R^{31}$)($R^{31}$)—C($R^{41}$)($R^{41}$)—
—C($R^{21}$)($R^{21}$)—$N(R^{32})$—C(=O)—
—C($R^{21}$)($R^{21}$)—$N(R^{32})$—C($R^{41}$)($R^{41}$)
—$N(R^{22})$—C(=O)—C($R^{41}$)($R^{41}$)—
—$N(R^{22})$—C(=O)—N($R^{41}$)—
—$N(R^{22})$—C(=O)—O—
—C($R^{21}$)($R^{21}$)—C(=O)—C($R^{41}$)($R^{41}$)—
—C($R^{21}$)($R^{21}$)—C(=O)—$N(R^{42})$—
—$N(R^{22})$—C(=$NR^{34}$)—$N(R^{42})$—
—C(=O)—$N(R^{32})$—$N(R^{42})$.

Particularly preferred chemical groups for $R^2$, $R^3$ and $R^4$ include:
—$N(R^{22})$—N=C($R^{41}$)—
—$N(R^{22})$—$N(R^{32})$—C(=O)—
—$N(R^{22})$—C($R^{31}$)($R^{31}$)—C($R^{41}$)($R^{41}$)—

—N($R^{22}$)—C($R^{31}$)($R^{31}$)—C(=O)—
—C($R^{21}$)($R^{21}$)—C(=O)—C($R^{41}$)($R^{41}$)—
—C($R^{21}$)($R^{21}$)—C(=O)—N($R^{42}$)—
—N($R^{22}$)—C(=N$R^{34}$)—N($R^{42}$)—
—C(=O)—N($R^{32}$)—N($R^{42}$).

In further preferred embodiment, $R^6$ or $R^7$ is an aryl group, which may be optionally substituted. Particularly preferred aryl groups include substituted or unsubstituted phenyl and pyridyl. In additional or alternative embodiments, it is preferred that the substituents $R^{21}$ and $R^{22}$ are independently selected from groups which have small steric bulk and are preferably selected from H and $CH_3$, and more preferably are H.

In a further preferred embodiment, the present invention provides inhibitors of the $P210^{BCR-ABL-T315I}$ theramutein having the formula II

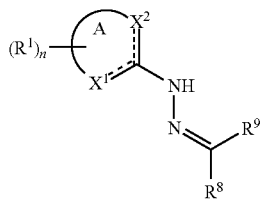

(II)

wherein
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;
$R^8$ is selected from the group consisting of is selected from H, alkyl, cycloalkyl, alkenyl, alkynyl, $CO_2R^0$, $C(O)R^0$, aralkyl, aryl, and a heterocyclic ring;
$R^9$ is selected from —Y—$R^6$ and —Z—$R^7$;
Y is selected from a chemical bond, O, N—$R^0$,
$R^6$ is selected from alkyl, cycloalkyl, alkenyl, alkynyl, aralkyl, aryl, and a heterocyclic ring;
Z is a hydrocarbon chain having from 1 to 4 carbon atoms, and optionally substituted with one or more of halo, alkyl, cycloalkyl, alkenyl, alkynyl, aralkyl, $CO_2R$, $C(O)R^0$, $C(O)N(R^0)_2$, CN, $CF_3$, $N(R^0)_2$, $NO_2$, and $OR^0$;

$R^7$ is H or is selected from aryl and a heterocyclic ring; and
each $R^0$ is independently selected from H, alkyl, cycloalkyl, aralkyl, aryl and a heterocyclic ring.

In a further preferred embodiment, the present invention provides inhibitors of the $P210^{BCR-ABL-T315}$ theramutein having the formula $II_a$

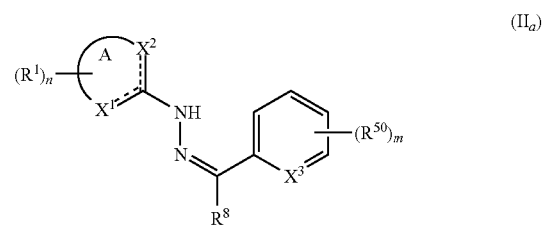

($II_a$)

wherein
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;
$R^8$ is selected from the group consisting of is selected from H, alkyl, cycloalkyl, alkenyl, alkynyl, $CO_2R^0$, $C(O)R^0$, aralkyl, aryl, and a heterocyclic ring;
$X^3$ is N, CH or C—$R^{50}$;
each $R^{50}$ is independently selected from the group consisting of alkyl, cycloalkyl, alkenyl, alkynyl, aralkyl, CN, $CF_3$, $NO_2$, $OR^{51}$, —$(CH_2)_rC(O)(CH_2)_sR^{51}$, —$(CH_2)_rC(O)N(R^{52})(R^{53})$, —$(CH_2)_rC(O)O(CH_2)_sR^{51}$, —$(CH_2)_rN(R^{51})C(O)R^{51}$, —$(CH_2)_rN(R^{52})(R^{53})$, —$N(R^{51})SO_2R^{51}$, —$OC(O)N(R^{52})(R^{53})$, —$SO_2N(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;
$R^{51}$ is selected from H, alkyl, cycloalkyl, alkenyl, alkynyl, aralkyl, aryl, and a heterocyclic ring;
$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom;

r is 0 to 4;
s is 0 to 4;
m is 0 to 4; and
each $R^0$ is independently selected from H, alkyl, cycloalkyl, aralkyl, aryl and a heterocyclic ring.

In a further preferred embodiment, the present invention provides inhibitors of the $P210^{BCR-ABL-T315I}$ theramutein having the formula $II_b$,

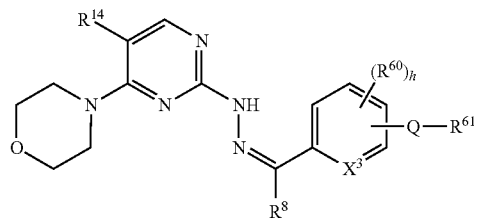

wherein:
$R^{14}$ is selected from H and F;
$R^8$ is selected from the group consisting of H, alkyl, cycloalkyl, alkenyl, alkynyl, $CO_2R^0$, $C(O)R^0$, aralkyl, aryl, and a heterocyclic ring;
$X^3$ is N, CH or C—$R^{60}$;
each $R^{60}$ is independently selected from the group consisting of alkyl, cycloalkyl, alkenyl, alkynyl, aralkyl, CN, $CF_3$, $NO_2$, $OR^0$, halo, aryl, and a heterocyclic ring;
$R^{61}$ is selected from aryl and a heterocyclic ring;
Q is selected from a chemical bond or a group having the formula —O—, —$(CH_2)_i$—, —$(CH_2)_iC(O)(CH_2)_j$—, —$(CH_2)_i$—N($R^{62}$)—$(CH_2)_j$—, —$(CH_2)_iC(O)$—N($R^{62}$)—$(CH_2)_j$—, —$(CH_2)_iC(O)O(CH_2)_j$—, —$(CH_2)_iN(R^{62})C(O)$—$(CH_2)_j$—, —$(CH_2)_iOC(O)N(R^{62})$—$(CH_2)_j$—, and —O—$(CH_2)_i$—$C(O)N(R^{62})$—$(CH_2)_j$—;
$R^{62}$ is selected from aryl, and a heterocyclic ring;
each $R^0$ is independently selected from H, alkyl, cycloalkyl, aralkyl, aryl and a heterocyclic ring;
h is 0 to 4;
i is 0 to 4; and
j is 0 to 4.

In preferred embodiments of compounds of the formula $II_b$, $R^{60}$ is selected from halo, $CF_3$, and OH.

Exemplary compounds of the formula II, $II_a$ or $II_b$ includes the following structures:

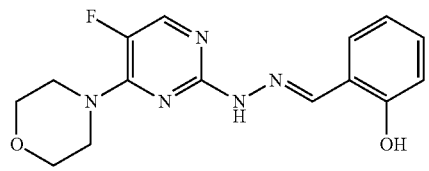

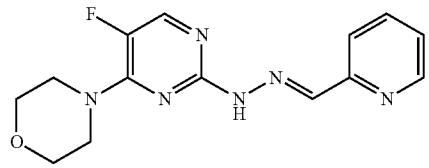

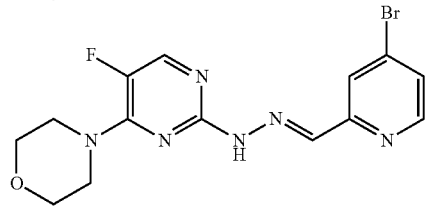

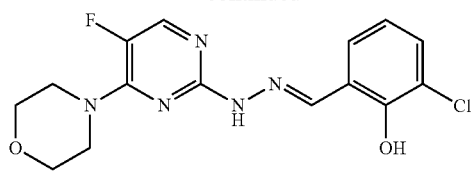

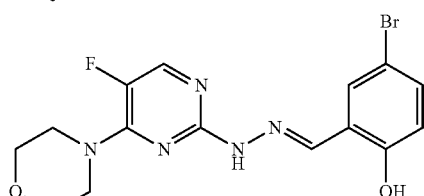

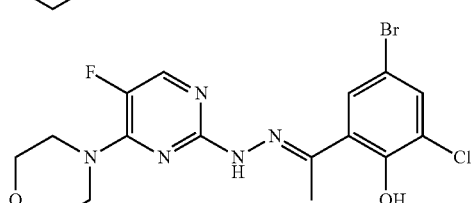

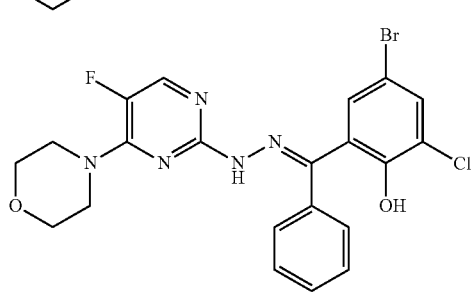

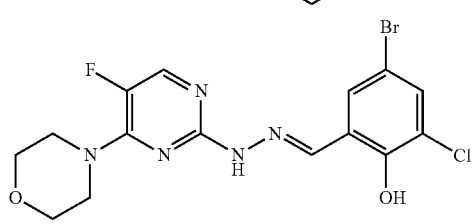

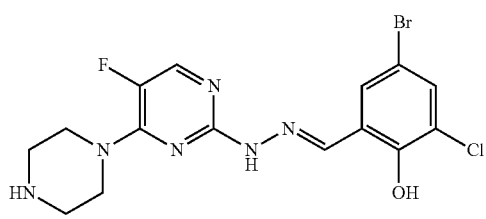

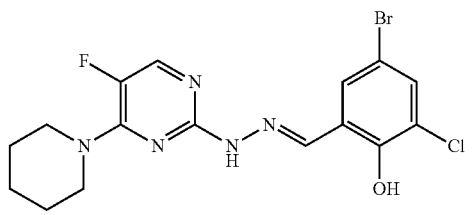

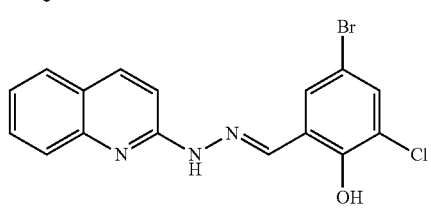

-continued
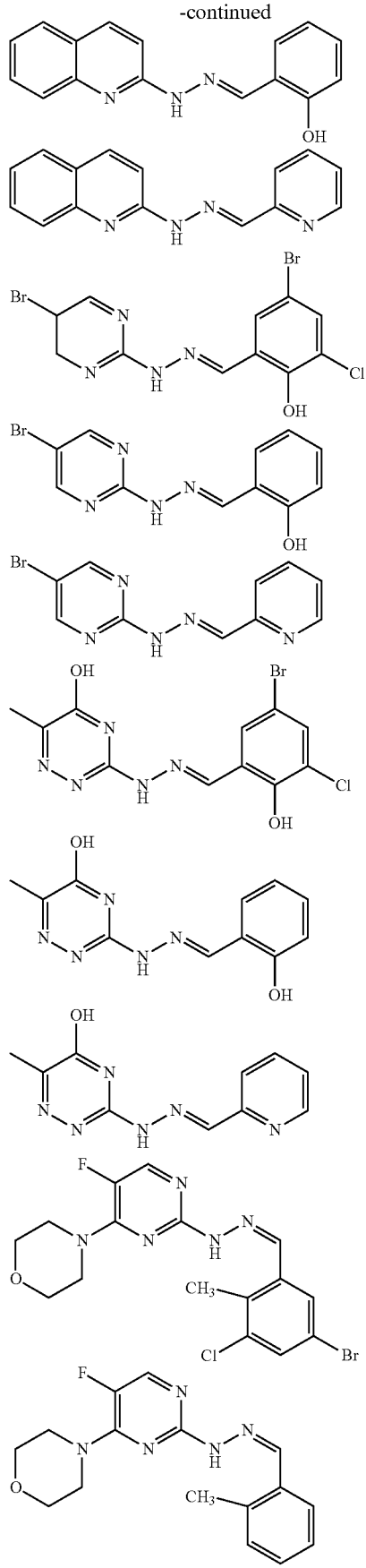
-continued
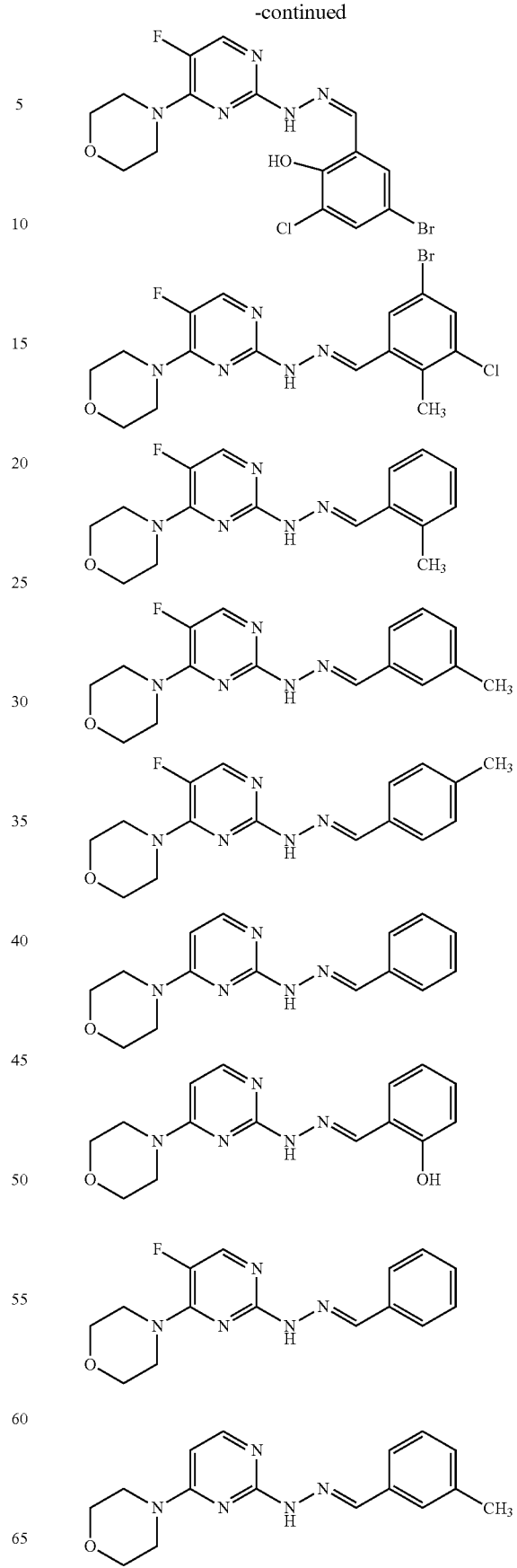

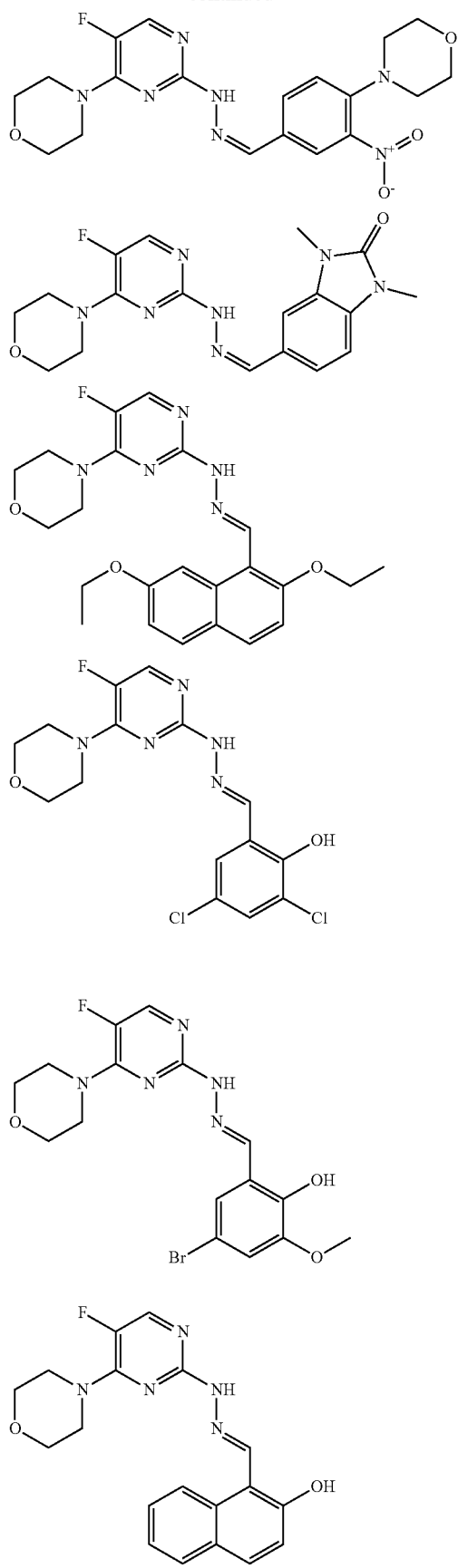
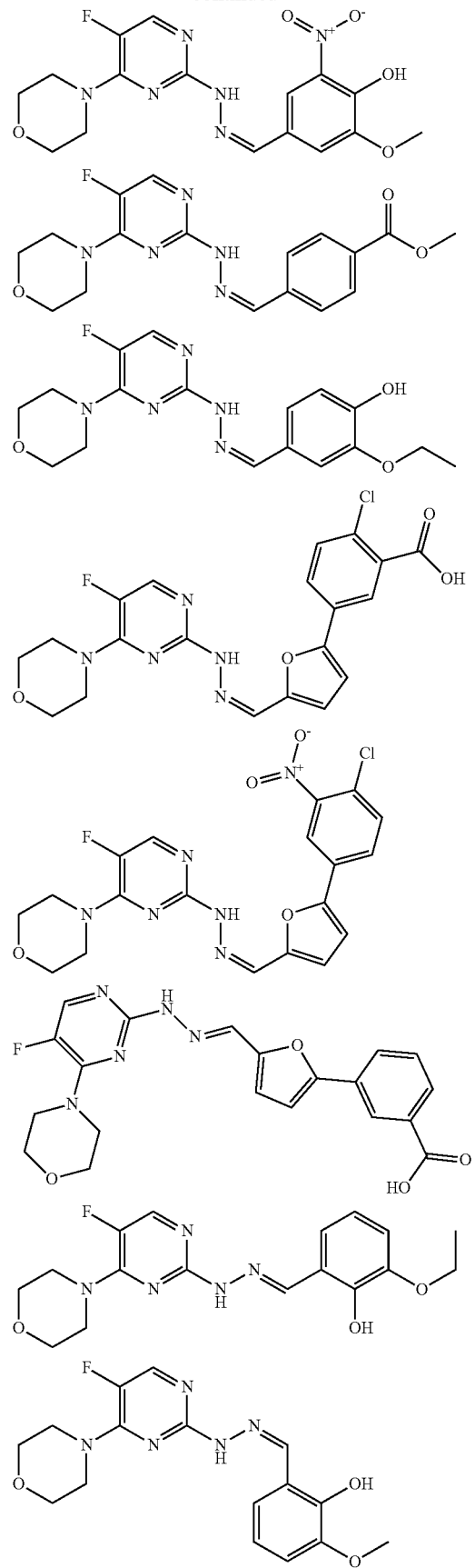

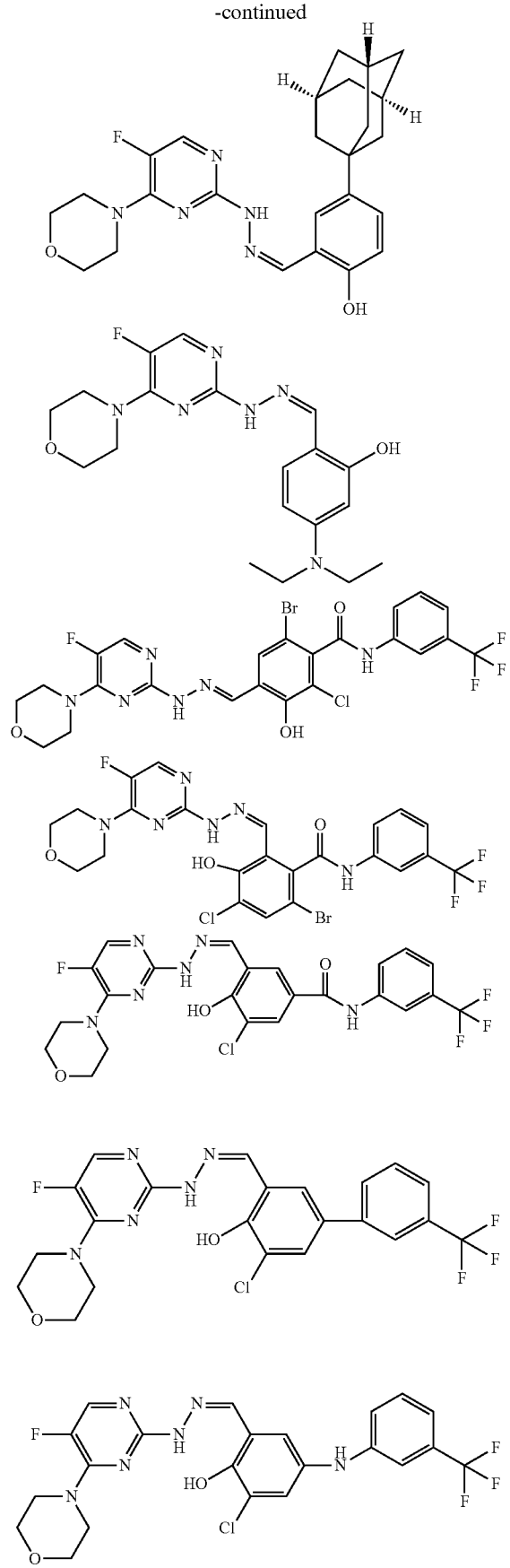
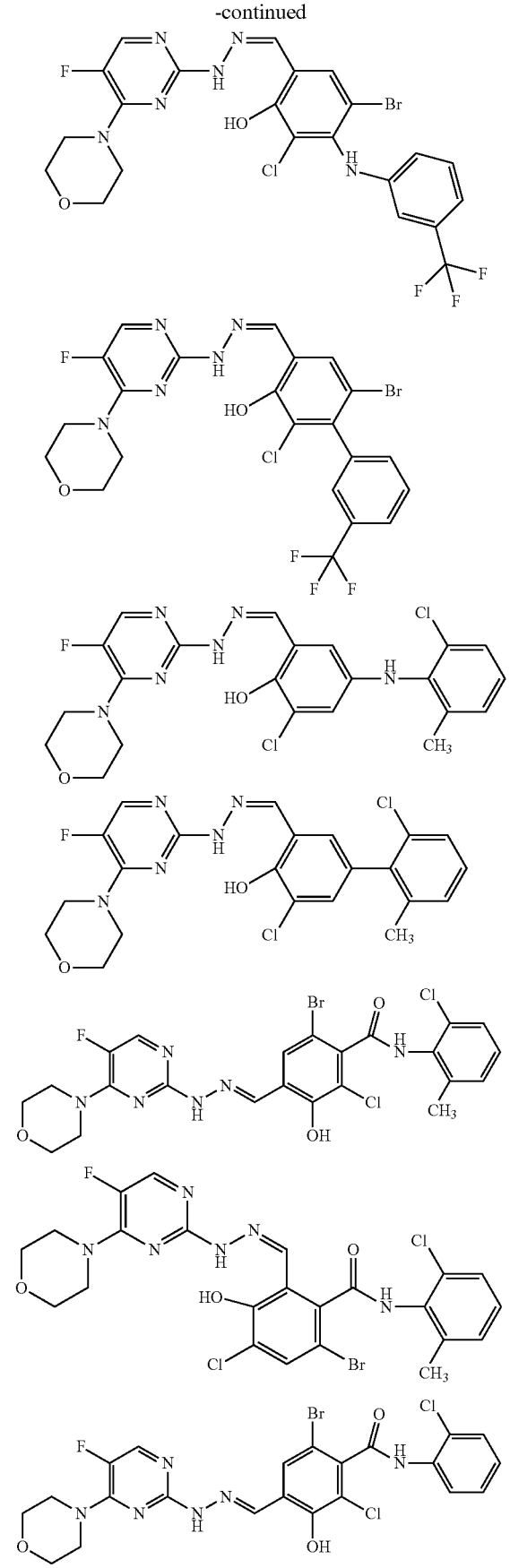

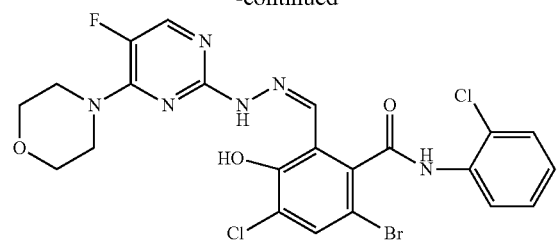
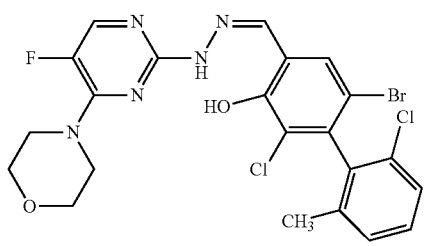
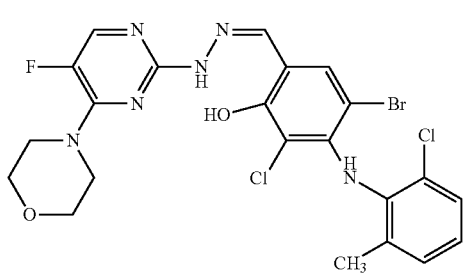
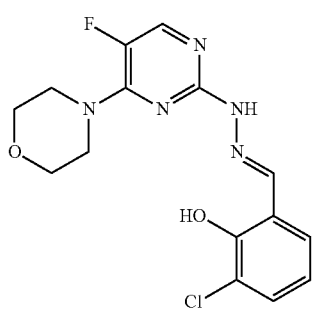
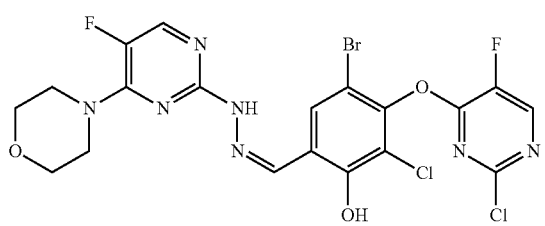
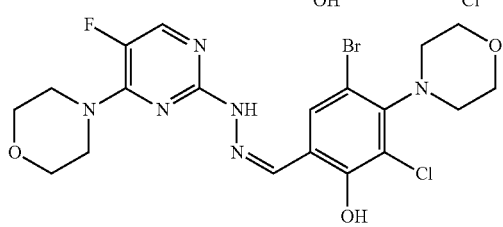
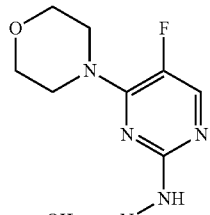
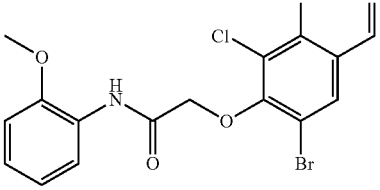
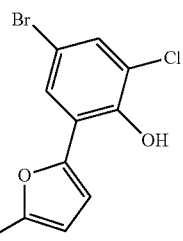
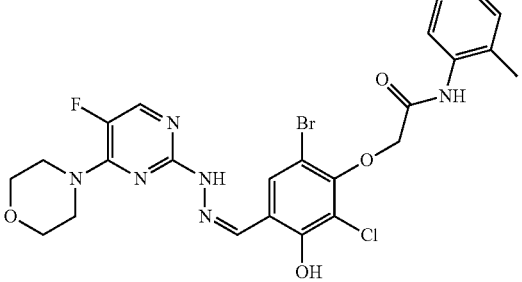
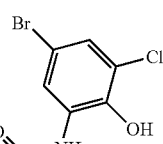
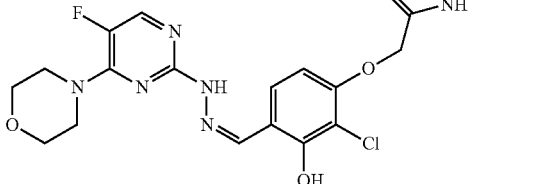
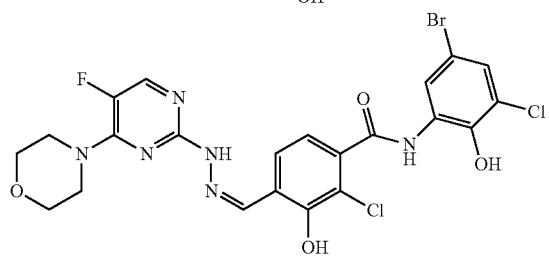

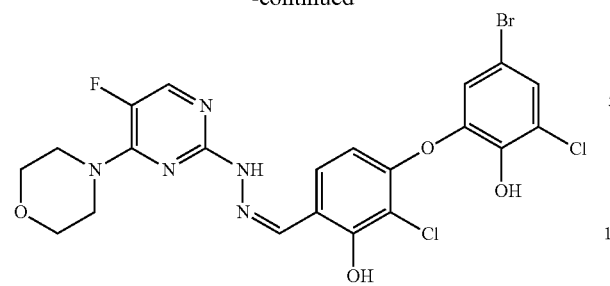
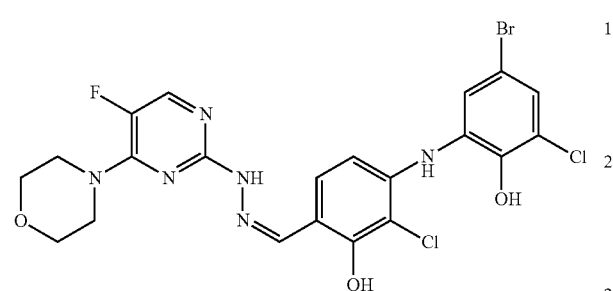
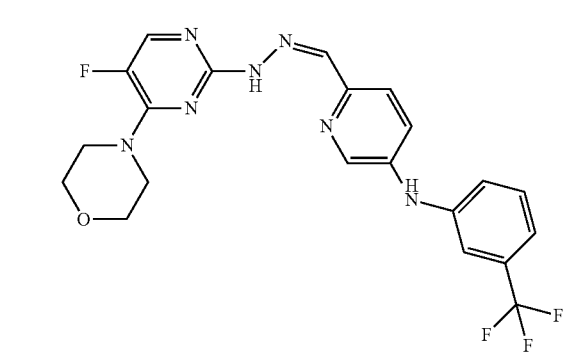
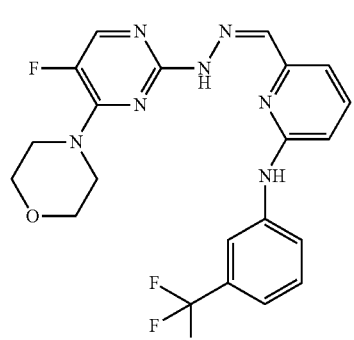
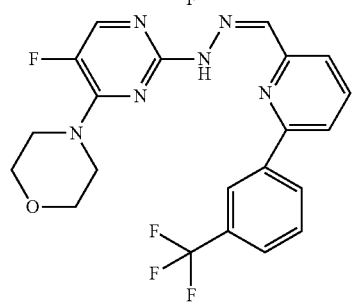
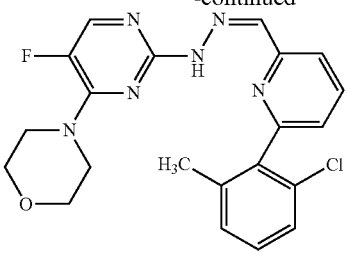
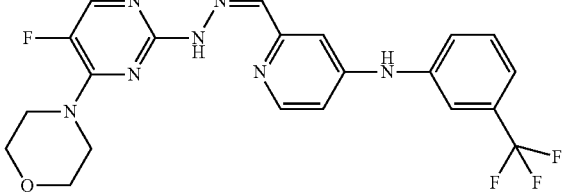
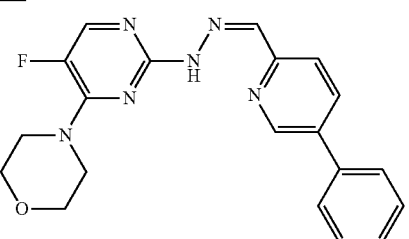
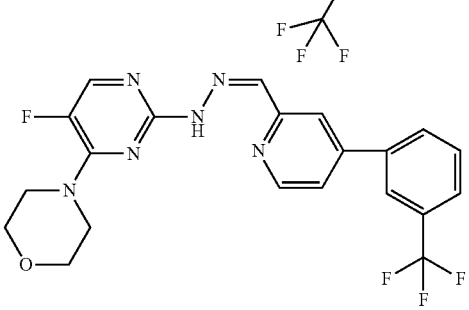
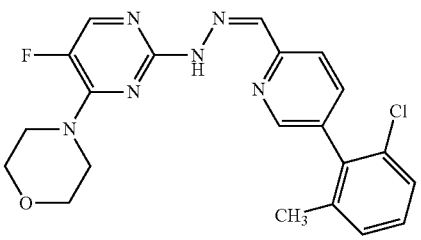
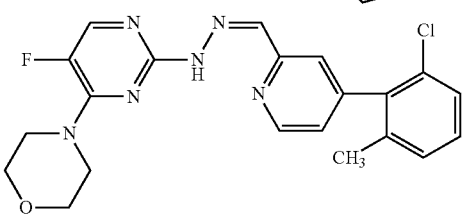
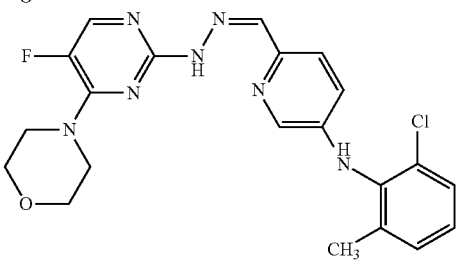

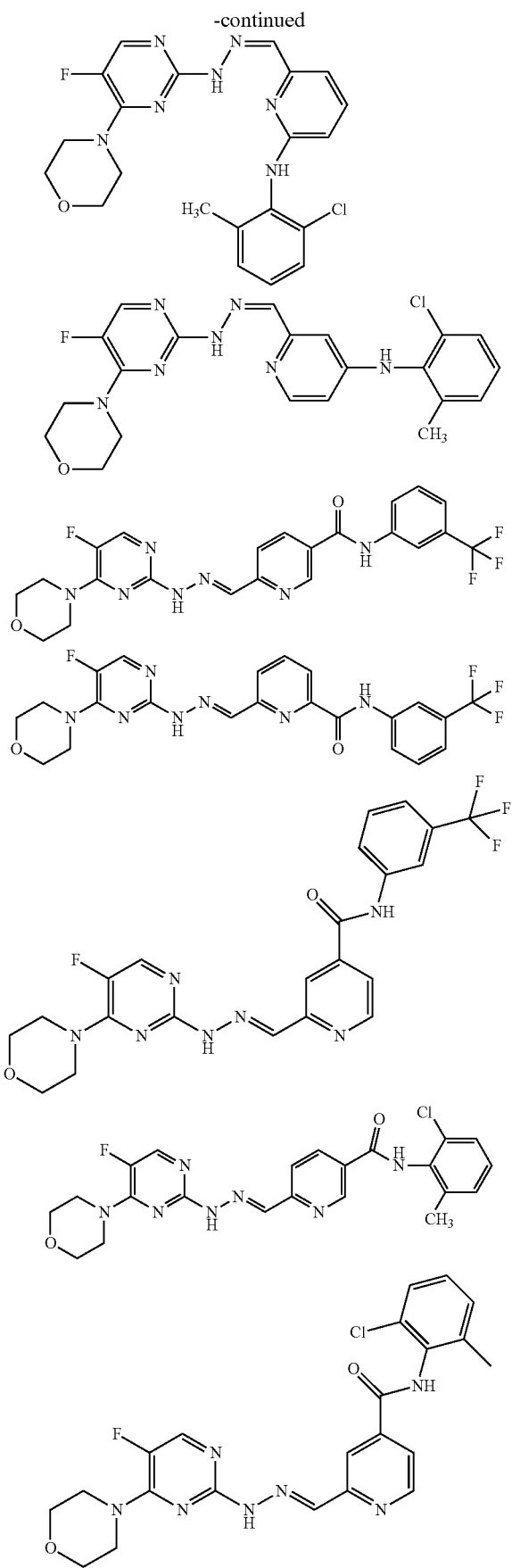
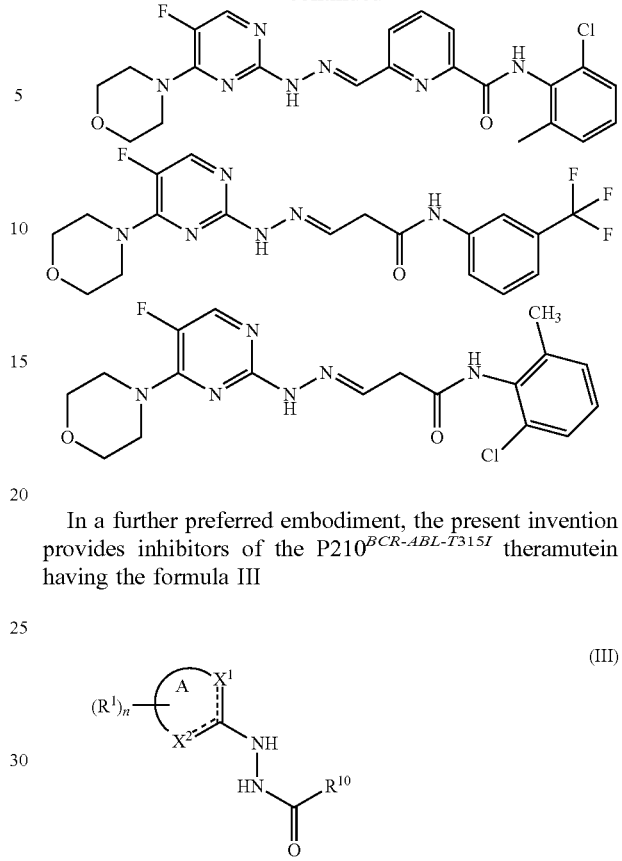

In a further preferred embodiment, the present invention provides inhibitors of the P210$^{BCR\text{-}ABL\text{-}T315I}$ theramutein having the formula III

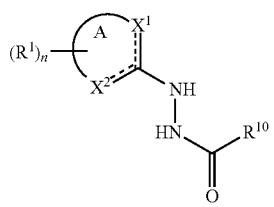

(III)

wherein
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;
$R^{10}$ is selected from —Y'—$R^8$;
Y' is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, CO$_2$R, C(O)R$^0$, C(O)N(R$^0$)$_2$, CN, CF$_3$, N(R$^0$)$_2$, NO$_2$, and OR$^0$;

R$^{18}$ is selected from the group consisting of H, alkyl, cycloalkyl, alkenyl, alkynyl, aralkyl, CF$_3$, aryl, and a heterocyclic ring; and each R$^0$ is independently selected from H, alkyl, cycloalkyl, aralkyl, aryl and a heterocyclic ring.

In a further preferred embodiment, the present invention provides inhibitors of the P210$^{BCR-ABL-T315I}$ theramutein having the formula III$_a$

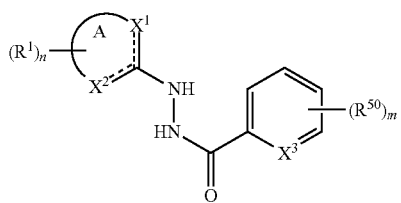

(III$_a$)

wherein:
ring A is a 5-, 6-, or 7-membered ring or a 7- to 12-membered fused bicyclic ring;
X$^1$ is selected from N, N—R$^0$ or C—R$^1$;
X$^2$ is selected from N, N—R$^0$ or C—R$^1$;
the dotted lines represent optional double bonds;
each R$^1$ is independently selected from the group consisting of H, alkyl, cycloalkyl, alkenyl, alkynyl, aralkyl, CN, CF$_3$, NO$_2$, OR$^{11}$, —(CH$_2$)$_p$C(O)(CH$_2$)$_q$R$^{11}$, —(CH$_2$)$_p$C(O)N(R$^{12}$)(R$^{13}$), —(CH$_2$)$_p$C(O)O(CH$_2$)$_q$R$^{11}$, —(CH$_2$)$_p$N(R$^{11}$)C(O)R$^{11}$, —(CH$_2$)$_p$N(R$^{12}$)(R$^{13}$), —N(R$^{11}$)SO$_2$R$^{11}$, —OC(O)N(R$^{12}$)(R$^{13}$), —SO$_2$N(R$^{12}$)(R$^{13}$), halo, aryl, and a heterocyclic ring, and additionally or alternatively, two R$^1$ groups on adjacent ring atoms form a 5- or 6-membered fused ring which contains from 0 to 3 heteroatoms;
n is 0 to 6,
each R$^{11}$ is independently selected from H, alkyl, cycloalkyl, alkenyl, alkynyl, aralkyl, aryl, and a heterocyclic ring;
each R$^{12}$ and R$^{13}$ are independently selected from H, alkyl, cycloalkyl, alkenyl, alkynyl, aralkyl, aryl, and a heterocyclic ring; or R$^{12}$ and R$^{13}$ may be taken together with the nitrogen to which they are attached form a 5- to 7-membered ring which may optionally contain a further heteroatom;
p is 0 to 4;
q is 0 to 4;
X$^3$ is N, CH or C—R$^{50}$;
each R$^{50}$ is independently selected from the group consisting of alkyl, cycloalkyl, alkenyl, alkynyl, aralkyl, CN, CF$_3$, NO$_2$, OR$^{51}$, —(CH$_2$)$_r$C(O)(CH$_2$)$_s$R$^{51}$, —(CH$_2$)$_r$C(O)N(R$^{52}$)(R$^{53}$), —(CH$_2$)$_r$C(O)O(CH$_2$)$_s$R$^{51}$, —(CH$_2$)$_r$N(R$^{51}$)C(O)R$^{51}$, —(CH$_2$)$_r$N(R$^{52}$)(R$^{53}$), —N(R$^{51}$)SO$_2$R$^{51}$, —OC(O)N(R$^{52}$)(R$^3$), —SO$_2$N(R$^{52}$)(R$^{53}$), halo, aryl, and a heterocyclic ring, and additionally or alternatively, two R$^{50}$ groups on adjacent ring atoms form a 5- or 6-membered fused ring which contains from 0 to 3 heteroatoms;
R$^{51}$ is selected from H, alkyl, cycloalkyl, alkenyl, alkynyl, aralkyl, aryl, and a heterocyclic ring;
R$^{52}$ and R$^{53}$ are independently selected from H, alkyl, cycloalkyl, alkenyl, alkynyl, aralkyl, aryl, and a heterocyclic ring; or R$^{52}$ and R$^{53}$ may be taken together with the nitrogen to which they are attached form a 5- to 7-membered ring which may optionally contain a further heteroatom;

r is 0 to 4;
s is 0 to 4;
m is 0 to 4; and
each R$^0$ is independently selected from H, alkyl, cycloalkyl, aralkyl, aryl and a heterocyclic ring.

Exemplary compounds of the formula III or III$_a$ includes the following structures:

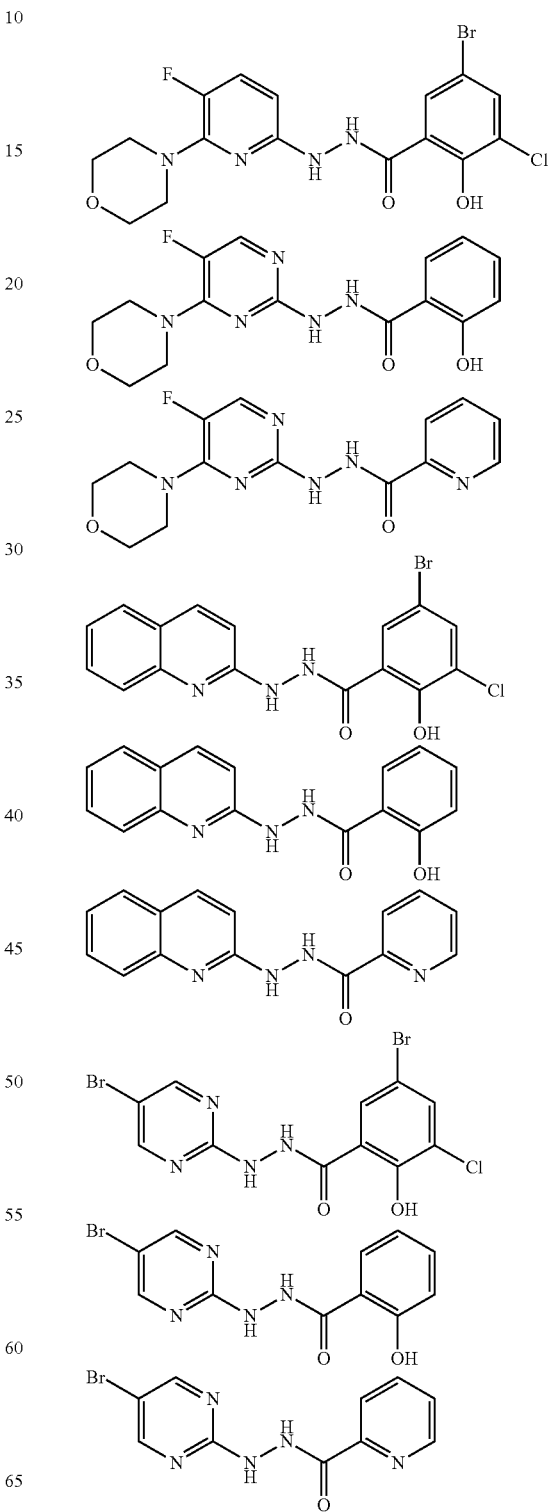

-continued

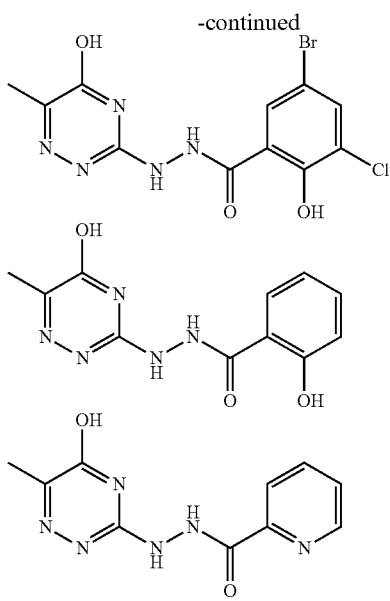

In a further embodiment, the present invention provides inhibitors of the P210$^{BCR-ABL-T315I}$ theramutein having the formula IV

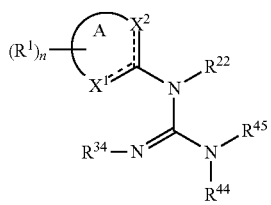

(IV)

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;

$R^{22}$ is selected from H and $C_{1-3}$ alkyl;
$R^{34}$ is selected from H, $NO_2$, CN, alkyl, cycloalkyl, alkenyl, alkynyl, aralkyl, aryl and a heterocyclic ring;
$R^{44}$ is selected from H, alkyl, cycloalkyl, —(C=O)$R^0$, alkenyl, alkynyl, aralkyl, aryl, and a heterocyclic ring;
$R^{45}$ is selected from —Y"—$R^{19}$;
Y" is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;
$R^{19}$ is selected from the group consisting of H, alkyl, cycloalkyl, alkenyl, alkynyl, aralkyl, $CF_3$, aryl, and a heterocyclic ring; and
each $R^0$ is independently selected from H, alkyl, cycloalkyl, aralkyl, aryl and a heterocyclic ring.

Exemplary compounds of the formula IV include the following structures:

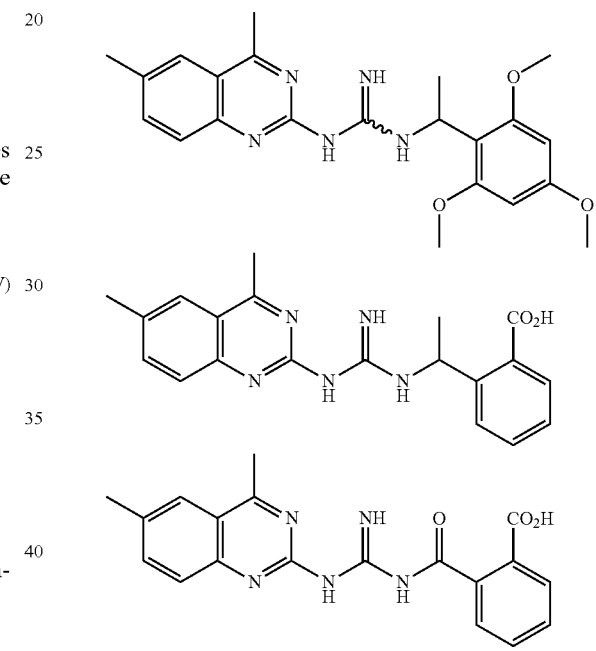

In a further embodiment, the present invention provides inhibitors of the P210$^{BCR-ABL-T315I}$ theramutein having the formula V

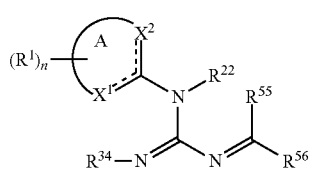

(V)

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each $R^{11}$ is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{22}$ is selected from H and $C_{1-3}$ alkyl;

$R^{34}$ is selected from H, $NO_2$, CN, alkyl, cycloalkyl, alkenyl, alkynyl, aralkyl, aryl and a heterocyclic ring;

$R^{55}$ is selected from H, alkyl, cycloalkyl, alkenyl, alkynyl, aralkyl, aryl, and a heterocyclic ring;

$R^{56}$ is selected from —Y''—$R^{19}$;

Y'' is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, $CO_2R^0$, $C(O)R^0$, $C(O)N(R^0)_2$, CN, $CF_3$, $N(R^0)_2$, $NO_2$, and $OR^0$;

$R^{19}$ is selected from the group consisting of H, alkyl, cycloalkyl, alkenyl, alkynyl, aralkyl, $CF_3$, aryl, and a heterocyclic ring; and each $R^0$ is independently selected from H, alkyl, cycloalkyl, aralkyl, aryl and a heterocyclic ring.

In a further embodiment, the present invention provides inhibitors of the $P210^{BCR-ABL-T315I}$ theramutein having the formula $V_a$

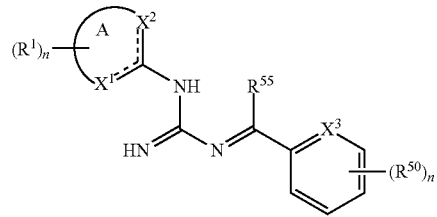

(Va)

wherein:

ring A is a 5-, 6-, or 7-membered ring or a 7- to 12-membered fused bicyclic ring;

$X^1$ is selected from N, N—$R^0$ or C—$R^1$;

$X^2$ is selected from N, N—$R^0$ or C—$R^1$;

the dotted lines represent optional double bonds;

each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;

n is 0 to 6, each R'' is independently selected from H, alkyl, cycloalkyl, alkenyl, alkynyl, aralkyl, aryl, and a heterocyclic ring;

each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;

q is 0 to 4;

$R^{55}$ is selected from H, alkyl, cycloalkyl, alkenyl, alkynyl, aralkyl, aryl, and a heterocyclic ring;

$X^3$ is N or C—$R^{50}$;

each $R^{50}$ is independently selected from the group consisting of alkyl, cycloalkyl, alkenyl, alkynyl, aralkyl, CN, $CF_3$, $NO_2$, $OR^{51}$, —$(CH_2)_rC(O)(CH_2)_sR^{51}$, —$(CH_2)_rC(O)N(R^{52})(R^{53})$, —$(CH_2)_rC(O)O(CH_2)_sR^{51}$, —$(CH_2)_rN(R^{51})C(O)R^{51}$, —$(CH_2)_rN(R^{52})(R^{53})$, —$N(R^{51})SO_2R^{51}$, —$OC(O)N(R^{52})(R^{53})$, —$SO_2N(R^{52})(R^{53})$, halo, aryl, and a heterocyclic ring, and additionally or alternatively, two $R^{50}$ groups on adjacent ring atoms form a 5- or 6-membered fused ring which contains from 0 to 3 heteroatoms;

$R^{51}$ is selected from H, alkyl, cycloalkyl, alkenyl, alkynyl, aralkyl, aryl, and a heterocyclic ring;

$R^{52}$ and $R^{53}$ are independently selected from H, alkyl, cycloalkyl, alkenyl, alkynyl, aralkyl, aryl, and a heterocyclic ring; or $R^{52}$ and $R^{53}$ may be taken together with the nitrogen to which they are attached form a 5- to 7-membered ring which may optionally contain a further heteroatom;

r is 0 to 4;

s is 0 to 4;

m is 0 to 4; and each $R^0$ is independently selected from H, alkyl, cycloalkyl, aralkyl, aryl and a heterocyclic ring.

Exemplary compounds of the formula V or $V_a$ include the following structures:

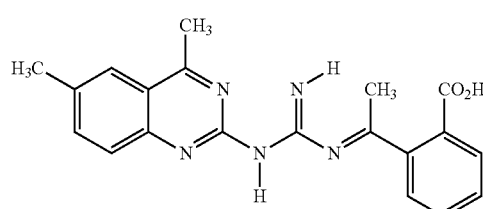

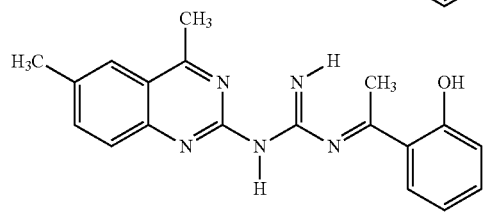

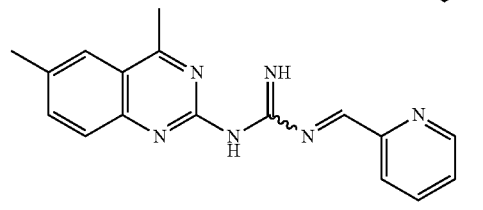

-continued

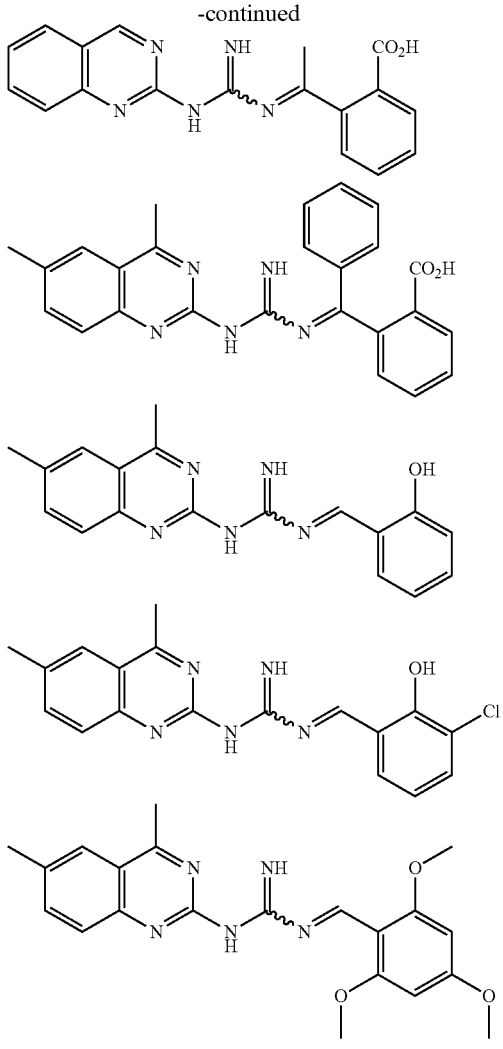

In a further embodiment, the present invention provides inhibitors of the P210$^{BCR-ABL-T315I}$ theramutein having the formula VI

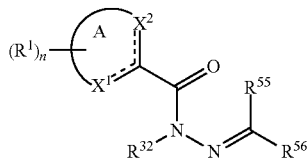
(VI)

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;
p is 0 to 4;
q is 0 to 4;
$R^{55}$ is selected from H, alkyl, cycloalkyl, alkenyl, alkynyl, aralkyl, aryl, and a heterocyclic ring;
$R^{56}$ is selected from —Y"—$R^{19}$;
Y" is selected from a chemical bond, O, $NR^0$—, and a hydrocarbon chain having from 1 to 4 carbon atoms, and optionally substituted with one or more of halo, alkyl, cycloalkyl, alkenyl, alkynyl, aralkyl, $CO_2R$, $C(O)R^0$, $C(O)N(R^0)_2$, CN, $CF_3$, $N(R^0)_2$, $NO_2$, and $OR^0$;
$R^{19}$ is selected from the group consisting of H, alkyl, cycloalkyl, alkenyl, alkynyl, aralkyl, $CF_3$, aryl, and a heterocyclic ring; and
each $R^0$ is independently selected from H, alkyl, cycloalkyl, aralkyl, aryl and a heterocyclic ring.

In a further embodiment, the present invention provides inhibitors of the P210$^{BCR-ABL-T315I}$ theramutein having the formula VI$_a$

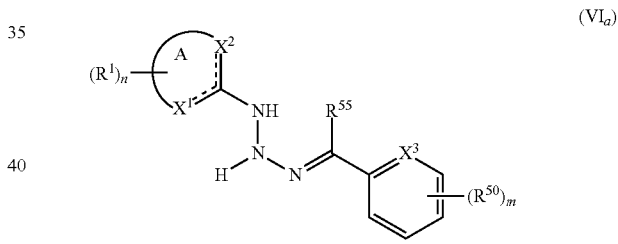
(VI$_a$)

wherein:
ring A is a 5-, 6-, or 7-membered ring or a 7- to 12-membered fused bicyclic ring;
$X^1$ is selected from N, N—$R^0$ or C—$R^1$;
$X^2$ is selected from N, N—$R^0$ or C—$R^1$;
the dotted lines represent optional double bonds;
each $R^1$ is independently selected from the group consisting of H, alkyl, cycloalkyl, alkenyl, alkynyl, aralkyl, CN, $CF_3$, $NO_2$, $OR^{11}$, —$(CH_2)_pC(O)(CH_2)_qR^{11}$, —$(CH_2)_pC(O)N(R^{12})(R^{13})$, —$(CH_2)_pC(O)O(CH_2)_qR^{11}$, —$(CH_2)_pN(R^{11})C(O)R^{11}$, —$(CH_2)_pN(R^{12})(R^{13})$, —$N(R^{11})SO_2R^{11}$, —$OC(O)N(R^{12})(R^{13})$, —$SO_2N(R^{12})(R^{13})$, halo, aryl, and a heterocyclic ring, and additionally or alternatively, two $R^1$ groups on adjacent ring atoms form a 5- or 6-membered fused ring which contains from 0 to 3 heteroatoms;
n is 0 to 6,
each $R^{11}$ is independently selected from H, alkyl, cycloalkyl, alkenyl, alkynyl, aralkyl, aryl, and a heterocyclic ring;
each $R^{12}$ and $R^{13}$ are independently selected from H, alkyl, cycloalkyl, alkenyl, alkynyl, aralkyl, aryl, and a heterocyclic ring; or $R^{12}$ and $R^{13}$ may be taken together with the nitrogen to which they are attached form a 5- to 7-membered ring which may optionally contain a further heteroatom;

p is 0 to 4;
q is 0 to 4;
R⁵⁵ is selected from H, alkyl, cycloalkyl, alkenyl, alkynyl, aralkyl, aryl, and a heterocyclic ring;
X³ is N or C—R⁵⁰;
each R⁵⁰ is independently selected from the group consisting of alkyl, cycloalkyl, alkenyl, alkynyl, aralkyl, CN, CF₃, NO₂, OR⁵¹, —(CH₂)ᵣC(O)(CH₂)ₛR⁵¹, —(CH₂)ᵣC(O)N(R⁵²)(R⁵³), —(CH₂)ᵣC(O)O(CH₂)ₛR⁵¹, —(CH₂)ᵣN(R⁵¹)C(O)R⁵¹, —(CH₂)ᵣN(R⁵²)(R⁵³), —N(R⁵¹)SO₂R⁵¹, —OC(O)N(R⁵²)(R⁵³), —SO₂N(R⁵²)(R⁵³), halo, aryl, and a heterocyclic ring, and additionally or alternatively, two R⁵⁰ groups on adjacent ring atoms form a 5- or 6-membered fused ring which contains from 0 to 3 heteroatoms;
R⁵¹ is selected from H, alkyl, cycloalkyl, alkenyl, alkynyl, aralkyl, aryl, and a heterocyclic ring;
R⁵² and R⁵³ are independently selected from H, alkyl, cycloalkyl, alkenyl, alkynyl, aralkyl, aryl, and a heterocyclic ring; or R⁵² and R⁵³ may be taken together with the nitrogen to which they are attached form a 5- to 7-membered ring which may optionally contain a further heteroatom;
r is 0 to 4;
s is 0 to 4;
m is 0 to 4; and
each R⁰ is independently selected from H, alkyl, cycloalkyl, aralkyl, aryl and a heterocyclic ring.

Exemplary compounds of the formula VI or VIₐ include the following structures:

-continued

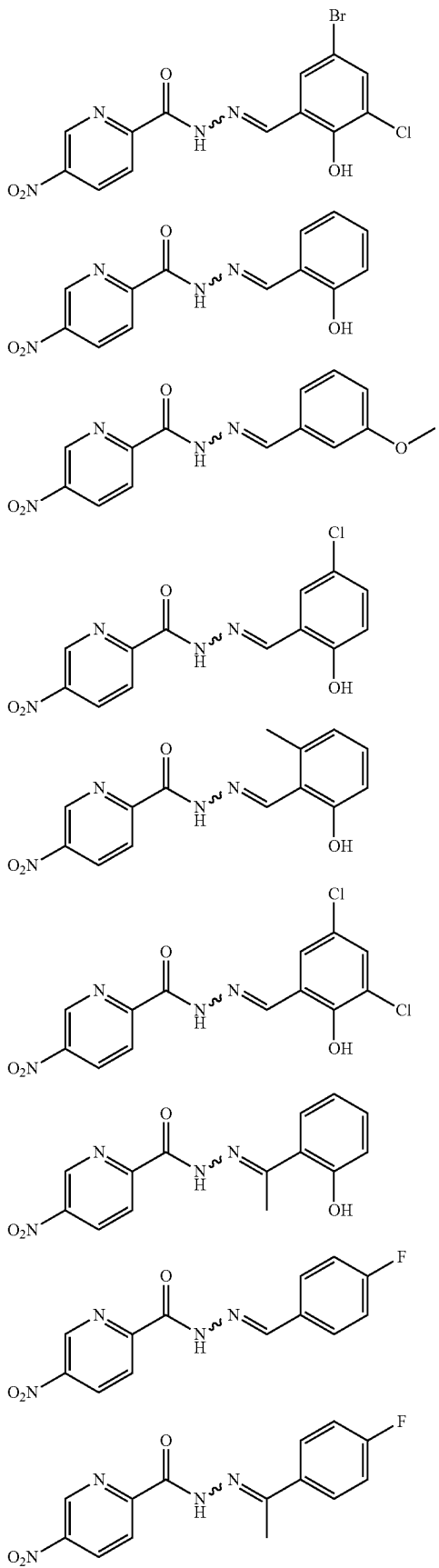

-continued

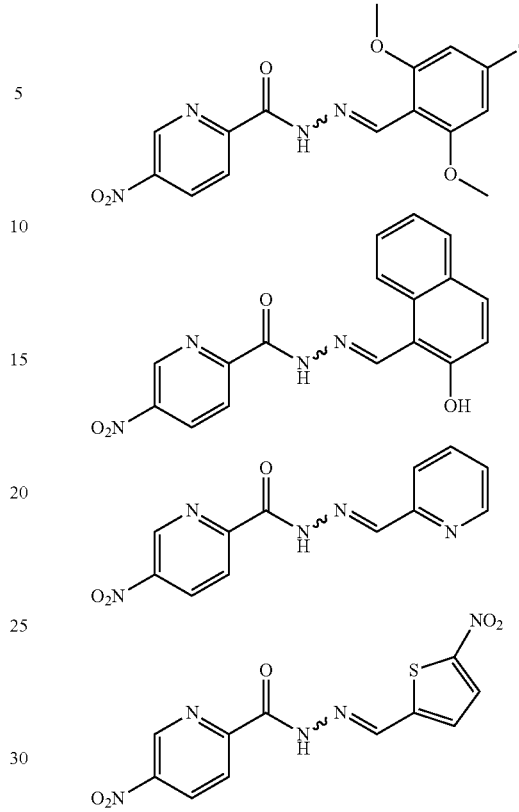

As used herein, the definition of each expression, e.g. alkyl, m, n, R, R' etc., when it occurs more than once in any structure, is intended to be independent of its definition elsewhere in the same structure.

For each of the above descriptions of compounds of the structures I, $I_a$, $I_b$, II, $II_a$, $II_b$, III, $III_a$, IV, $IV_a$, V, $V_a$, VI, and $VI_a$ each recitation of the terms halo, alkyl, cycloalkyl, alkenyl, alkynyl, aralkyl, aryl, heterocyclic group or heterocyclic ring, are independently selected from the definitions of these terms as provided in the beginning of this section.

It will be understood that chemical structures provided herein include the implicit proviso that substitution is in accordance with permitted valence of the substituted atom and the substituent(s), and that the substitution results in a stable compound, e.g., which does not spontaneously undergo transformation such as by rearrangement, cyclization, elimination, etc.

When one or more chiral centers are present in the compounds of the present invention, the individual isomers and mixtures thereof (e.g., racemates, etc.) are intended to be encompassed by the formulae depicted herein.

When one or more double bonds are present in the compounds of the present invention, both the cis- and trans-isomers are intended to be encompassed by the formulae depicted herein. Although chemical structures (such as, for example, structures II, $II_a$, V, $V_a$, VI, and $VI_a$) are depicted herein in either cis of trans configuration, both configurations are meant to be encompassed by the each of the formulae.

In certain embodiments, compounds of the invention may exist in several tautomeric forms. Accordingly, the chemical structures depicted herein encompass all possible tautomeric forms of the illustrated compounds.

The compounds of the invention may generally be prepared from commercially available starting materials and known chemical techniques. Embodiments of the invention may be synthesized as follows. One of skill in the art of medicinal or synthetic chemistry would be readily familiar with the procedures and techniques necessary to accomplish the synthetic approaches given below.

Embodiments wherein $R^2$=NH, $R^3$=N, $R^4$=CH, and $R^5$=aryl may be prepared by reaction of an appropriate hydrazine compound, such as A, and an appropriate aldehyde, such as B, under conditions similar to those described on p. 562 of Gineinah, et al. (Arch. Pharm. Pharm. Med. Chem. 2002, 335, 556-562).

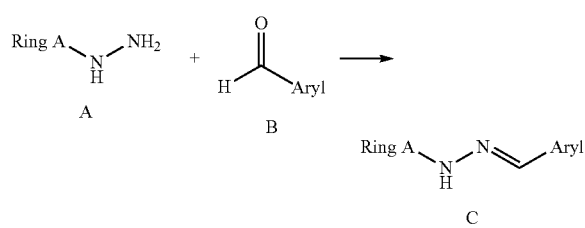

For example, heating A with 1.1 equivalents of B for 1 to 24 hours in a protic solvent such as a $C_1$ to $C_6$ alcohol, followed by cooling and collection of the precipitate, would afford C. Alternatively, product C may be isolated by evaporation of the solvent and purification by chromatography using silica gel, alumina, or $C_4$ to $C_{18}$ reverse phase medium. Similar methodology would be applicable in the cases where "Aryl" is replaced by other groups defined under $R^5$.

Embodiments wherein $R^2$=NH, $R^3$=$NR^{32}$, $R^4$=C(O), and $R^5$=a heterocyclic ring may be prepared by reaction of an appropriate hydrazine compound, such as D, and an activated carboxylic acid such as E, wherein LG is a leaving group such as halo, 1-oxybenztriazole, pentafluorophenoxy, p-nitrophenoxy, or the like, or Compound E may also be a symmetrical carboxylic acid anhydride, whereby conditions similar to those described on p. 408 of Nair and Mehta (Indian J. Chem. 1967 5, 403-408) may be used.

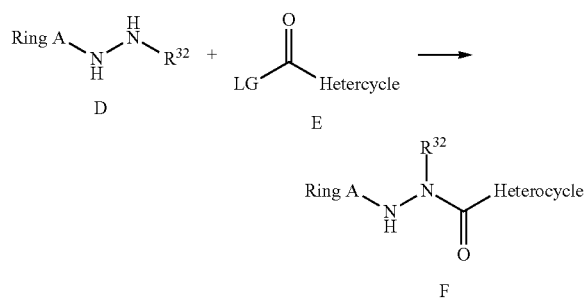

For example, treatment of D with an active ester such as Heterocycle-C(O)—$OC_6F_5$ in an inert solvent such as dichloromethane, 1,2-dichloroethane, or N,N-dimethylformamide, optionally in the presence of a base such as pyridine or another tertiary amine, and optionally in the presence of a catalyst such as 4-N,N-dimethylaminopyridine, at an appropriate temperature ranging from 0° C. to the boiling point of the solvent, would afford F, which may be isolated by evaporation of the solvent followed by chromatography using silica gel, alumina, or $C_4$ to $C_{18}$ reverse phase medium. The above active ester example of E would be readily prepared from the corresponding carboxylic acid and pentafluorophenol using a carbodiimide such as dicyclohexylcarbodiimide as a condensing agent. Similar methodology would be applicable in the cases where "Heterocycle" is replaced by other groups defined under $R^5$.

Precursors such as A and D may be prepared by reaction of an appropriate nucleophile, for example, a hydrazine derivative, with a heteroaromatic compound bearing a halo substituent at a position adjacent to a nitrogen atom. For example, using methods analogous to those described by Wu, et al. (J. Heterocyclic Chem. 1990, 27, 1559-1563), Breshears, et al. (J. Am. Chem. Soc. 1959, 81, 3789-3792), or Gineinah, et al. (Arch. Pharm. Pharm. Med. Chem. 2002, 335, 556-562), examples of compounds A and D may be prepared starting from, for example, a 2,4-dihalopyrimidine derivative, many of which are commercially available or are otherwise readily prepared by one skilled in the art. Thus, treatment of an appropriate 2,4-dihalopyrimidine derivative G with an amine or other nucleophile (Z), optionally in the presence of an added base, selectively displaces the 4-halo substituent on the pyrimidine ring. Subsequent treatment of the product with a second nucleophilic reagent such as hydrazine or a hydrazine derivative, optionally in a solvent such as a $C_1$ to $C_6$ alcohol and optionally in the presence of an added base, displaces the 2-halo substituent on the pyrimidine ring, to afford compounds that are examples of structures A and D above.

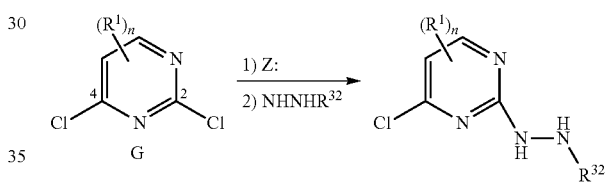

Embodiments wherein $R^2$ is $NR^{22}$ and $R^3$ is —C(=$R^{33}$) can be synthesized by methods such as the following, or straightforward modifications thereof. The synthesis may be conducted starting from an appropriate ring A derivative J that bears a leaving group (LG) adjacent to the requisite ring nitrogen. Structure G above and the product of reaction of structure G with nucleophile Z, as illustrated above, are examples of such appropriate Ring A derivatives J. Suitable LG' groups are halo, alkylthio, alkylsulfonyl, alkylsulfonate or arylsulfonate. Treatment of J with an amine $R^{12}NH_2$ effects displacement of LG' to afford intermediates K. An example of this chemical transformation wherein $R^{12}$ is H and LG' is $CH_3SO_2$— is reported by Capps, et al. J. Agric. Food Chem. 1993, 41, 2411-2415, and an example wherein $R^{12}$ is H and LG' is Cl is reported in Marshall, et al. J. Chem. Soc. 1951, 1004-1015.

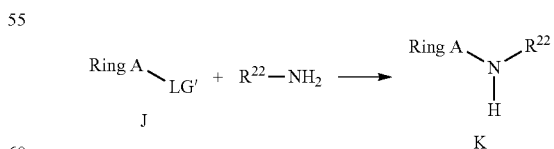

Intermediates of structure K are transformed to compounds of the invention by simultaneous or sequential introduction of the elements, of $R^3$, $R^4$, and $R^5$. For example, treatment of intermediates of structure K with individual isocyanates $R^6$—N=C=O affords in a single step compounds of structure M, which are compounds of the invention wherein $R^2$=—$NR^{22}$—, $R^3$=—C=O—, $R^4$=—NH—, and $R^5$=-chemical bond-$R^6$. Alternative methods to convert compounds of structure K to compounds of structure M are well known to those skilled in the art, wherein $R^3$ together with a leaving group (for example p-nitrophenoxy or chloro) is first introduced, followed by subsequent displacement of the leaving group by, for example, an amine $R^6$—$NH_2$, to introduce $R^5$ and $R^6$.

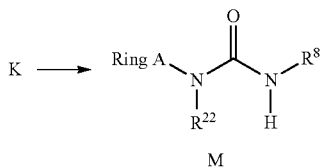

M

Alternatively, treatment of intermediates of structure K with a reagent such as cyanamide ($NH_2$—CN), typically under conditions of heating and optionally in the presence of acid in a solvent such as ethyl acetate or dioxane, affords intermediates N. Alternatives to cyanamide are nitroguanidine or amidinosulfonic acid ($NH_2$—C(=NH)—$SO_3H$). An example of such a transformation using cyanamide is reported by Latham et al., J. Org. Chem. 1950, 15, 884. An example using nitroguanidine is reported by Davis, Proc. Natl. Acad. Sci. USA 1925, 11, 72. Use of amidinosulfonic acid was reported by Shearer, et al. Bioorg. Med. Chem. Lett. 1997, 7, 1763.

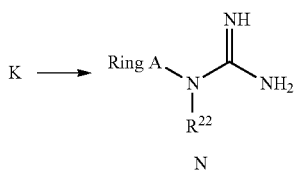

N

In analogy to the conversion of intermediates A or D to embodiments represented by C or F, intermediates K are converted, respectively, to compounds represented by P or Q, which are further embodiments of the invention.

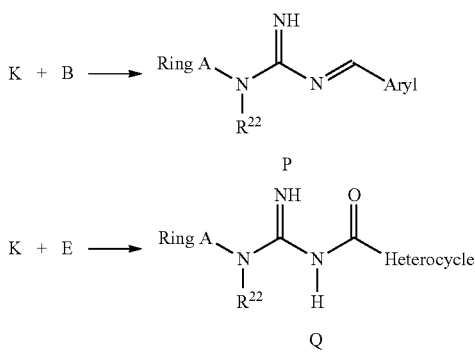

Treatment of A or K with a ketone S, wherein R is as defined above, in place of an aldehyde B in the schemes above, affords compounds of structure T or U, respectively, which are further embodiments of the invention.

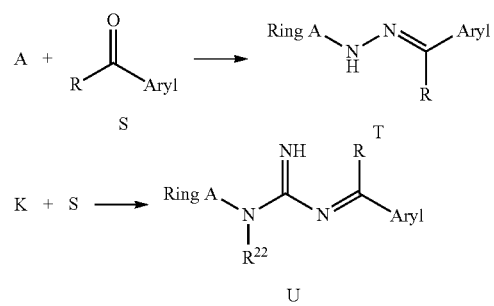

The non-guanidino carbon-nitrogen double bond of U can be selectively reduced by an appropriate reducing agent such as a metal (boron, aluminum, silicon, etc.) hydride reagents, preferably one with basic properties, to afford compounds V of the invention.

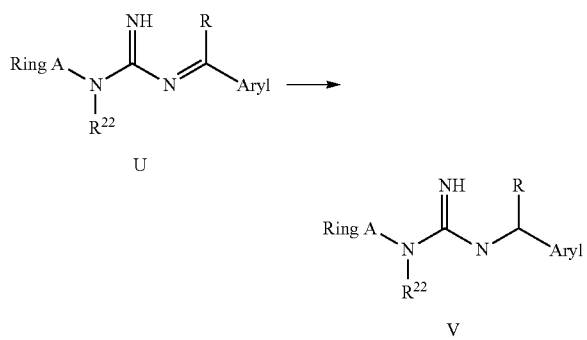

Embodiments of the invention wherein $R^2$=CO, $R^3$=—$NR^{32}$—, $R^4$=N—, and $R^5$=$ZR^7$, wherein Z is a hydrocarbon chain and $R^7$ is as defined above, may be prepared as follows. When $R^{32}$=H, a Ring A-derived carboxylic acid W is activated by conversion to the corresponding acid chloride, or alternatively to an active ester, or to an analogous activated derivative, many of which are well known in the art. Treatment of the activated carboxylic acid with hydrazine affords the corresponding hydrazide Y. Treatment of Y with an aldehyde or ketone (under conditions of heating and/or mild acid catalysis if necessary) affords the desired final product Z.

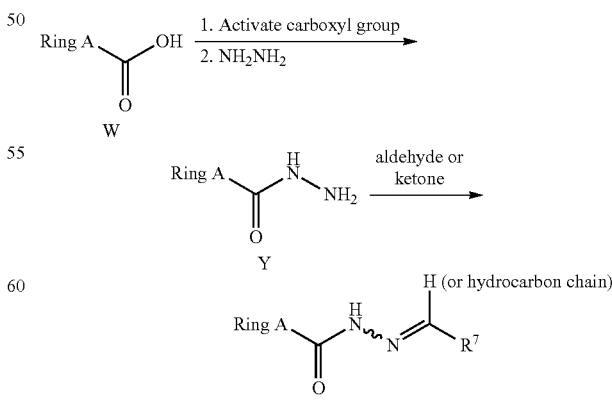

If not commercially available, Ring A-derived carboxylic acids W may be prepared by treatment of starting material J above with cyanide ion, optionally with heating or transition metal catalysis, to replace the leaving group LG' with a cyano residue. Basic or acidic hydrolysis of the cyano group affords the desired carboxylic acid intermediate W.

When $R^{32}$ is not H, then a protected form of monosubstituted hydrazine may be used in the above scheme in place of hydrazine. Thus, treatment of the activated carboxylic acid from W with $R^{32}$NHNH-PG, where PG is a nitrogen protecting group such as benzyloxycarbonyl or t-butyloxycarbonyl, followed by deprotection and treatment with an appropriate aldehyde or ketone as above affords Z', a further embodiment of the invention.

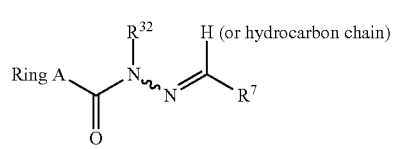

It will be apparent to a practitioner skilled in the art of organic molecule synthesis that the reaction processes illustrated above are representative of a broader set of methods that are logical extensions of the illustrated processes. Thus, additional embodiments of the invention that incorporate additional variants in $R^2$, $R^3$, $R^4$, and $R^5$ claimed by this invention are prepared by obvious modifications of the above processes.

As would be recognized by a person of ordinary skill, it may be advantageous to employ a temporary protecting group in achieving the final product. The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

A "mutein" is a protein having an amino acid sequence that is altered as a result of a mutation that has occurred in its corresponding gene (Weigel et al, 1989). Such mutations may result in changes in one or more of the characteristics of the encoded protein. For example, an enzyme variant that has modified catalytic activity resulting from a change in one or more amino acids is a mutein.

This invention is concerned with proteins harboring an alteration of at least one amino acid residue (the terms "amino acid sequence change" or "amino acid sequence alteration" include changes, deletions, or additions, of at least one amino acid residue, or any combination of deletions, additions, changes) such that the resulting mutein has become (as a result of the mutation) resistant to a known therapeutic agent relative to the sensitivity of the non-mutated version of said protein to the therapeutic agent. This specialized class of muteins is hereinafter referred to as a theramutein, and the corresponding protein lacking the mutation is referred to herein as a prototheramutein.

As used herein, "prototheramutein" refers to an endogenously occurring protein in a cell that is susceptible to mutation that confers relative insensitivity (i.e. resistance) to a therapeutic compound which otherwise inhibits or activates the protein. Accordingly, "theramutein" refers to an endogenously occurring protein or portion of a protein in a cell that contains at least one amino acid sequence alteration relative to an endogenous form of the protein, wherein the amino acid sequence change is or was identified or becomes identifiable, and is or has been shown to be clinically significant for the development or progression of a given disease, following exposure of at least one human being to a substance that is known to inhibit or activate the prototheramutein. Solely for the purposes of defining the preceding sentence, a substance need not be limited to a chemical agent for the purposes of first defining the existence of a theramutein. Thus, by definition, a theramutein is a protein which harbors a mutation in its corresponding endogenous gene, wherein said mutation is associated with the development of clinical resistance in a patient to a drug that is normally able to activate or inhibit the non-mutated protein. With respect to a given theramutein, the term "corresponding prototheramutein" refers to the prototheramutein which, through mutation, gives rise to said theramutein. Similarly, with respect to a given prototheramutein, the "corresponding theramutein" refers to the theramutein which has arisen by mutation from said prototheramutein.

Accordingly, it is apparent to a skilled artisan that, as the genes which encode theramuteins are limited to endogenously occurring genes, the definition of a theramutein excludes proteins encoded by disease-causing infectious agents such as viruses and bacteria. As used herein, the term "endogenous gene" refers to a gene that has been present in the chromosomes of the organism at least in its unmutated form, since inception. The term "cell" as used herein refers to a living eukaryotic cell whether in an organism or maintained under appropriate laboratory tissue or organ culture conditions outside of an organism.

In one aspect of the invention, a theramutein is a protein that is altered for the first time with respect to a commonly occurring "wild type" form of the protein (i.e. the prototheramutein). In another aspect of the invention, a theramutein is a variant of a protein (prototheramutein) that is, itself, already a mutein. In still another embodiment, a theramutein may be further mutated as compared to a previously existing theramutein. In such instances, the first theramutein (such as the T315I mutant of p210 BCR-ABL (see below), may be thought of as a "primary" theramutein, whereas subsequent mutations of the (already mutated) T315I variant may be termed a secondary theramutein, tertiary theramutein, etc. As exemplified below, a mutein of the invention is a variant of Bcr-Abl tyrosine kinase that escapes inhibition by an inhibitor of the "wild type" Bcr-Abl. Such a Bcr-Abl mutein is altered with respect to a more common or "wild type" form of Bcr-Abl (which is also a mutein as well) in such a way that a property of the protein is altered.

It will be understood that a mutein of primary interest is a theramutein that may have the same, increased, or decreased specific activity relative to its prototheramutein, and that it is not inhibited or is poorly inhibited by an agent that is capable of inhibiting the prototheramutein. Likewise, another theramutein of primary interest is one that has the same, increased or decreased specific activity (relative to its prototheramutein) and that is not activated or is poorly activated by an agent that is capable of activating the prototheramutein. Other variations are obvious to the skilled artisan. It will be further appreciated that theramuteins can include naturally occurring or commonly observed variants of a protein, for example, variants that are expressed from different alleles of a particular gene. In some cases such variants may be unremarkable with respect to their normal cellular function, with functional differences becoming apparent only in the presence of agents that differentially inhibit or activate the cellular function of the variants. For example, naturally occurring variants of a particular enzyme may have activity profiles that are not substantially different, but a therapeutic agent that modulates one may be ineffective in modulating the other.

It will be appreciated that, whereas one aspect of the invention is the identification of an agent that is active against a theramutein that arises or becomes dominant (by any mechanism) during the course of a treatment for a given disease, another aspect is the identification of an agent that is active against a mutein that is common within a population of unafflicted individuals, but wherein said mutein is less susceptible to modulation by an approved drug, and where the variation in the activity profile of the mutein becomes important (and is therefore first identified as being a theramutein) in a disease state such as where it is overexpressed or participates in a signaling process which has otherwise become abnormally regulated. For example, a neoplastic disease may be caused by abnormal regulation of a cellular component other than the theramutein or its prototheramutein, and still be treatable with an inhibitor of the prototheramutein, whereas the same treatment would be less effective or ineffective where the theramutein was present. This can be an issue where it is observed that the response of a particular tumor type to an anticancer agent varies among individuals that express different variants of an enzyme against which the anticancer agent is directed (Lynch et al., 2004). Here, the variants would not have arisen or become predominant during the course of treatment of the disease, but are preexisting in the healthy population and are detected only by their altered responsiveness to a particular course of established therapeutic treatment.

As used herein, the terms "agonist" and "activator" of a protein are used interchangeably. An activator (agonist) is limited to a substance that binds to and activates the functioning of a given protein. Unless explicitly stated otherwise, an "activator", an "agonist", and an "activator of a protein" are identical in meaning. The activation by an activator may be partial or complete. Likewise, as used herein, the terms "antagonist" and "inhibitor" of a protein are used interchangeably. An inhibitor (antagonist) is limited to a substance that binds to and inhibits the functioning of a given protein. To state that a substance "inhibit(s)" a protein means the substance binds to the protein and reduce(s) the protein's activity in the cell without materially reducing the amount of the protein in the cell. Similarly, to state that a substance "activate(s)" a protein, such as a prototheramutein or theramutein, is to state that the substance increased the defined function of the protein in the cell without substantially altering the level of the protein in the cell. Unless explicitly stated otherwise, an "inhibitor", an "antagonist" and an "inhibitor of a protein" are also synonymous. The inhibition by an inhibitor may be partial or complete. A modulator is an activator or an inhibitor. By way of example, an "activator of $PKC_{\beta 1}$" should be construed to mean a substance that binds to and activates $PKC_{\beta 1}$. Similarly, an "inhibitor of $p210^{Bcr-Abl}$", is a substance that binds to and inhibits the functioning of $p210^{Bcr-Abl}$ To state that a substance "inhibits a protein" requires that the substance bind to the protein in order to exert its inhibitory effect. Similarly, to state that a substance "activates protein X" is to state that the substance binds to and activates protein X. The terms "bind(s)," "binding," and "binds to" have their ordinary meanings in the field of biochemistry in terms of describing the interaction between two substances (e.g., enzyme-substrate, protein-DNA, receptor-ligand, etc.). As used herein, the term "binds to" is synonymous with "interacts with" in the context of discussing the relationship between a substance and its corresponding target protein. As used herein, to state that a substance "acts on" a protein, "affects" a protein, "exerts its effect on" a protein, etc., and all such related terms uniformly mean (as the skilled investigator is well aware) that said substance activates or inhibits said protein.

The concept of inhibition or activation of a mutated form of an endogenous protein to a greater extent than the corresponding non-mutated counterpart protein is defined for the first time and referred to herein as a positive "specificity gap." In general terms, and using an inhibitor case as an example, the specificity gap refers to the difference between the ability of a given substance, under comparable conditions to inhibit the theramutein in a cell-based assay system as compared to either:

a) the ability of the same substance under comparable conditions to inhibit the prototheramutein, or b) the ability of a second substance (usually a known inhibitor of the prototheramutein) to inhibit the theramutein under comparable conditions, or c) the ability of the second substance to inhibit the prototheramutein under comparable conditions.

When the comparison is made between the effects of two distinct substances (tested individually) on the theramutein alone, the result is termed a homologous specificity gap determination.

Alternatively, when a comparison is made between the effects of two distinct substances (generally, but not always), one of which is tested on the theramutein and the other on the prototheramutein, respectively, the result is termed a heterologous specificity gap (SG) determination. Thus, (a) and (c) as given above are examples of heterologous specificity gap (SG) determinations (although (a) uses the same substance in both instances), whereas (b) is an example of a homologous specificity gap determination.

Figure 3:
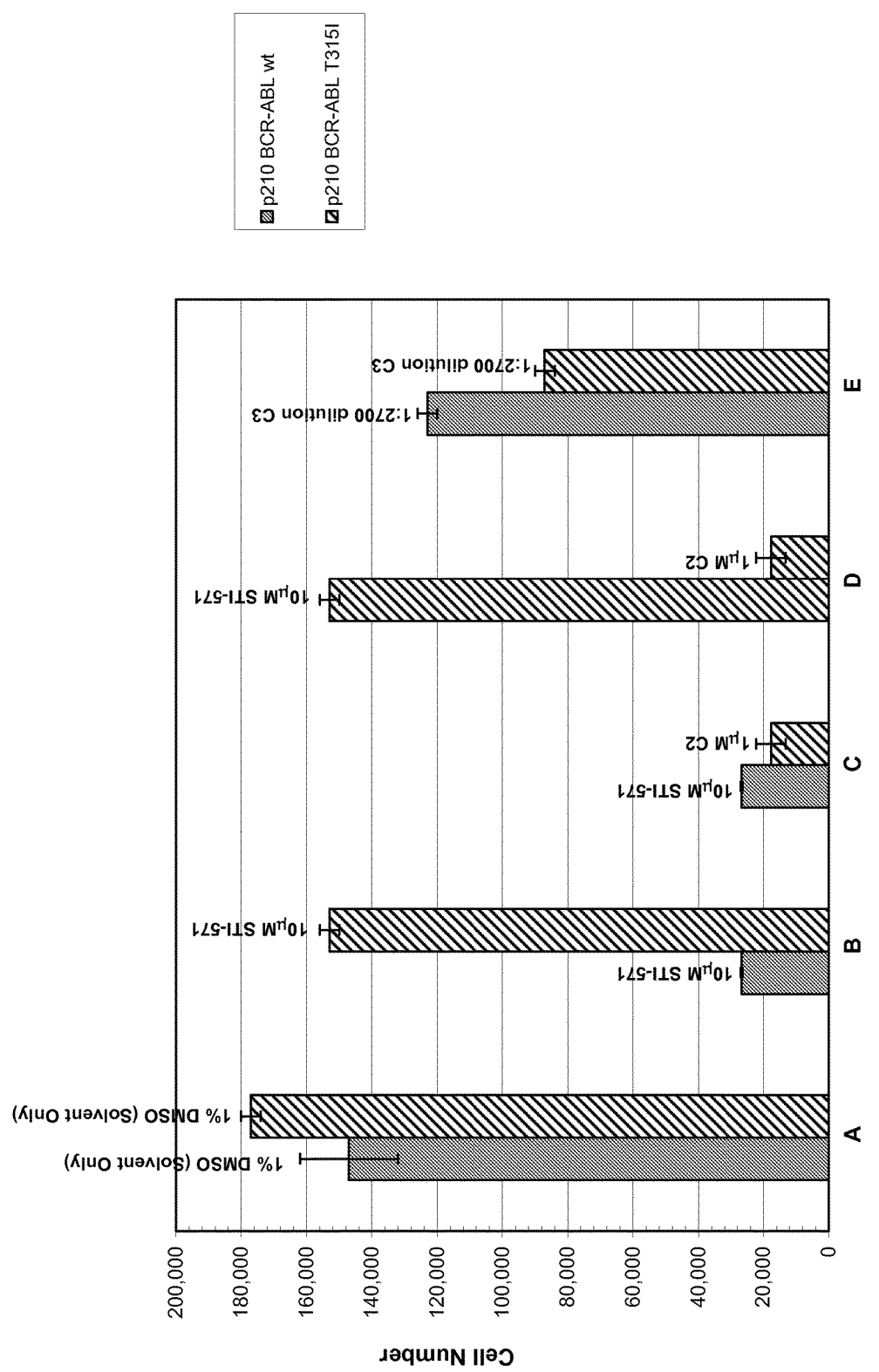
FIG. 3 shows various determinations of the specificity gap by comparing the effects of various compounds identified in the screen in terms of their effects on the prototheramutein- and theramutein-expressing cell lines. Compound 3 (C3) shows the best example of the ability of the method to identify a compound that exerts an even greater effect on the theramutein than on its corresponding prototheramutein. (Panel E). Panel A: control DMSO treatments; B: negative heterologous specificity gap; C: slightly positive heterologous specificity gap; D: large positive homologous specificity gap; E: positive heterologous specificity gap. See text for explanations.

Reference to FIG. 3 is informative in understanding and elucidating these concepts.

Analogous issues apply when the case concerns an activator. It will be immediately obvious to the skilled artisan that the term "comparable conditions" includes testing two different compounds, for example, at the same concentration (such as comparing two closely related compounds to determine relative potency), or by comparing the effects of two different compounds tested at their respective $IC_{50}$ values on the corresponding prototheramutein and theramutein. The skilled investigator will easily recognize other useful variations and comparable conditions.

Thus, in one embodiment of the application of this approach, substances that are more effective against a theramutein have a "positive specificity gap." A "zero, null or no" specificity gap indicates that there is no significant measurable difference between the effect of a substance on the theramutein as compared to its effect on the prototheramutein (however such compounds may be quite useful in their ability to inhibit or activate both a theramutein and its corresponding prototheramutein), and a "negative specificity gap" indicates a substance that at a given concentration is less effective against the given theramutein than against a form of the corresponding prototheramutein or other comparative form of the theramutein (such as one that may harbor a different mutation). The latter category is generally of lesser interest than the former categories of compounds, except in the case where the compound is so potent that its relatively lesser effect on the theramutein is of no real concern from the perspective of therapeutic efficacy. The skilled investigator can easily recognize a variety of approaches to quantifying the specificity gap assessment in a manner tailored to his or her needs.

The invention also provides a means for identifying compounds that exhibit a desired specificity gap. Such compounds can be identified and their ability to inhibit or activate the theramutein determined using an in vitro cell-based assay system where the effect of a substance on the cellular functioning of the mutated endogenous form of the protein is compared to the effect of the same drug on the cellular functioning of a non-mutated endogenous form of the protein.

Thus, the system enables the discovery of compounds capable of binding to a theramutein and exerting a greater modulatory effect on the cellular functioning of said theramutein than on its corresponding prototheramutein. Further, the system enables the discovery of compounds capable of binding to a theramutein and exerting at least as great or greater modulatory effect on the cellular functioning of a theramutein than previously known compounds are able to exert on the corresponding prototheramutein. In a particular embodiment of the invention, a compound may be screened for and identified that 1) is at least as effective against the theramutein as the original drug is against the prototheramutein, and/or 2) is similarly effective against the prototheramutein as against the theramutein (i.e., displays a small or essentially zero specificity gap).

In an embodiment of the invention, cells that overexpress a theramutein of interest are used to identify chemical agents that are inhibitors or activators of (i.e., that bind to and inhibit or that bind to and activate) at least the selected theramutein. The chemical agents may also be inhibitors or activators of the prototheramutein or even other theramuteins of the same prototheramutein. As used herein, the terms "chemical agent" and "compound" are used interchangeably, and both terms refer exclusively to substances that have a molecular weight up to, but not including, 2000 atomic mass units (Daltons). Such substances are sometimes referred to as "small molecules." Unless otherwise stated herein, the term substance as used herein refers exclusively to chemical agents/compounds, and does not refer to biological agents. As used herein, "biological agents," are molecules which include proteins, polypeptides, and nucleic acids, and have molecular weights equal to or greater than 2000 atomic mass units (Daltons).

According to the invention, a theramutein is selected and used in a cell-based assay system designed to identify agents that are inhibitors or activators of the theramutein. Where two or more distinct theramuteins originating from the same prototheramutein are known, it is preferable to select the most resistant theramutein available for use in the assay system. In general, the degree of resistance of a theramutein to a given chemical agent is determined relative to its non-mutated counterpart (prototheramutein) using the drug that was first administered and known to inhibit or activate the prototheramutein and against which the theramutein "arose." The methods of determining the degree of such resistance, for example by analysis of $IC_{50}$ or $AC_{50}$ values, are well known and standard in the art and will not be reiterated herein. However, no causal relationship is necessary or should be inferred between the treatment of the patient with a given therapeutic agent per se and the subsequent appearance of a theramutein. Rather, what is required in order to practice the invention is that a true theramutein be properly selected according to the teachings herein.

Thus, for example, randomly generated site directed mutants of known proteins that are created in the laboratory but that have not been shown to be clinically relevant are not appropriate muteins for use within the scope of this invention. Such muteins would not, of course, be properly classified as theramuteins.

For example, in an effort to obtain potential inhibitors of mutants of $p210^{Bcr-Abl}$, Huron et al. (2003) used a recombinant c-abl preparation and screened a series of compounds known to inhibit c-src tyrosine kinase activity. The authors performed c-abl kinase assays on their compounds and identified the most potent compound as an 8 nM inhibitor against c-abl. When this compound (PD166326) was tested against various $p210^{Bcr-Abl}$ theramuteins, however, it showed activity against some of the mutants such as $p210^{Bcr-Abl-E255K}$, but the $p210^{Bcr-Abl-T315I}$ theramutein was found to remain 10 fold more resistant (Huron et al. 2003, Table 3). Furthermore, in each case the compound was still markedly less effective on the $p210^{Bcr-Abl}$ theramuteins than it was against the wild-type $p210^{Bcr-Abl}$. When the compound was tested against $p210^{Bcr-Abl-T315I}$ mutant activity, it was unable to inhibit the activity to any appreciable extent (p. 1270, left hand column, second paragraph; see also FIG. 4). Thus, the disclosed compound was able to inhibit a theramutein that is partially resistant to STI-571, but had no activity against the T315I mutant of Bcr-Abl., which was already known at that time to be the theramutein that exhibited the most resistance to STI-571. Hence purely and simply, the Huron methodology failed to identify an effective inhibitor of the $p210^{Bcr-AblT315I}$ theramutein.

Indeed, prior to the disclosure of this invention, including both the detailed methodology described for the first time herein as well as the compositions provided herein, no one anywhere in the world has been successful in identifying a chemical agent, let alone a methodology that is capable of identifying a chemical agent that effectively inhibits the $p210^{Bcr-AblT315I}$ theramutein to an equal or greater extent than STI-571 is able to do with respect to the wild type $p210^{Bcr-Abl}$ protein. (See Shah et al., Science, July, 2004; O'Hare et al., Blood, 2004; Tipping et al., Leukemia, 2004; Weisberg et al., Leukemia, 2004).

It cannot be overemphasized that such compounds would be immensely useful, because at the present time there is no alternative for patients who progress to $p210^{Bcr-Abl-T315I}$ theramutein-mediated imatinib mesylate-resistant status. Once patients develop such resistance, there is no other effective alternative treatment available, and death is certain. The method described herein provides the first reported approach to identify, pharmacologically characterize and chemically synthesize effective inhibitors of the $p210^{Bcr-Abl-T315I}$ theramutein. Moreover, the skilled investigator will immediately recognize the applicability and generalizability of this approach to any highly drug-resistant theramutein.

In the present invention, a test cell is used that displays a carefully selected phenotypic characteristic (as defined below) which is linked to the presence and functional activity of the particular theramutein-of-interest (TOI) in the cell under appropriate conditions. This should be qualitatively the same as the phenotypic characteristic displayed by a cell that expresses the prototheramutein. A phenotypic characteristic (i.e. a non-genotypic characteristic of the cell) is a property which is observed (measured), selected and/or defined for subsequent use in an assay method as described herein. Expression of the phenotypic characteristic is responsive to the total activity of the theramutein in the cell, and is a result of the absolute amount of the theramutein and its specific activity. Often, the phenotypic characteristic is observable as a result of elevated levels of theramutein activity and is not apparent in cells that express low amounts of the theramutein or low amounts of its corresponding prototheramutein. Further, it can often be demonstrated that the phenotypic characteristic is modulated by modulating the specific activity of the theramutein with an inhibitor or activator of the theramutein, although this is not always the case since an inhibitor or activator of the TOI may not always be available at the time the skilled investigator undertakes such a project. Thus, for the purpose of defining the phenotypic characteristic to be subsequently used with a given test cell for assay purposes, the skilled investigator may also use a substance capable of increasing or decreasing the expression of the theragene, which will in turn lead to increases or decreases of the level of the corresponding theramutein. This allows the skilled investigator to simulate the effects of certain types of activators or inhibitors of the theramutein (such as a suicide inhibitor of the theramutein, which is a class of chemical agent which binds irreversibly and covalently modifies the TOI, rendering it permanently inactive), without actually having access to such a compound, for the purposes of refining the appropriate phenotypic characteristic for subsequently establishing a useful cellular assay system. Examples known to one of ordinary skill that would be helpful for such purposes include the use of anti-sense DNA oligonucleotides, small interfering RNAs, other RNA interference-based methodologies, and vector constructs containing inducible promoter systems. In this manner, the selected phenotypic characteristic is linked to the activity of the theramutein in the test cell. Notably for theramuteins, the selected phenotypic characteristic is usually also displayed by a cell that overexpresses the prototheramutein and in which the phenotypic characteristic is modulated by known inhibitors or activators of the prototheramutein.

A phenotypic characteristic is simply a characteristic of a cell other than a genotypic characteristic of the cell. Except for the specific requirements of a properly defined phenotypic characteristic as disclosed herein for the purposes of creating useful cellular assay systems according to the teachings of certain of the embodiments of the invention, no other limitation of the term phenotypic characteristic of any kind or nature is intended or appropriate in order to properly and effectively practice the invention. Indeed, the skilled artisan must be able to select any characteristic of the cell that maximizes the utility of establishing the proper cell-based assay for his or her needs. The phenotypic characteristic can be quantitative or qualitative and be observable or measurable directly (e.g., observable with the naked eye or with a microscope), but most commonly the characteristic is measured indirectly using standard automated laboratory equipment and assay procedures which are known to those of skill in the art. The term "observable" means that a characteristic may be measured or is otherwise detectable under appropriate conditions by any means whatsoever, including the use of any type of laboratory instrumentation available. The term "detectable" is not the same as "detected". A characteristic may be detectable to a skilled artisan without being detected at any given time, depending upon how the investigator chooses to design the assay system. For example, in searching for activators of a prototheramutein (or theramutein), it may be desirable to have the relevant phenotypic characteristic detected only after the addition of a known activator or test substance capable of activating the POI. This provides the ability to maximize the intensity of the signal that is generated by the test cell in the assay.

Phenotypic characteristics include but are not limited to growth characteristics, transformation state, differentiation state, substrate phosphorylation state, catalytic activity, ion flux across the cell membrane (calcium, sodium, chloride, potassium, hydrogen ions, etc.), pH changes, fluctuations of second messenger molecules or other intracellular chemical species such as cAMP, phosphoinositides, cyclic nucleotides, modulations of gene expression, and the like. The characteristic of the cell may be observable or measurable continuously (e.g., growth rate of a cell), or after a period of time (e.g., terminal density of a cell culture), or transiently (e.g., modulation of a mutein causes a transient change in phosphorylation of a substrate of the mutein, or a transient flux in ion flow across the membrane, or elevations or reductions in intracellular cAMP levels). In certain embodiments, a selected phenotypic characteristic may be detected only in the presence of a modulator of the prototheramutein or the theramutein. No limitations are intended with respect to a characteristic that may be selected for measurement. As used herein, the terms "characteristic of a cell" and "phenotypic characteristic", and simply "characteristic", when used to refer to the particular measurable property of the intact cell or a subcellular fraction of the cell following the treatment of a test cell with a substance, are identical. For example, a phenotypic characteristic can be focus formation that becomes observable when a cell that over expresses a selected protein is cultured in the presence of an activator of the protein, or it may be a transient increase or decrease in the level of an intracellular metabolite or ion, such as cAMP, calcium, sodium, chloride, potassium, lithium, phosphatidylinositol, cGMP, bicarbonate, etc. It is obvious to one of ordinary skill in the art that after a cell is exposed to a test substance, the characteristic so measured (assayed) may be determined on a sub-cellular fraction of the cell. However, the initial treatment of the cell with a substance, which thereby causes the substance to come into contact with the cell, must be performed on the intact cell, not a sub-cellular fraction.

The characteristic selected for measurement within the cell must not be an intrinsic physical or chemical property of the theramutein or prototheramutein itself (such as the mere amount (mass) of the protein inside the cell), but rather must be a characteristic that results from the activity of the theramutein inside the cell, thus affecting a characteristic of the cell which is distinct from the theramutein itself, as discussed in detail above. For example, where the theramutein is a protein kinase that is capable of undergoing autophosphorylation, a process whereby the enzyme is capable of catalyzing the phosphorylation of itself by transferring a terminal phosphate group from ATP onto itself, it would NOT be appropriate to select the phosphorylation state of the TOI as an appropriate phenotypic characteristic of the cell for measurement. This is because such a characteristic does not reflect the activity of the TOI on other cellular components. As the skilled investigator knows, autophosphorylation is not necessarily reflective of the activity of a protein kinase in a cell, since mutants of protein kinases are known that retain enzymatic activity sufficient to undergo autophosphorylation, yet have lost the capability to engage in signal transduction events within the cell. The classic paper by White et al. (1988) is both educational and noteworthy in this respect.

The term "responsive phenotypic characteristic" means a characteristic of the cell which is responsive to inhibitors or activators of a given protein (prototheramutein or theramutein). The term "known therapeutic agent" is defined as any agent that has been administered to a human being for the treatment of a disease in a country of the world.

A useful phenotypic characteristic, as exemplified herein in association with $p210^{Bcr-Abl}$ and theramuteins thereof, is disregulation of cell growth and proliferation. It is noted that the same or similar assay may be appropriate for use with many different proteins of interest. For example, disregulations of growth, proliferation, and/or differentiation are common phenotypic characteristics that may result from overexpression of a variety of different cellular proteins. It is an important teaching of this invention that by overexpressing a selected protein in order to cause the appearance of such a phenotypic characteristic, the characteristic becomes linked to the presence, amount, and specific activity of that selected protein under suitable conditions, and this linkage allows the skilled investigator to identify inhibitors or activators of a theramutein of interest (TOI) as desired. Accordingly, the phenotypic characteristic is responsive to changes in the level and/or specific activity of the selected protein. Such a responsive phenotypic characteristic is referred to herein as a "phenoresponse."

Though not always necessary, it will often be advantageous to employ cells that express high levels of the theramutein, and to select a phenotypic characteristic that results from overexpression of the theramutein. This is because phenotypic characteristics linked to the functioning of the theramutein generally become more distinguishable (easier to measure) as a theramutein is overexpressed to a greater extent. Further, phenoresponses that are observed in response to modulators of the theramutein are often amplified as the functional level of the theramutein is increased. Expressed another way, the selected phenoresponse observed in cells that overexpress the theramutein is particularly sensitive to modulators of the theramutein.

Preferably, the theramutein is stably expressed in a test cell. Stable expression results in a level of the theramutein in the cell that remains relatively unchanged during the course of an assay. For example, stimulation or activation of a component of a signaling pathway may be followed by a refractory period during which signaling is inhibited due to down-regulation of the component. For theramuteins of the invention, such down-regulation is usually sufficiently overcome by artificially overexpressing the theramutein. Expressed another way, the expression is sufficiently maintained that changes in a phenotypic characteristic that are observed during the course of an assay are due primarily to inhibition or activation of the theramutein, rather than a change in its level, even if down-modulation of the theramutein subsequently occurs. For these reasons, although stable expression of the theramutein is preferred, transfection followed by transient expression of the theramutein may be employed provided that the selected phenotypic characteristic is measurable and the duration of the assay system is short relative to the progressive decline in the levels of the transiently expressed theramutein which is to be expected in such systems over time. For these reasons, stably expressing cell lines are preferred (U.S. Pat. No. 4,980,281).

A preferred drug screening method of the present invention involves the following:

1) Identification of a theramutein for which a novel inhibitor or activator is desired. Identification of an appropriate theramutein may be performed using standard techniques (See, Gone et al., Science, 2001; see also PCT/US02/18729). Briefly, patients that have been given a course of a therapeutically effective treatment using an activator or inhibitor of a known or suspected prototheramutein and have subsequently shown clinical signs and symptoms consistent with disease relapse are identified, and cells or tissue samples derived from such patients are obtained. Using standard laboratory techniques such as RT-PCR, the sequence of the prototheramutein is determined and compared to the previously determined nucleic acid sequence of the known prototheramutein gene or cDNA sequence. Mutations, if present, are identified and are correlated with functional resistance of the prototheramutein's function either in cell-based or, more commonly, cell-free assay systems, again using standard methodology. Once resistance-inducing mutations are confirmed, then said one or more confirmed mutants comprise a defined theramutein which may be used in the subsequent methods as described herein.

2) Provision of a test cell that expresses a theramutein of interest and displays an observable (measurable) phenotypic characteristic which has been previously shown to be responsive to inhibitors or activators of the theramutein or, more commonly, the corresponding prototheramutein. Said specific phenotypic characteristic that has been previously shown to be responsive to inhibitors or activators of the theramutein-of-interest (TOI), and/or the prototheramutein-of-interest (pTOI) is defined herein for the first time as a "phenoresponse." One embodiment of this invention is the definitive use of the phenoresponse for the purpose of identifying compounds that are likely to be inhibitors or activators of the TOI. This may be accomplished through the use of a high-throughput screen using a cell line overproducing a given TOI and for which an appropriate phenoresponse has been identified and characterized. Alternatively, one may utilize a high-throughput primary screen using a more generic phenotypic characteristic of a cell line (that does not qualify as a phenoresponse according to the teachings herein) and then utilize a secondary screen according to the teachings herein to distinguish between compounds that are true positive "hits", i.e. inhibitors or activators of the theramutein of interest, from false positive compounds that are not inhibitors or activators of the theramutein of interest. In one embodiment, a cell is selected that naturally expresses the theramutein such that a responsive phenotypic characteristic is present under suitable culture conditions which are obvious to one of ordinary skill in the art. In other embodiments, the theramutein is overexpressed, in some instances in a host cell that does not otherwise express the theramutein at all. This usually involves construction of an expression vector from which the theramutein can be introduced into a suitable host cell and overexpressed using standard vector systems and methodology. (Gone et al., 2001; Housey et al., 1988). In one embodiment, overexpression results in a level of the theramutein that is at least about 3 times the amount of the protein usually present in a cell. Alternatively, the amount is at least about 10 times the amount usually present in a cell. In another embodiment, the amount is at least about 20 times or more preferably at least about 50 times the amount usually present in a cell.

3) Provision of a control cell that expresses the prototheramutein corresponding to the theramutein of interest. As some of the muteins that are described herein are also enzymes, they usually retain catalytic activity, and therefore the control cell usually displays substantially the same phenotypic characteristic as the test cell. The phenotypic characteristic need not be quantitatively alike in both cells, however. For example, a mutation that leads to reactivation of the prototheramutein may also increase, decrease, or otherwise affect its specific activity with respect to one or more of its substrates in the cell. As a result, it may exhibit the selected phenotypic characteristic to a greater or lesser extent. Accordingly, it may be desirable in some cases to adjust expression of either or both of the prototheramutein and the theramutein such that test and control cells exhibit the phenotypic characteristic to approximately the same degree. This may be done, for example, by expressing the proteins from promoters whose activity can be adjusted by adjusting the amount of inducer present, all using standard methodology (see, for example, Sambrook et al. 1989 & 2001).

It will be obvious to one of ordinary skill in the art that a properly defined phenoresponse may be quantitatively different between the prototheramutein- and the theramutein-expressing cell lines as a result of differences in the specific activity (if any) between the theramutein and its corresponding prototheramutein. Theramutein-inducing mutations may increase or decrease the specific activity of said theramutein relative to the corresponding prototheramutein. When comparing a theramutein expressing cell line with a prototheramutein expressing cell line, it is preferable that the selected phenoresponse is qualitatively the same in both cell types. Thus, the skilled investigator may choose to normalize the activity of the theramutein-expressing cell line to that of the prototheramutein-expressing cell line, or vice versa. Such normalization methods are standard in the art. See, for example, Bolstad et al. (2003).

Alternatively, the skilled investigator may also wish to use unmodified host cells or host cells harboring the expression vector only as control cells for certain experimental procedures. (The host cells are the cells into which an expression vector encoding the theramutein was introduced in order to generate the test cells.) This may be the case where the investigator is only interested in identifying a specific inhibitor or activator of the theramutein of interest, irrespective of whether or not said compound is also effective the prototheramutein of interest (pTOI).

4) The test and control cells are then maintained or propagated (although not necessarily at the same time) in growth media (or even in intact animals) under suitable conditions such that the phenoresponse may be expressed and assayed. Control cells that are expressing the prototheramutein may be treated with a known modulator of the prototheramutein, or with a test substance, and test cells are treated with test compounds to determine whether they are active against the theramutein, as measured by the ability of said substances to modulate the phenoresponse in the expected manner. Alternatively, control cells not expressing the prototheramutein may also be substituted, depending upon the particular phenoresponse that the skilled investigator has chosen for study. Substances may then be assayed on the test cells and, optionally, on the control cells at the same time, or at another time, and the results compared.

In one embodiment of the invention, substances that are active with regard to the test cells can be rapidly identified by their ability to modulate the phenoresponse of the test cells in the same manner as, for example, the known modulator of the prototheramutein alters the phenoresponse of prototheramutein-expressing control cells. In another embodiment, active substances may be identified by their ability to modulate the activity of the theramutein in the test cells while having little or no effect on the unmodified (prototheramutein and/or theramutein non-expressing) control cells. The skilled investigator will readily appreciate the many variations of this approach that may be utilized to identify, for example, modulators that are more effective against the theramutein, or that are equally effective against both the prototheramutein and one or more corresponding specific theramuteins.

Other phenoresponses can be observed and/or measured and include, for example, detection of substrates of the prototheramutein, and detection of gene expression changes that are regulated by the activity of the theramutein. In the simplest terms, any characteristic of the cell that the skilled investigator has previously correlated with the functional activity of the theramutein may be suitable for use with such methods. However, in selecting a given characteristic, the skilled investigator must first verify that said characteristic fulfills the criteria of being a phenoresponse according the teachings as given in detail herein. The skilled investigator may also wish to normalize the phenoresponse with the theramutein expressing cells to that of the prototheramutein expressing cells.

Characteristics suitable for detection may be measured by a variety of methods very well known to those of skill in the art. Such methods include, but are not limited to, detection of fluorescence of suitably labeled proteins (FACS), immunohistochemistry (IHC) for detection of protein expression, competitive radioligand binding assays, solid matrix blotting techniques, such as Northern, Southern, and Western blots of cell extracts, reverse transcriptase polymerase chain reaction (RT-PCR), enzyme linked immunosorbent assays (ELISA), phosphorylation assays, gel retardation assays, membrane potential perturbations, and the like. The relevant phenotypic characteristic may be detected either on the intact cell after treatment with a test substance or, alternatively, on a subcellular fraction of the cell after treatment of the intact cell with a test substance.

Once compounds are identified that have the desired effect on the theramutein expressing test cells, it may be desirable (but not necessary) to independently verify that the compounds identified are exerting their effects on the theramutein through a direct binding mechanism, i.e. that the compounds fulfill the criteria of being inhibitors or activators (as desired) of the theramutein according to the teachings of the invention (the reader is referred to the definitions of the terms "activator" and "inhibitor" as given above). This may be accomplished with numerous standard binding assays that are known to one of ordinary skill in the art, involving either purified protein samples or intact cellular binding assays using cells transfected with the appropriate prototheramutein or theramutein together with appropriate controls as dictated by sound scientific methods. Since such methods are well established in the art they will not be reiterated here. Numerous reference texts comprehensively discuss such techniques (see, for example, Foreman and Johansen, 2002; Enna S. J. et al. (1991) Current Protocols in Pharmacology, Wiley & Sons, Incorporated; Bonifacino, J. S. et al. (1999) Current Protocols in Cell Biology, Wiley & Sons, Incorporated). See also Housey, G. M. 1988, Chapter 4, and references therein; see also Horowitz et al., 1981.

In a particular embodiment of the invention, the method is used to identify substances that are inhibitors of the $p210^{Bcr-Abl-T315I}$ theramutein. The prototheramutein and theramutein are each expressed in Ba/F3 (murine) cells using standard methodology and the phenoresponses that are observed are growth characteristics (terminal cell density for a carefully defined cell culture, and growth in the absence of Interleukin-3 (IL-3). Unmodified host cells, or host cells containing the expression vector only or both, may optionally also be used. In still another embodiment, the test cells alone may be used with or without reference to a known inhibitor or activator.

Another useful assay is the determination of the state of phosphorylation of a direct substrate of $p210^{Bcr-Abl-T315I}$. One such substrate is Crkl (Gorre et al., Science 293:876-80

(2001)), an adapter protein which mediates the connection between Bcr-Abl and Ras. The phosphorylation state of CRKL is representative of the signaling activity of $p210^{Bcr-Abl}$ in a cell. Another downstream substrate is p62DOK. Any such substrate would suffice for these purposes, provided of course that phosphorylation of said substrate has been shown to occur inside the cell, and is not simply an autophosphorylation event of the TOI or PTOI as discussed above. Other signal transduction cascade components may also be monitored, including src family kinases, STATS, PI3 Kinase, raf kinase, RAS, MEK, ERK1 and ERK2, JNK1, 2 and 3, MLK1, 2 and 3, MKK4, MKK7, AKT, mTOR, HSP90, and others.

As exemplified herein, inhibitors of the T315I theramutein have been identified. Furthermore, these inhibitors are also active to differing extents against the wild type prototheramutein $p210^{Bcr-Abl-wt}$.

According to the present invention, a therapeutically effective amount of one or more compounds that modulate the functional activity of a $p210^{Bcr-Abl}$ theramutein is administered to a mammal in need thereof. The term "administering" as used herein means delivering the compounds of the present invention to a mammal by any method that may achieve the result sought. They may be administered, for example, orally, parenterally (intravenously or intramuscularly), topically, transdermally or by inhalation. The term "mammal" as used herein is intended to include, but is not limited to, humans, laboratory animals, domestic pets and farm animals. "Therapeutically effective amount" means an amount of a compound that, when administered to a mammal, is effective in producing the desired therapeutic effect, such as inhibiting kinase activity, inhibiting cancer cell growth and division, etc.

The invention provides a method of treating disease in a mammal by administering to the mammal an effective amount of a modulator of a theramutein. Suitable diseases to be treated according to the present invention include, but are not limited to, relapsing neoplastic or other proliferative disorders that have become resistant to previously administered drugs. The method is also useful for overcoming variation among individuals with respect to susceptibility to drug treatment that results from allelic differences among therapy targets. For example, the role of $p210^{Bcr-Abl}$ tyrosine kinase signaling in CML has been extensively demonstrated, as has the role of theramuteins of $p210^{Bcr-Abl}$ in drug resistant recurrence of CML. Further, different muteins of $p210^{Bcr-Abl}$ exhibit varying sensitivity to inhibitors of $p210^{Bcr-Abl}$. Although some theramuteins arise during drug therapy, others may preexist in the population. These latter examples will not be recognized as theramuteins until such time as the disease state ensues and is followed by treatment with a known class of therapeutic agents. Only after said treatment will such preexisting theramuteins reveal themselves as being clinically significant in terms of relative non-responsiveness leading to the progression of the disease in the patient harboring the theramutein.

In an embodiment of the invention, theramutein modulators are administered in combination with one or more other anti-neoplastic agents. Any suitable anti-neoplastic agent can be used, such as a chemotherapeutic agent, radiation or combinations thereof. The anti-neoplastic agent can be an alkylating agent or an anti-metabolite. Examples of alkylating agents include, but are not limited to, cisplatin, cyclophosphamide, melphalan, and dacarbazine. Examples of anti-metabolites include, but not limited to, doxorubicin, daunorubicin, and paclitaxel, gemcitabine, and topoisomerase inhibitors irinotecan (CPT-11), aminocamptothecin, camptothecin, DX-8951f, topotecan (topoisomerase I inhibitor), and etoposide (VP-16; topoisomerase II inhibitor) and teniposide (VM-26; topoisomerase II inhibitor). When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity of the tumor being treated and the route of administration of the agent. It should be emphasized, however, that the present invention is not limited to any particular dose, route of administration, or combination of chemotherapeutic agents or other therapeutic regimens that are combined with the administration of theramutein modulators.

Anti-neoplastic agents which are presently known in the art or being evaluated can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti survival agents, biological response modifiers, anti-hormones, and anti-angiogenesis agents, all of which can be administered with inhibitors or activators of theramuteins.

A modulator of a theramutein can be administered with antibodies that neutralize other receptors involved in tumor growth. Further, a modulator of a theramutein can be administered with a compound that otherwise modulates a component of a signal transduction pathway, preferably a component of the signal transduction pathway in which the theramutein is active and which is common to one or more other signal transduction pathways. In an embodiment of the invention, a theramutein modulator is used in combination with a receptor antagonist that binds specifically to the Epidermal Growth Factor Receptor (EGFR). Particularly preferred are antigen-binding proteins that bind to the extracellular domain of EGFR and block binding of one or more of its ligands and/or neutralize ligand-induced activation of EGFR. An EGFR antagonist can be an antibody that binds to EGFR or a ligand of EGFR and inhibits binding of EGFR to its ligand. Ligands for EGFR include, for example, EGF, TGF-α, amphiregulin, heparin-binding EGF (HB-EGF) and betacellulin. EGF and TGF-α are thought to be the main endogenous ligands that result in EGFR-mediated stimulation, although TGF-α has been shown to be more potent in promoting angiogenesis. It should be appreciated that the EGFR antagonist can bind externally to the extracellular portion of EGFR, which can or can not inhibit binding of the ligand, or internally to the tyrosine kinase domain in the case of chemical agents. Examples of EGFR antagonists that bind EGFR include, without limitation, biological agents such as antibodies (and functional equivalents thereof) specific for EGFR, and chemical agents (small molecules), such as synthetic kinase inhibitors that act directly on the cytoplasmic domain of EGFR.

Other examples of growth factor receptors involved in tumorigenesis are the receptors for vascular endothelial growth factor (VEGFR-1 and VEGFR-2), platelet-derived growth factor (PDGFR), nerve growth factor (NGFR), fibroblast growth factor (FGFR), and others.

In a combination therapy, the theramutein inhibitor is administered before, during, or after commencing therapy with another agent, as well as any combination thereof, i.e., before and during, before and after, during and after, or before, during and after commencing the anti-neoplastic agent therapy. For example, the theramutein inhibitor can be administered between 1 and 30 days, preferably 3 and 20 days, more preferably between 5 and 12 days before commencing radiation therapy. In a preferred embodiment of the invention, chemotherapy is administered prior to, concurrently with or, more preferably, subsequent to antibody therapy.

In the present invention, any suitable method or route can be used to administer theramutein inhibitors of the invention, and optionally, to co-administer anti-neoplastic agents and/or antagonists of other receptors. The anti-neoplastic agent regimens utilized according to the invention, include any regimen believed to be optimally suitable for the treatment of the patient's neoplastic condition. Different malignancies can require use of specific anti-tumor antibodies and specific anti-neoplastic agents, which will be determined on a patient to patient basis. Routes of administration include, for example, oral, intravenous, intraperitoneal, subcutaneous, or intramuscular administration. The dose of antagonist administered depends on numerous factors, including, for example, the type of antagonists, the type and severity of the tumor being treated and the route of administration of the antagonists. It should be emphasized, however, that the present invention is not limited to any particular method or route of administration.

Suitable carriers include, for example, one or more of water, saline, phosphate buffered saline, dextrose, glycerol, ethanol and the like, as well as combinations thereof. Carriers can further comprise minor amounts of auxiliary substances, such as wetting or emulsifying agents, preservatives or buffers, which enhance the shelf life or effectiveness of the theramutein modulator as the active ingredient. The compositions can, as is well known in the art, be formulated so as to provide quick, sustained or delayed release of the active ingredient after administration to the mammal.

The compositions of this invention can be in a variety of forms. These include, for example, solid, semi-solid and liquid dosage forms, such as tablets, pills, powders, liquid solutions, dispersions or suspensions, liposomes, suppositories, injectable and infusible solutions. The preferred form depends on the intended mode of administration and therapeutic application.

Such compositions of the present invention are prepared in a manner well known in the pharmaceutical art. In making the composition the active ingredient will usually be mixed with a carrier, or diluted by a carrier and/or enclosed within a carrier which can, for example, be in the form of a capsule, sachet, paper or other container. When the carrier serves as a diluent, it can be a solid, semi-solid, or liquid material, which acts as a vehicle, excipient or medium for the active ingredient. Thus, the composition can be in the form of tablets, lozenges, sachets, cachets, elixirs, suspensions, aerosols (as a solid or in a liquid medium), ointments containing, for example, up to 10% by weight of the active compound, soft and hard gelatin capsules, suppositories, injection solutions, suspensions, sterile packaged powders and as a topical patch.

It should be appreciated that the methods and compositions of the present invention can be administered to any suitable mammal, such as a rabbit, rat, or mouse. More preferably, the mammal is a human.

The compounds according to the invention may also be present as salts. In the context of the invention, preference is given to pharmaceutically acceptable salts. Pharmaceutically acceptable salts refers to an acid addition salt or a basic addition salt of a compound of the invention in which the resulting counter ion is understood in the art to be generally acceptable for pharmaceutical uses. Pharmaceutically acceptable salts can be salts of the compounds according to the invention with inorganic or organic acids. Preference is given to salts with inorganic acids, such as, for example, hydrochloric acid, hydrobromic acid, phosphoric acid or sulfuric acid, or to salts with organic carboxylic or sulfonic acids, such as, for example, acetic acid, maleic acid, fumaric acid, malic acid, citric acid, tartaric acid, lactic acid, benzoic acid, or methanesulfonic acid, ethanesulfonic acid, phenylsulfonic acid, toluenesulfonic acid or naphthalenedisulfonic acid. Pharmaceutically acceptable salts can also be metal or ammonium salts of the compounds according to the invention. Particular preference is given to, for example, sodium, potassium, magnesium or calcium salts, and also to ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine. (see, Berge et al. *J. Pharm. Sci.* 1977, 66, 1-19).

1. Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains.
2. It is to be understood and expected that variations in the principles of invention herein disclosed may be made by one skilled in the art and it is intended that such modifications are to be included within the scope of the present invention.
3. The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J et al., (1989) Molecular Cloning: A Laboratory Manual, $2^{nd}$ ed., Cold Spring Harbor Laboratory Press; Coligan, J. et al. (1994) Current Protocols in Immunology, Wiley & Sons, Incorporated; Enna, S. J. et al. (1991) Current Protocols in Pharmacology, Wiley & Sons, Bonifacino, J. S. et al. (1999) Current Protocols in Cell Biology, Wiley & Sons, and U.S. Pat. No. 4,980,281. All references mentioned herein are incorporated in their entirety.

EXAMPLES $p210^{Bcr-Abl-T315I}$ is a theramutein of the p210Bcr-Abl protein ($p210^{Bcr-Abl}$) that is resistant to inhibition by imatinib mesylate (Gleevec, STI-571). The mutation at position 315 converts a threonine to an isoleucine residue and is one of several mutations that are observed among resistant or relapsed patients. This particular mutant, however, is the most resistant such theramutein yet identified.

A phenoresponse was determined for a Ba/F3 cell line engineered to overexpress the $p210^{Bcr-Abl-T315I}$ theramutein. The phenoresponse was determined relative to non-transformed Ba/F3 cells and Ba/F3 cells that express the $p210^{Bcr-Abl-wt}$ prototheramutein. The phenoresponse was the ability of the T315I mutants to grow to a higher cell saturation density under analogous culture conditions as compared to the control non-transformed Ba/F3 cell line, and to grow in the absence of interleukin 3 (IL-3), which is required for maintenance of the control non-transformed Ba/F3 cell line. The phenoresponse was defined and characterized according to the teachings given above.

The detection system utilized was a high speed cell imaging and counting system in which 3 µl sample volumes of cells were sequentially injected through a 5 µl optical microcell, digitally imaged and electronically stored, scanned, and then counted, all under a microcomputer-based control system. The system has the capacity to perform direct cell counts on samples from cultures as small as 500 µl and provides statistically significant total cell counts from culture samples containing as few as 12,500 cells. All of the figures displaying cell count and viability assays utilized this system for data acquisition and analysis. Simultaneously with the cell count performed, the system is also capable of determining overall cell viability by distinguishing counted, imaged cells that have excluded trypan blue (counted as "viable" cells) from cells which have taken up the trypan blue dye (counted as "non-viable" cells). Injection of trypan blue into the cell sample occurs immediately prior to the sample being sequentially injected into the microcell for simultaneous cell counting and imaging.

The system may be integrated into the workflow of high-throughput screening devices to provide a sensitive and precise cell counting and cell viability assay system that is more reliable and less prone to confounding effects of metabolic viability-based cellular assays such as XTT or Alamar blue.

Initially, approximately 113,000 compounds were screened at concentrations generally ranging from 10 to 20 µM to identify a subset that was capable of affecting growth of Ba/F3 cells (Ba/F3 T315I cells) overexpressing the $p210^{Bcr-Abl-T315I}$ theramutein by any means.

A total of approximately 11,760 compounds showed greater than 50% growth inhibition, which were thought to correspond to approximately 4500 distinct chemical classes. Retesting of these compounds with the same cell line yielded a database of compound responsiveness which was then sorted and rank ordered according to those compounds exhibiting the highest overall growth inhibition. From this rank ordered database, the highest scoring 130 compounds (based upon the greatest degree of growth inhibition observed at the lowest concentrations that compounds were tested) were then rescreened in a defined cell-based assay system using Ba/F3 T315I as test cells and wild type Ba/F3 as control cells according to the methods of the present invention. Compounds of interest were those that differentially inhibited growth of Ba/F3 cells expressing the $p210^{Bcr-Abl-T315I}$ theramutein relative to non-transformed wild type Ba/F3 cells. Six compounds were identified that fulfilled the desired criteria, and some of these compounds were analyzed in further detail using the Ba/F3 $p210^{Bcr-Abl-wt}$ cells line (Ba/F3 P210 cells) as well. One compound was unavailable for further testing due to lack of availability of additional material from the chemical supplier. The remaining five compounds were independently evaluated in additional cell-based assays using the aforementioned cell lines as well as in a cell-free purified protein kinase assay using human recombinantly produced 120 Kd kinase domain fragments isolated from both wild type P210 Bcr-Abl as well as P210 T315I mutant kinase domain.

Figure 4:
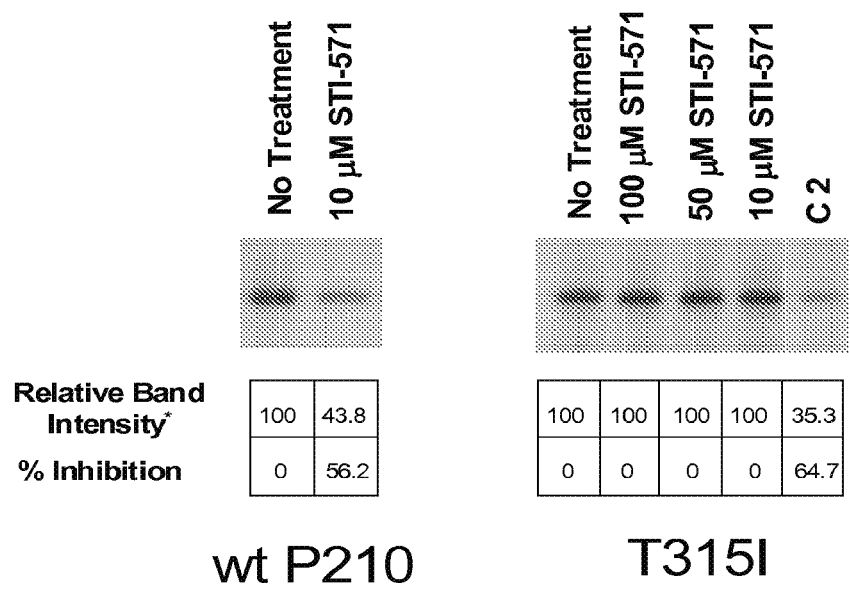
FIG. 4 shows an autoradiograph of recombinant P210 Bcr-Abl wild type and T315I mutant kinase domains assayed for autophosphorylation activity. 200 ng of protein were preincubated with test substances for 10 minutes under standard autophosphoryation reaction conditions and then radiolabelled ATP was added and the reactions proceeded for 30 minutes at 30° C., after which the samples were separated by SDS-PAGE. The gels were silver-stained, dried down under vacuum and exposed to X-ray film. Note that whereas 10 μM STI 571 is effective against wild type P210 Bcr-Abl, it is virtually ineffective against the T315I kinase domain, even at concentrations up to 100 μM. C2 and C6 are the best two compounds identified, followed by C5, C7 and C4. All of the compounds tested positively to some extent. "P210 cell line" refers to cells expressing $p210^{BCR-ABL-wt}$. "T315I cell line" refers to cells expressing $p210^{BCR-ABL-T315I}$.
Figure 5:
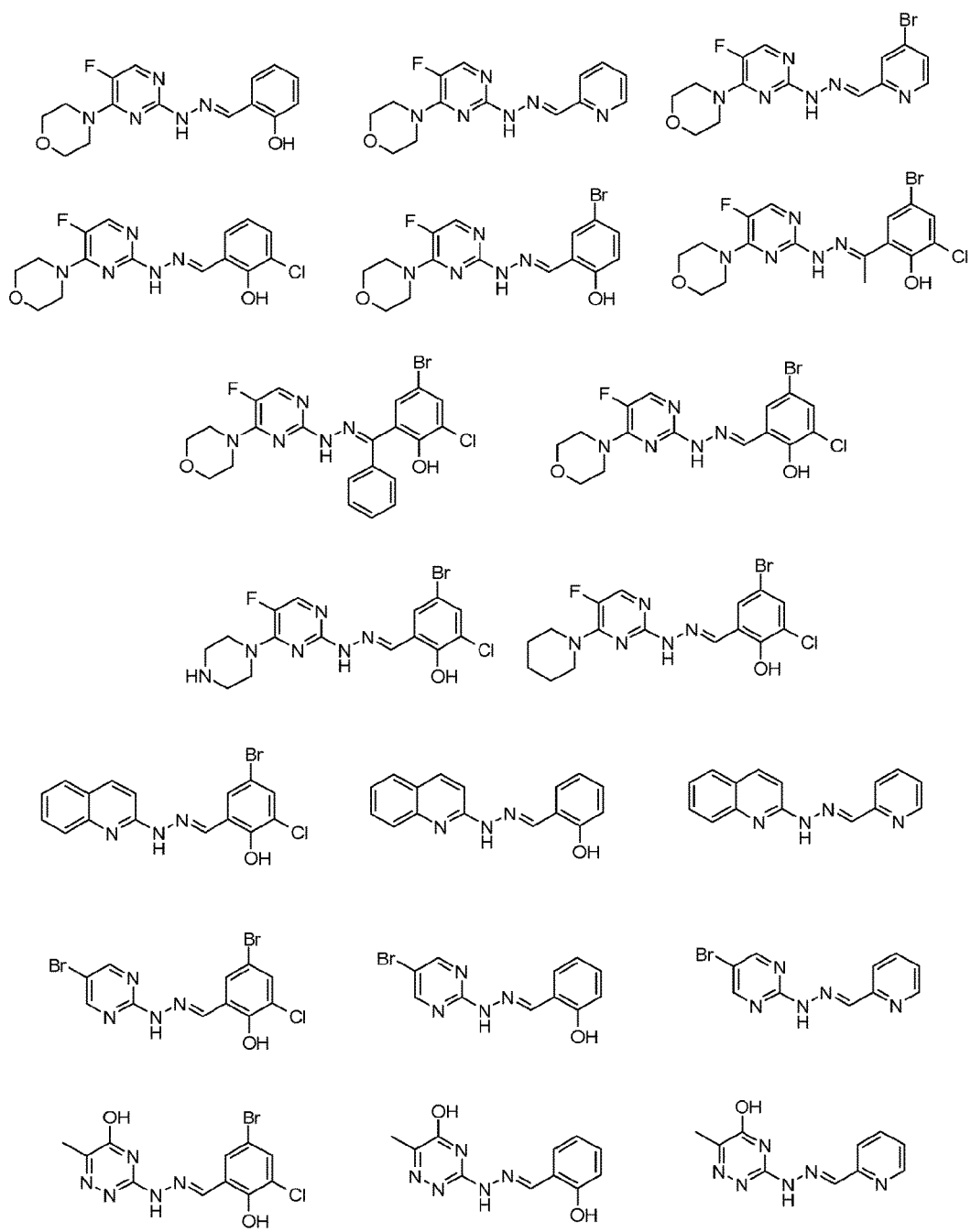
FIG. 5 shows the chemical structures of representative compounds of the present invention.
Figure 6:
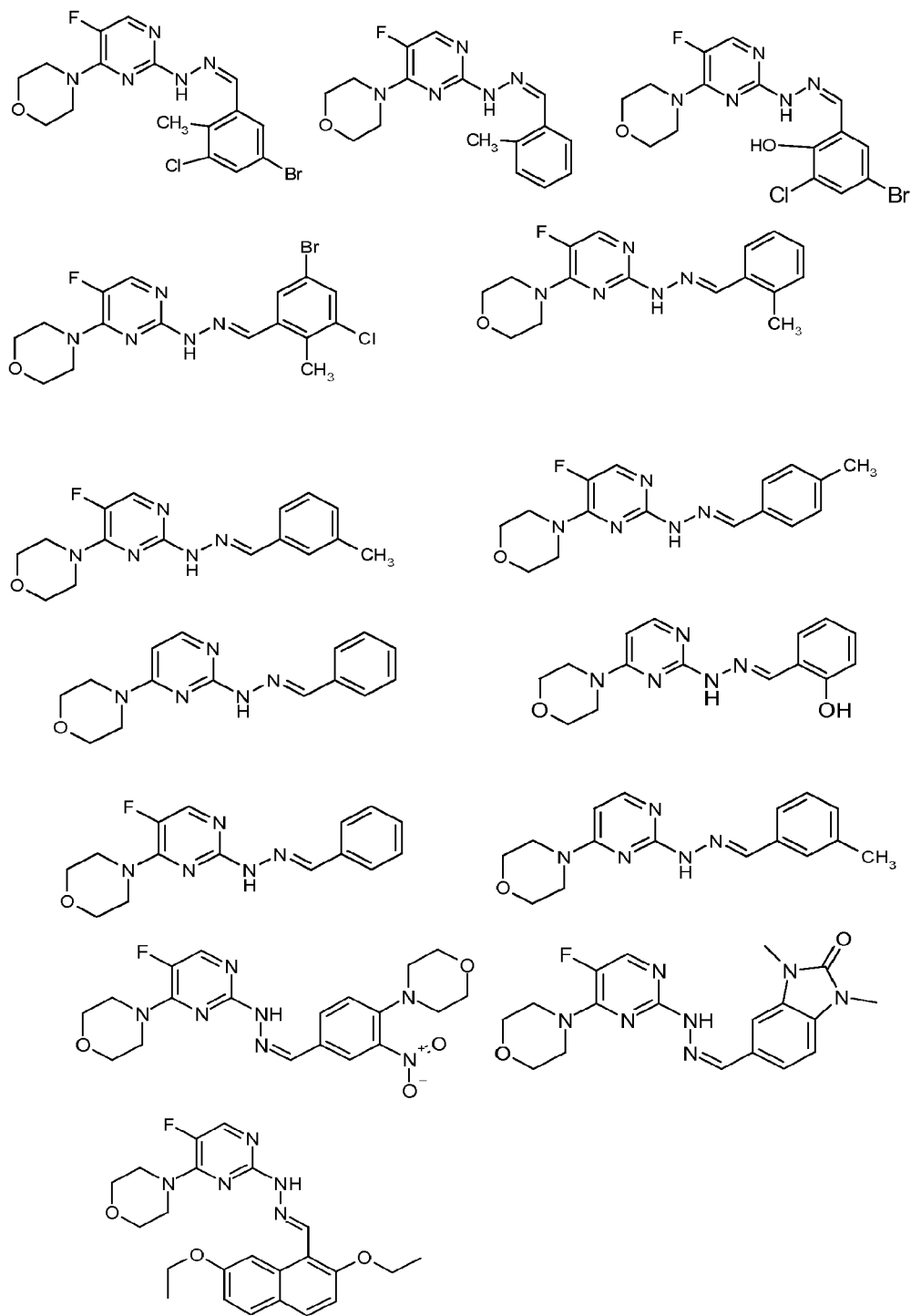
FIG. 6 shows the chemical structures of representative compounds of the present invention.
Figure 7:
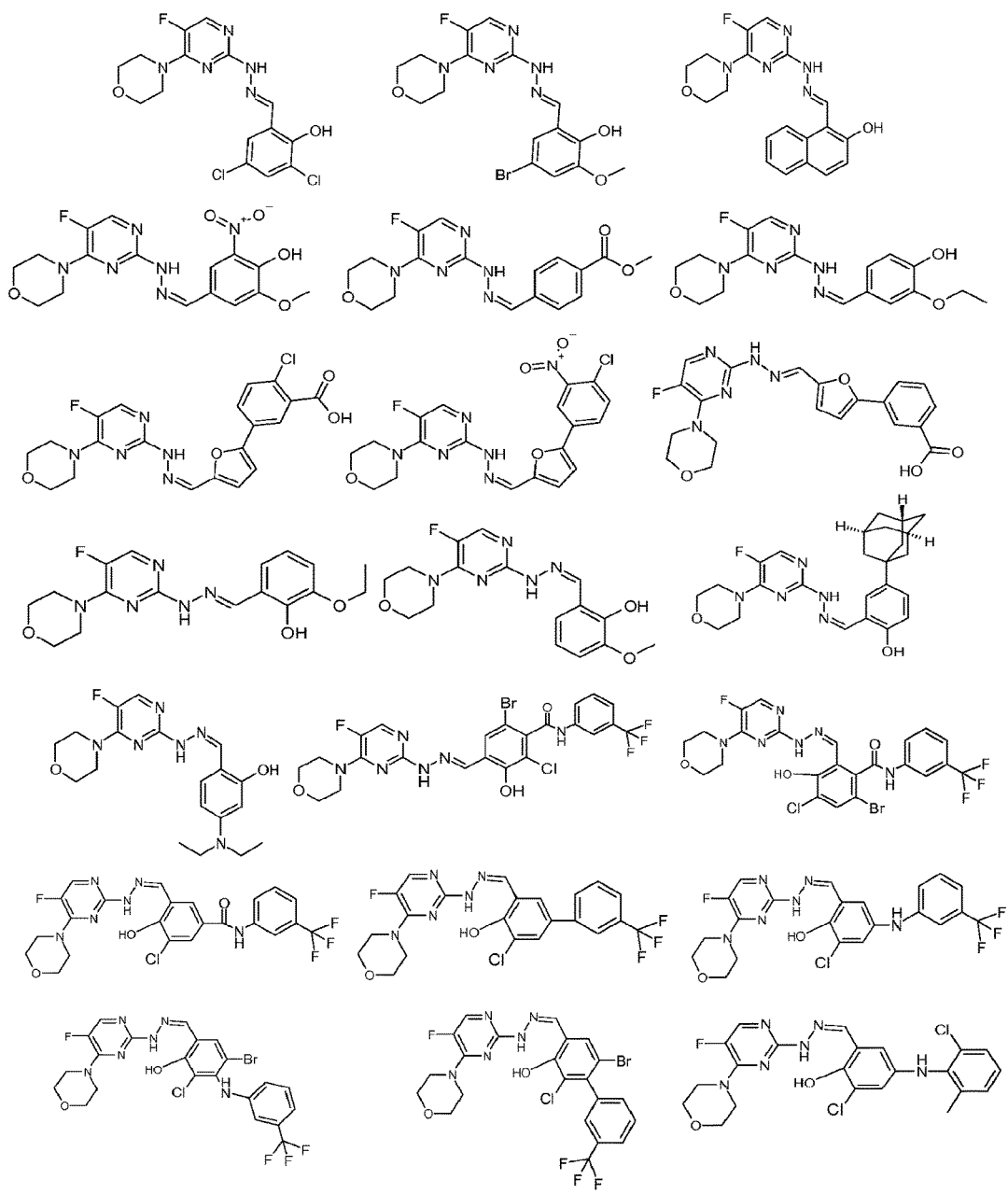
FIG. 7 shows the chemical structures of representative compounds of the present invention.
Figure 8:
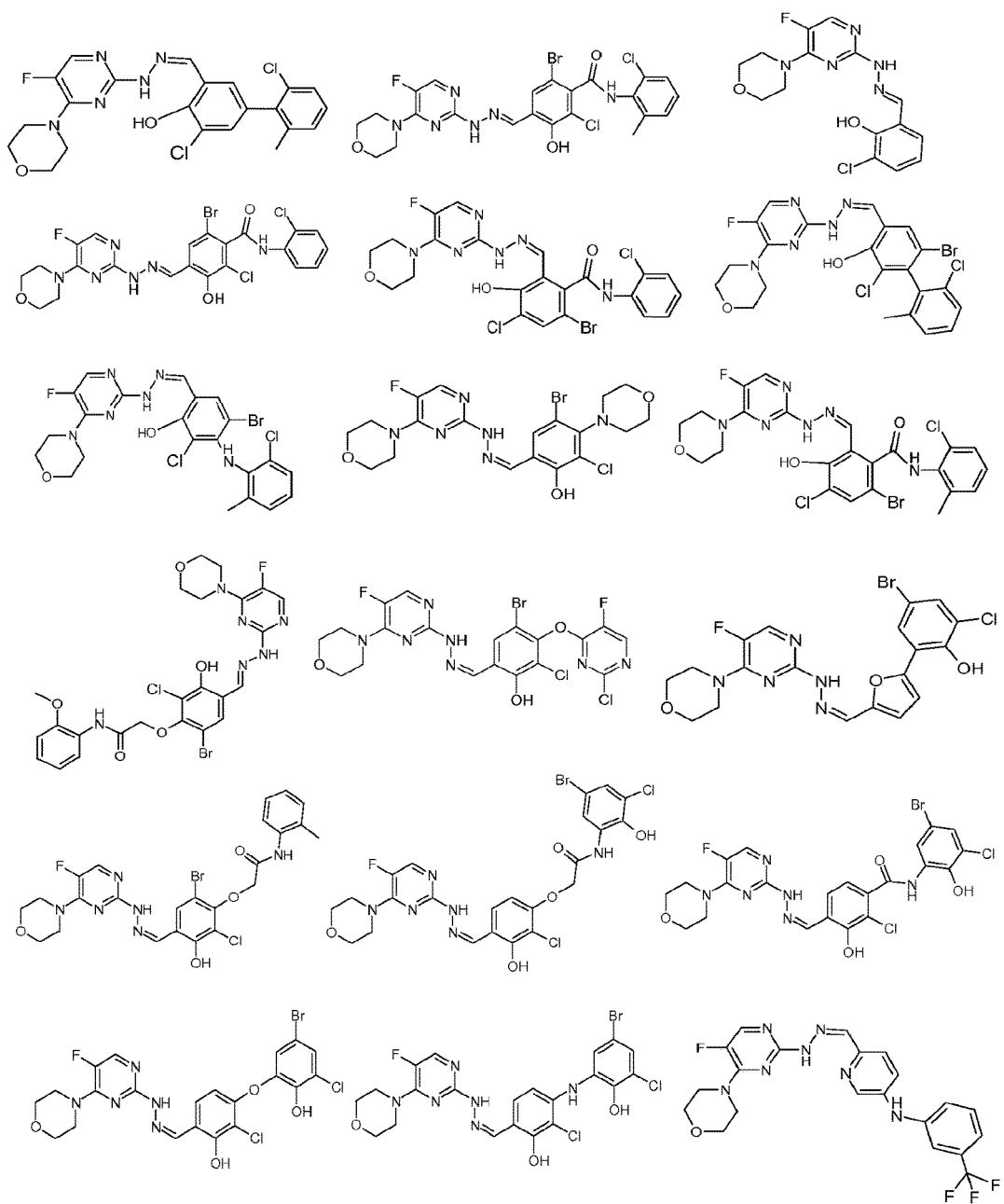
FIG. 8 shows the chemical structures of representative compounds of the present invention.
Figure 9:
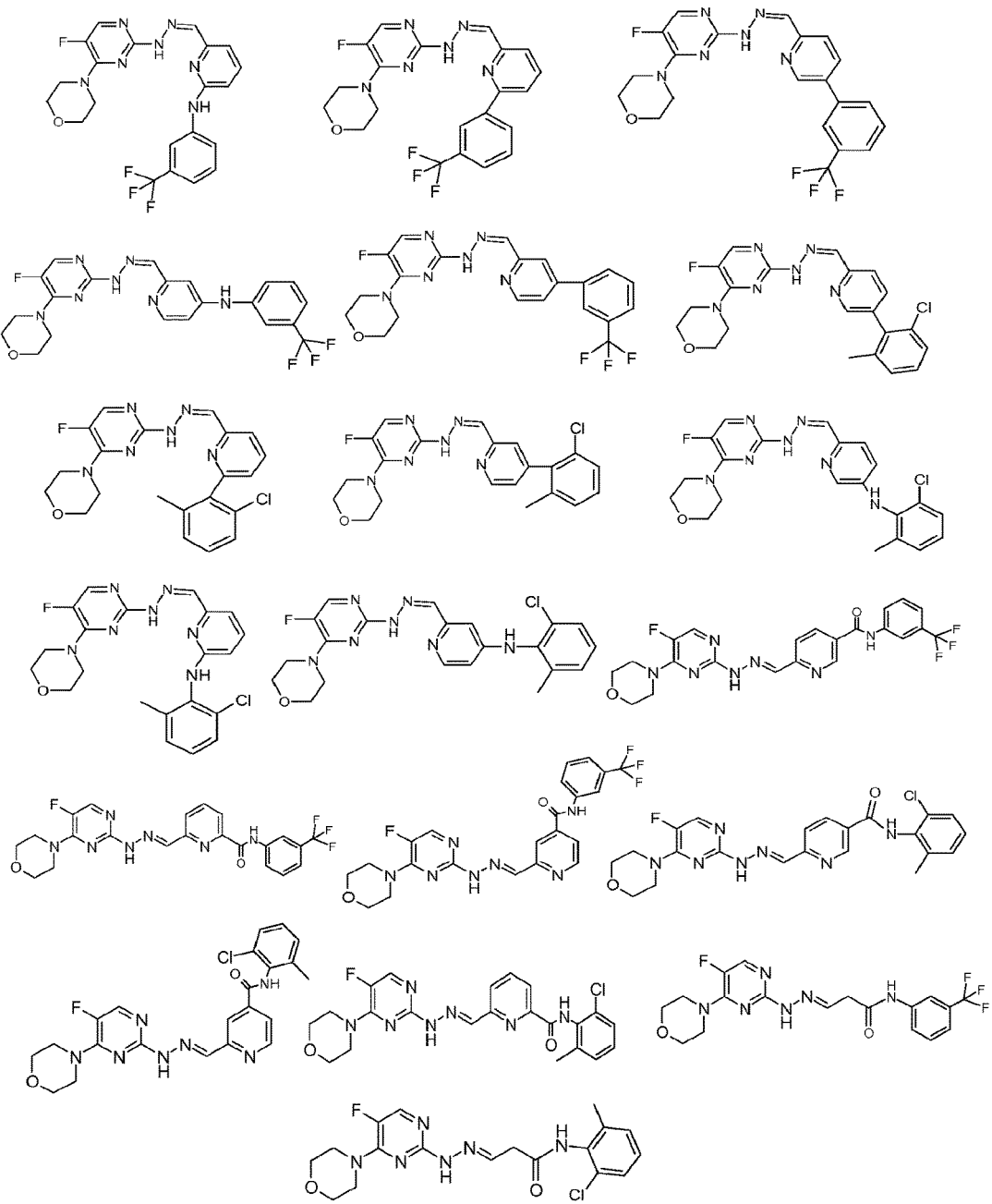
FIG. 9 shows the chemical structures of representative compounds of the present invention.
Figure 10:
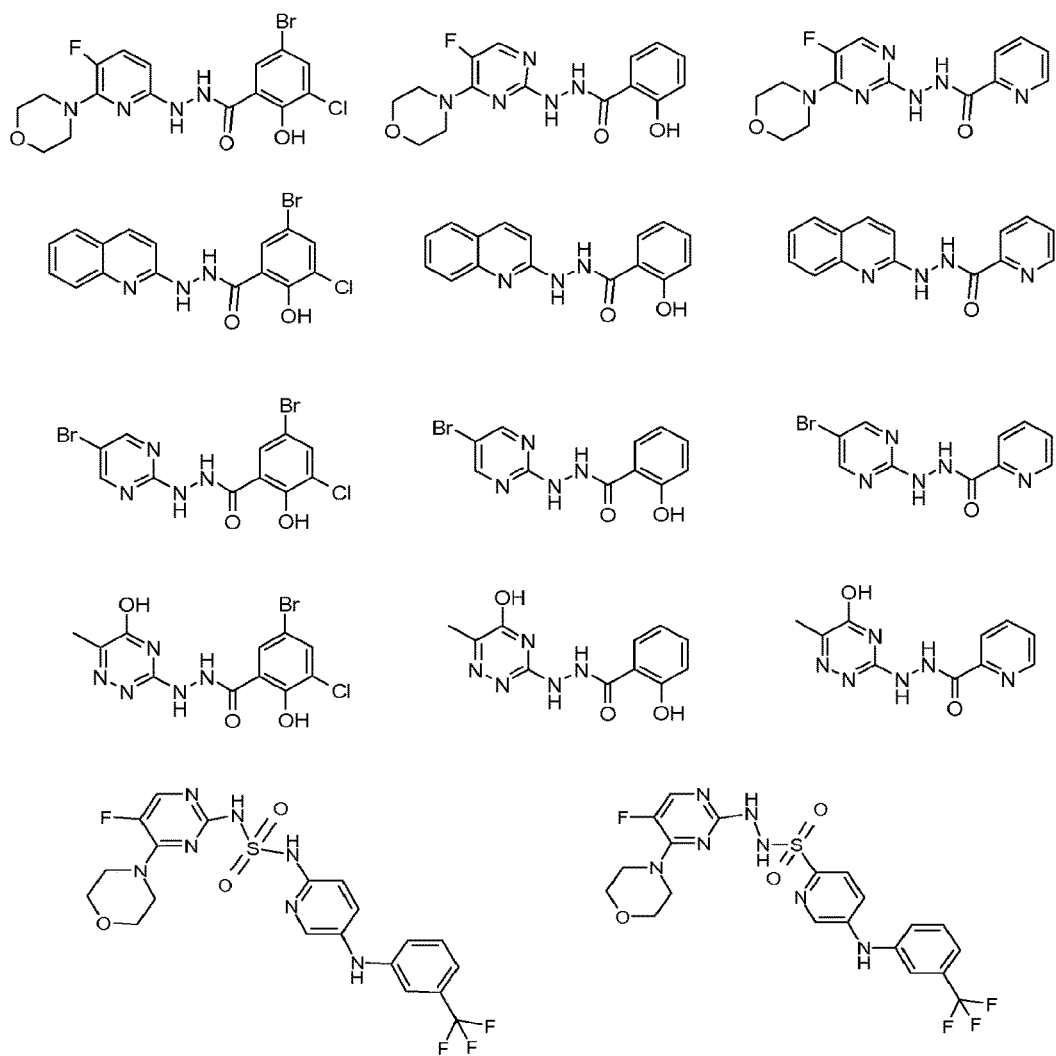
FIG. 10 shows the chemical structures of representative compounds of the present invention.
Figure 11:
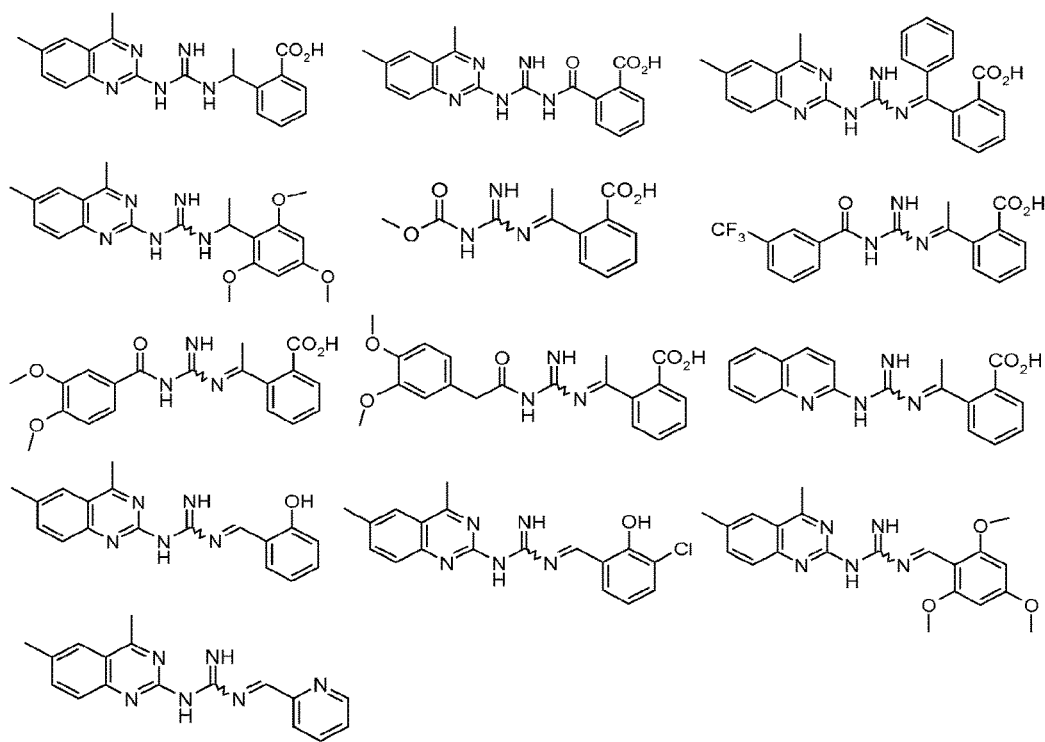
FIG. 11 shows the chemical structures of representative compounds of the present invention.
Figure 12:
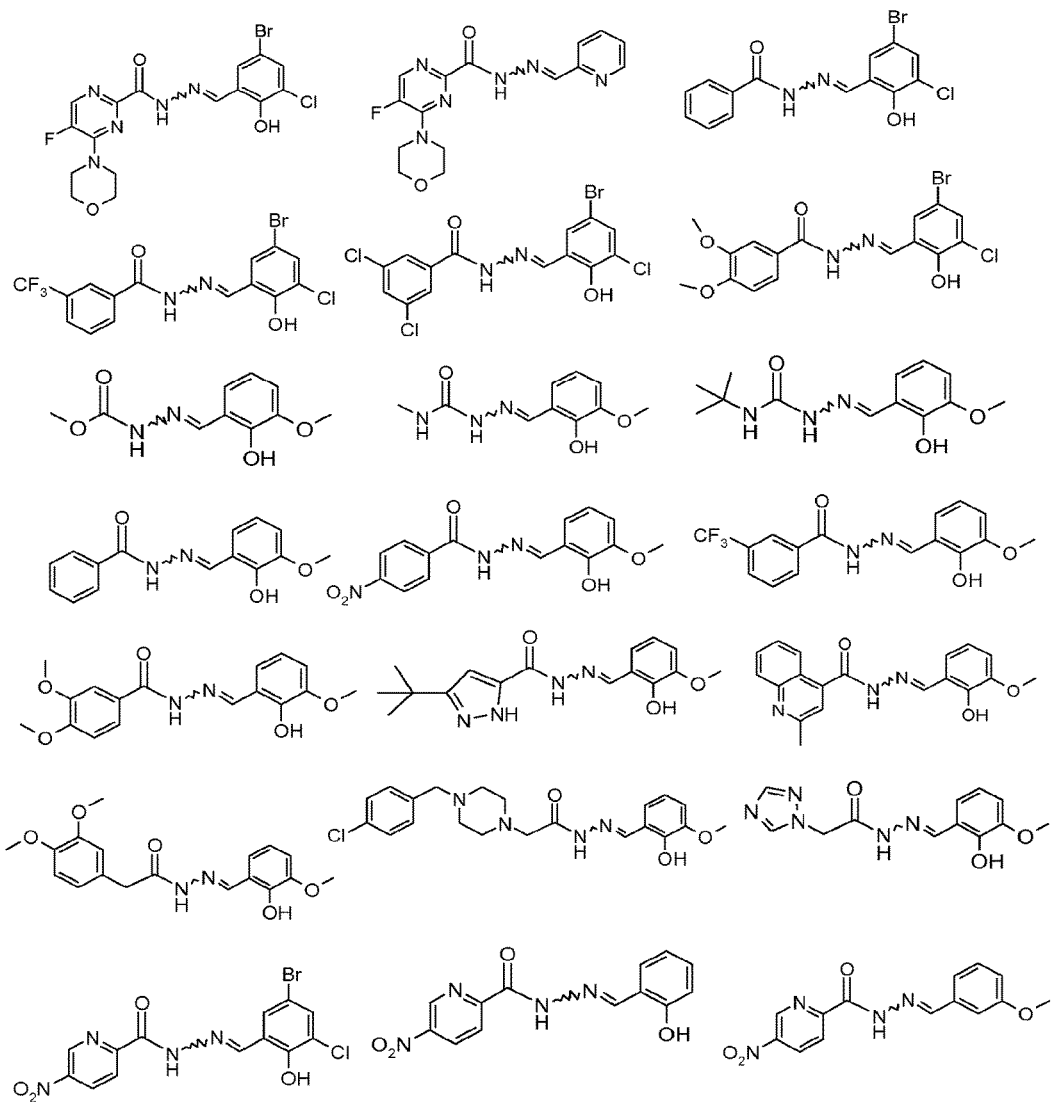
FIG. 12 shows the chemical structures of representative compounds of the present invention.
Figure 13:
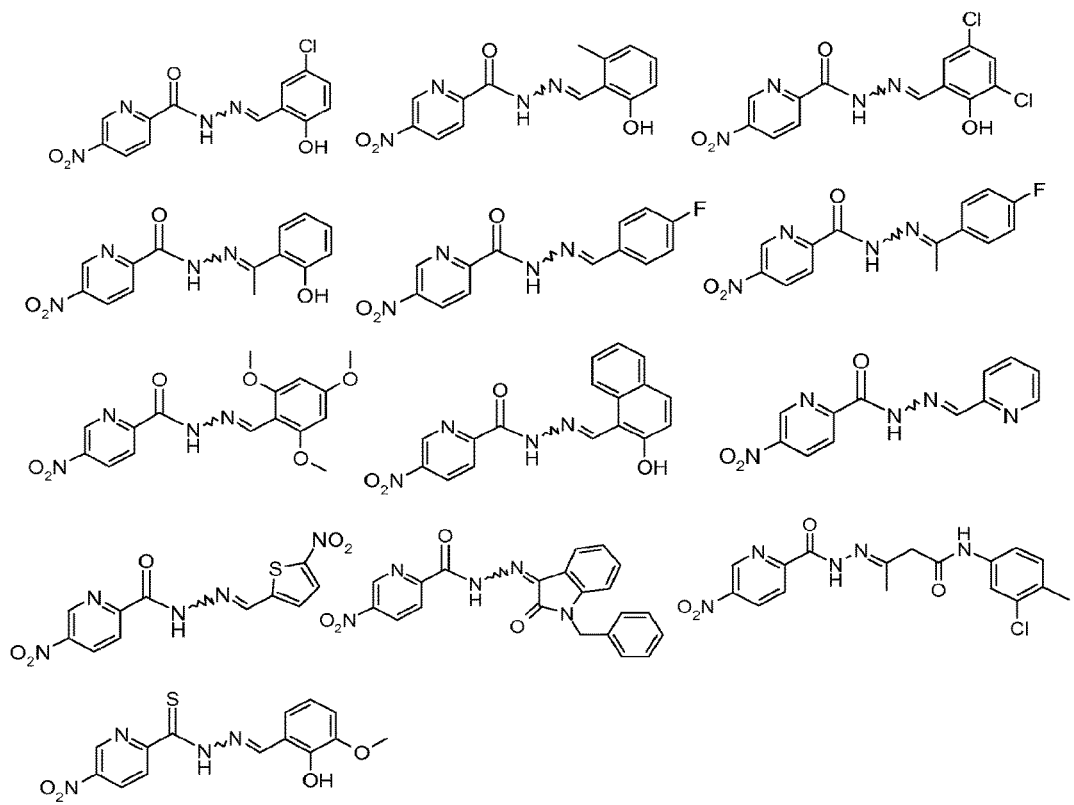
FIG. 13 shows the chemical structures of representative compounds of the present invention.

All five compounds inhibited $p210^{Bcr-Abl-T315I}$ 120 Kd activity as measured by inhibition of autophosphorylation activity, as shown in FIG. 4. Thus, of the 6 highest scoring compounds out of more than 113,000 compounds screened, at least 5 of the six directly inhibited the $p210^{Bcr-Abl-T315I}$ mutant. It is noteworthy that Compound 5 appears to spread the recombinant protein band out on the SDS page gel. This was also evident on the silver-stained gel (data not shown). It is possible that this compound may actually be a "suicide" inhibitor that is able to covalently cross-link the POI in order to permanently inhibit its activity, but this will require further study.

Taken together, the teachings and the results described herein provide conclusive proof that the system is capable of identifying inhibitors or activators of the selected theramutein, and the skilled investigator will immediately recognize that such a system may be easily applied to any other theramutein with only obvious, minor modifications.

Figure 2:
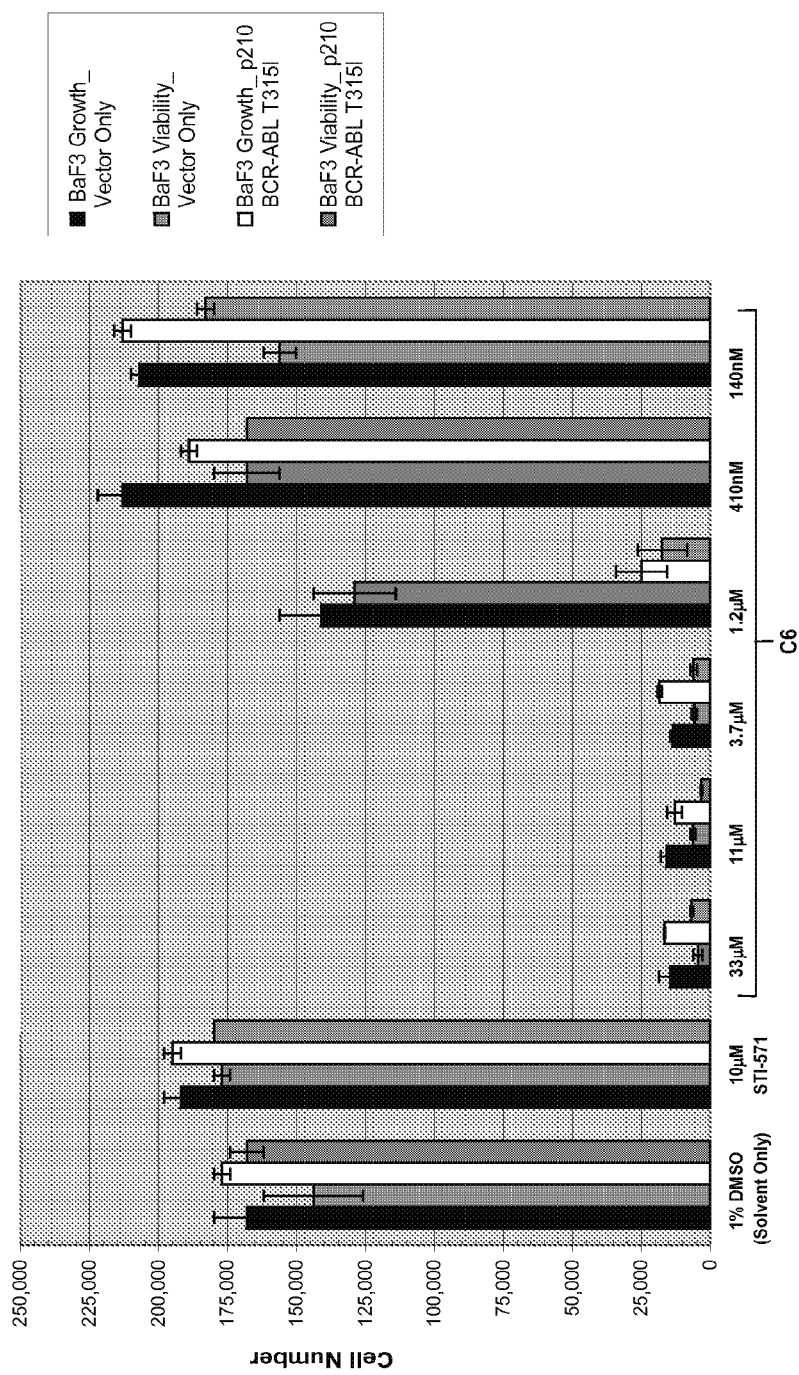
FIG. 2 shows the effect on growth and viability of different concentrations of Compound 6 (C6) for non-transformed vector control Ba/F3 cells as well as Ba/F3 cells expressing the $p210^{Bcr-Abl-T315I}$ drug resistant mutant. All other details are as per FIG. 1.

Representative examples of the cell-based assay results demonstrating selective inhibition of growth of the Ba/F3 T315I cell line relative to the wild type non-transformed Ba/F3 cells are shown in FIGS. 1 and 2. The compounds inhibited growth and reduced the viability of cells expressing the T315I theramutein at concentrations under which the growth and viability of the wild type Ba/F3 non-transformed cells (not expressing either $p210^{Bcr-Abl-wt}$ or $p210^{Bcr-Abl-T315I}$) were relatively unaffected, whereas cells expressing both the prototheramutein as well as the theramutein were substantially inhibited. In some instances, the T315I expressing cells were inhibited to an even greater extent than the P210 prototheramutein expressing cells. (See, for example, FIG. 3, right hand side, Compound 3 results against P210 and T315I cells.

In summary, the methods presented herein provide a fundamental advance in the form of a generalizable approach for creating or identifying modulators of any given theramutein. The results demonstrate conclusively the power of the method to identify critically needed compounds to overcome a specific type of acquired drug resistance that is uniformly fatal in certain patient populations and is presently untreatable. Furthermore, it is evident to one of skill in this art that the techniques and methods described herein may, using obvious modifications, be straighforwardly generalized to any potential theramutein of clinical significance.

It is remarkable that out of a primary screen of more than 100,000 compounds where approximately 10,000 compounds exhibited some degree of growth inhibition, when the most potent growth inhibitory substances were rescreened using the Method described in detail herein, 6 distinct compounds were identified and all of the compounds that were subsequently tested exhibited inhibitory activity in a cell-free purified protein kinase assay using the T315I mutant (one compound was unavailable for further testing). Based upon such remarkable results, it becomes immediately clear to the skilled artisan that the method may be effectively applied toward the identification of inhibitors or activators of any theramutein based upon the proper selection and definition of the phenoresponse according to the teachings in the sections given above and the documents incorporated by reference herein. For example, with knowledge of the foregoing, one of ordinary skill in the art could easily design an assay system to identify inhibitors of theramuteins derived from other prototheramuteins known to exhibit mutations that confer drug resistance such as the c-kit gene product or the Epidermal Growth Factor (EGF) Receptor (EGFR), or the Platelet Derived Growth Factor (PDGF) Receptor $\alpha$ and $\beta$. No limitation should be inferred upon the utility of the method with respect to its ability to be utilized with any given theramutein expressed in any mammalian cell type for which a corresponding phenoresponse is detectable.

All references to any publication, patent, or other citation are hereby incorporated by reference.

REFERENCES

Adcock, I. M., Lane, S. J. Mechanisms of Steroid Action and Resistance in Inflammation. Journal of Endocrinology, Volume 178 (September 2003) Pages 347-355

Allen, P. B., Wiedemann, L. M. An Activating Mutation in the ATP Binding Site of the ABL Kinase Domain. The Journal of Biological Chemistry, Volume 271 (Aug. 9, 1996) Pages 19585-19591

Barthe, C., Cony-Makhoul, P., Melo, J. V., Reiffers, J., Mahon, F, X. Roots of Clinical Resistance to STI-571 Cancer Therapy. Science, Volume 293 (Sep. 21, 2001) Page 2163a Berge, S. M., Bighley, L. D., Monkhouse, D. C. Pharmaceutical salts. Journal of Pharmaceutical Science, Volume 66 (January 1977) Pages 1-19.

Bolstad, B. M., Irizarry, R. A., Astrand, M., Speed, T. P. A Comparison of Normalization Methods for High Density Oligonucleotide Array Data Based on Variance and Bias. Bioinformatics, Volume 19 (Jan. 22, 2003) Pages 185-193.

Bonifacino, J. S. Current Protocols in Cell Biology, Wiley & Sons, New York, 1999

Branford, S., Rudzki, Z., Walsh, S., Grigg, A., Arthur, C., Taylor, K., Hermann, R., Lynch, K. P., Hughes, T. P. High Frequency of Point Mutations Clustered Within the Adenosine Triphosphate-Binding Region of BCR/ABL in Patients with Chronic Myeloid Leukemia or Ph-positive Acute Lymphoblastic Leukemia Who Develop Imatinib (STI571) Resistance. Blood, Volume 99 (May 1, 2002) Pages 3472-3475

Breshears, S. R., Wang, S. S., Bechtolt, S. G., Christensen, B. E. Purines. VIII: The Aminolysis of Certain Chlorosubstituted Purines. Journal of the American Chemical Society, Volume 81 (Jul. 20, 1959) Pages 3789-3792

Capps, T. M., Heard, N. E., Simmons, D. P., Connor, C. L. Identification and Synthesis of a Unique Disulfide Dimeric Metabolite of Primisulfuron-methyl in the Mouse. Journal of Agricultural and Food Chemistry, Volume 41 (1993) Pages 2411-2415

Coligan, J. Current Protocols in Immunology, Wiley & Sons, New York, 1994

Corbin, A. S., Buchdunger, E., Pascal, F., Druker, B. J. Analysis of the Structural Basis of Specificity of Inhibition of the Abl Kinase by STI571. The Journal of Biological Chemistry, Volume 277 (Aug. 30, 2002) Pages 32214-32219

Cunningham, B. C., De Vos, A. M., Mulkerrin, M. G., Ultsch, M, Wells, J. A. Selecting Ligand Agonists and Antagonists. U.S. Pat. No. 5,506,107 (Apr. 9, 1996)

Cunningham, B. C., Wells, J. A., Clark, R. G., Olson, K., Fuh, G. G. Method for Inhibiting Growth Hormone Action. U.S. Pat. No. 6,004,931 (Dec. 21, 1999)

Daley, G. Q., Van Etten, R. A., Baltimore, D. Induction of Chronic Myelogenous Leukemia in Mice by the $P210^{bcr/abl}$ Gene of the Philadelphia Chromosome. Science, Volume 247 (Feb. 16, 1990) Pages 824-830

Davis, T. L. The Mechanism of Reactions in the Urea Series. Proceedings of the National Academy of Sciences of the United States of America, Volume 11 (1925) Pages 68-73

Druker, B. J., M. D., Sawyers, C. L., M. D., Kantarjian, H., M. D., Resta, D. J., R. N., Reese, S. F., M. D., Ford, J. M., M. D., Capdeville, R., M. D., Talpaz, M., M. D. Activity of a Specific Inhibitor of the BCR-ABL Tyrosine Kinase in the Blast Crisis of Chronic Myeloid Leukemia and Acute Lymphoblastic Leukemia with the Philadelphia Chromosome. The New England Journal of Medicine, Volume 344 (Apr. 5, 2001) Pages 1038-1042

Druker, B. J., M. D., Talpaz, M., M. D., Resta, D. J., R. N., Peng, B., Ph.D., Buchdunger, E., Ph.D., Ford, J. M., M. D., Lydon, N. B., Ph.D., Kantarjian, H., M. D., Capdeville, R., M. D., Ohno-Jones, S., B. S., Sawyers, C. L., M. D. Efficacy and Safety of a Specific Inhibitor of the BCR-ABL Tyrosine Kinase in Chronic Myeloid Leukemia. The New England Journal of Medicine, Volume 344 (Apr. 5, 2001) Pages 1031-1037

Druker, B. J., Tamura, S., Buchdunger, E., Ohno, S., Segal, G. M., Fanning, S., Zimmermann, J., Lydon, N. B. Effects of a Selective Inhibitor of the Abl Tyrosine Kinase on the Growth of Bcr-Abl Positive Cells. Nature Medicine, Volume 2 (May 1996) Pages 561-566

Enna, S. J. Current Protocols in Pharmacology, Wiley & Sons, New York, 1991

Faderl, S., M. D., Talpaz, M., M. D., Estrov, Z., M. D., O'Brien, S., M. D., Kurzrock, R., M. D., Kantarjian, H. M., M. D. The Biology of Chronic Myeloid Leukemia. The New England Journal of Medicine, Volume 341 (Jul. 15, 1999) Pages 164-172

Foreman, J. C. and Johansen, T. Textbook of Receptor Pharmacology. CRC Press, Boca Raton, 2002

Gambacorti-Passerini, C., Barni, R., Le Coutre, P., Zucchetti, M., Cabrita, G., Cleris, L., Rossi, F., Gianazza, E., Brueggen, J., Cozens, R., Pioltelli, P., Pogliani, E., Corneo, G., Formelli, F., D'Incalci, M. Role of al Acid Glycoprotein in the In Vivo Resistance of Human BCR-ABL$^+$ Leukemic Cells to the Abl Inhibitor STI571. Journal of the National Cancer Institute, Volume 92 (Oct. 18, 2000) Pages 1641-1650

Gineinah, M. M., El-Sherbeny, M. A., Nasr, M. N., Maarouf, A. R. Synthesis and Antiinflammatory Screening of Some Quinazoline and Quinazolyl-4-oxoquinazoline Derivatives. Archiv der Pharmazie—Pharmaceutical and Medicinal Chemistry, Volume 335 (2002) Pages 556-562

Gorre, M. E., Mohammed, M., Ellwood, K., Hsu, N., Paquette, R., Rao, P. N., Sawyers, C. L. Clinical Resistance to STI-571 Cancer Therapy Caused by BCR-ABL Gene Mutation or Amplification. Science, Volume 293 (Aug. 3, 2001) Pages 876-880

Greene, T. W.; Wuts, P. G. M. Protective Groups in Organic Synthesis, $2^{nd}$ ed., Wiley, New York, 1991

Hofmann, W. K., Jones, L. C., Lemp, N. A., DeVos, S., Gschaidmeier, H., Hoelzer, D., Ottmann, O. G., Koeffler, H. P. Ph$^+$ Acute Lymphoblastic Leukemia Resistant to the Tyrosine Kinase Inhibitor STI571 has a Unique BCR-ABL Gene Mutation. Blood, Volume 99 (Mar. 1, 2002) Pages 1860-1862

Horowitz, A. D., Greenebaum, E., Weinstein, I. B. Identification of Receptors for Phorbol Ester Tumor Promoters in Intact Mammalian Cells and of an Inhibitor of Receptor Binding in Biologic Fluids. Proceedings of the National Academy of Sciences of the United States of America, Volume 78 (April 1981) Pages 2315-2319

Hou, Y. Y., Tan, Y. S., Sun, M. H., Wei, Y. K., Xu, J. F., Lu, S. H., A-Ke-Su, S. J., Zhou, Y. N., Gao, F., Zheng, A. H., Zhang, T. M., Hou, W. Z., Wang, J., Du, X., Zhu, X. Z. C-kit Gene Mutation in Human Gastrointestinal Stromal Tumors. World Journal of Gastroenterology, Volume 10 (May 1, 2004) Pages 1310-1314

Housey, G. M. Method of Screening for Protein Inhibitors and Activators. U.S. Pat. No. 4,980,281 (Dec. 25, 1990)

Housey, G. M. The Role of Protein Kinase C in Growth Control and Tumor Promotion. Ph.D. Dissertation, (1988)

Housey, G. M., Johnson, M. D., Hsiao, W. L., O'Brian, C. A., Murphy, J. P., Kirschmeier, P., Weinstein, I. B. Overproduction of Protein Kinase C Causes Disordered Growth Control in Rat Fibroblasts. Cell, Volume 52 (Feb. 12, 1988) Pages 343-354

Huron, D. R., Gorre, M. E., Kraker, A. J., Sawyers, C. L., Rosen, N., Moasser, M. M. A Novel Pyridopyrimidine Inhibitor of Abl Kinase is a Picomolar Inhibitor of Bcr-Abl-driven K562 Cells and is Effective Against STI571-resistant Bcr-Abl Mutants. Clinical Cancer Research, Volume 9 (April 2003) Pages 1267-1273

La Rosee, P., Corbin, A. S., Stoffregen, E. P., Deininger, M. W., Druker, B. J. Activity of the Bcr-Abl Kinase Inhibitor PD180970 Against Clinically Relevant Bcr-Abl Isoforms That Cause Resistance to Imatinib Mesylate (Gleevec, STI-571). Cancer Research, Volume 62 (Dec. 15, 2002) Pages 7149-7153

Latham, H. G. Jr., May, E. L., Mosettig, E. Amino- and Guanidino-Phenylglucosides. Journal of Organic Chemistry, Volume 15 (1950) Pages 884-889

Le Coutre, P., Tassi, E., Varella-Garcia, M., Barni, R., Mologni, L., Cabrita, G., Marchesi, E., Supino, R., Gambacorti-Passerini, C. Induction of Resistance to the Abelson Inhibitor STI571 in Human Leukemic Cells Through Gene Amplification. Blood, Volume 95 (Mar. 1, 2000) Pages 1758-1766

Leonard, G. D., Fojo, T., Bates, S. E. The Role of ABC Transporters in Clinical Practice. The Oncologist, Volume 8 (2003) Pages 411-424

Loutfy, M. R., Walmsley, S. L. Salvage Antiretroviral Therapy in HIV Infection. Expert Opinion, Volume 3 (February 2002) Pages 81-90

Lynch, T. J., M. D., Bell, D. W., Ph.D., Sordella, R., Ph.D., Gurubhagavatula, S., M. D., Okimoto, R. A., B. S., Brannigan, B. W., B. A., Harris, P. L., M. S., Haserlat, S. M., B. A., Supko, J. G., Ph.D., Haluska, F. G., M. D., Ph.D., Louis, D. N., M. D., Christiani, D. C., M. D., Settleman, J., Ph.D., Haber, D. A., M. D., Ph.D. Activating Mutations in the Epidermal Growth Factor Receptor Underlying Responsiveness of Non-Small-Cell Lung Cancer to Gefitinib. The New England Journal of Medicine, Volume 350 (May 20, 2004) Pages 2129-2139

Mahon, F. X., Deininger, M. W. N., Schultheis, B., Chabrol, J., Reiffers, J., Goldman, J. M., Melo, J. V. Selection and Characterization of BCR-ABL Positive Cell Lines with Differential Sensitivity to the Tyrosine Kinase Inhibitor STI571: Diverse Mechanisms of Resistance. Blood, Volume 96 (Aug. 1, 2000) Pages 1070-1079

Mansky, L. M., Temin, H. M. Lower In Vivo Mutation Rate of Human Immunodeficiency Virus Type 1 than that Predicted from the Fidelity of Purified Reverse Transcriptase. Journal of Virology, Volume 69 (August 1995) Pages 5087-5094

Marshall, J. R., Walker, J. Experimental Study of Some Potentially Tautomeric 2- and 4(6)-Substituted Pyrimidines. Journal of the Chemical Society, (1951) Pages 1004-1017.

Marx, J. Why a New Cancer Drug Works Well in Some Patients. Science, Volume 304 (Apr. 30, 2004) Pages 658-659

Melo, J. V., Myint, H., Galton, D. A., Goldman, J. M. P190BCR-ABL chronic myeloid leukaemia: the missing link with chronic myelomonocytic leukaemia? Leukemia, Volume 8 (January 1994) Pages 208-211

Nair, M. D., Mehta, S. R. Syntheses and Reactions of Condensed Isoquinolines*-Imidazo, Pyrimido, Triazolo and Tetrazolo Isoquinolines. Indian Journal of Chemistry, Volume 5 (September 1967) Pages 403-408

Noble, M. E. M., Endicott, J. A., Johnson, L. N. Protein Kinase Inhibitors: Insights into Drug Design from Structure. Science, Volume 303 (Mar. 19, 2004) Pages 1800-1805

O'Hare, T., Pollock, R., Stoffregen, E. P., Keats, J. A., Abdullah, O. M., Moseson, E. M., Rivera, V. M., Tang, H., Metcalf, C. A. 3rd, Bohacek, R. S., Wang, Y., Sundaramoorthi, R., Shakespeare, W. C., Dalgarno, D., Clackson, T., Sawyer, T. K., Deininger, M. W., Druker, B. J. Inhibition of wild-type and mutant Bcr-Abl by AP23464, a potent ATP-based oncogenic protein kinase inhibitor: implications for CML. Blood, Volume 104 (Oct. 15, 2004) Pages 2532-2539

Paez, J. G., Jänne, P. A., Lee, J. C., Tracy, S., Greulich, H., Gabriel, S., Herman, P., Kaye, F. J., Lindeman, N., Boggon, T. J., Naoki, K., Sasaki, H., Fujii, Y., Eck, M. J., Sellers, W. R., Johnson, B. E., Meyerson, M. EGFR Mutations in Lung Cancer: Correlation with Clinical Response to Gefitinib Therapy. Sciencexpress (Apr. 29, 2004) Pages 1-4

Ravandi, F., Cortes, J., Albitar, M., Arlinghaus, R., Qiang, Guo J., Talpaz, M., Kantarjian, H. M. Chronic myelogenous leukaemia with p185(BCR/ABL) expression: characteristics and clinical significance. British Journal of Haematology, Volume 107 (December 1999) Pages 581-586

Sambrook, J., Fritsch, E. F., Maniatis, T. Molecular Cloning: A Laboratory Manual, $2^{nd}$ ed., Cold Spring Harbor Laboratory Press; New York, 1989

Sambrook and Russell, Molecular Cloning: A Laboratory Manual. Cold Spring Harbor Laboratory Press, New York, 2001, Volumes 1-3

Sawyers, C. L., Gorre, M. E., Shah, N. P., Nicoll, J. Mutations in the Bcr-Abl Tyrosine Kinase Associated with Resistance to STI-571. WO2002US0018729 (US2002000171889)

Sawyers, C. L. M. D. Chronic Myeloid Leukemia. The New England Journal of Medicine, Volume 340 (Apr. 29, 1999) Pages 1330-1340

Schindler, T., Bornmann, W., Pellicena, P., Miller, W. T., Clarkson, B., Kuriyan, J. Structural Mechanism for STI-571 Inhibition of Abelson Tyrosine Kinase. Science, Volume 289 (Sep. 15, 2000) Pages 1938-1942

Senechal, K., Halpern, J., Sawyers, C. L. The CRKL Adaptor Protein Transforms Fibroblasts and Functions in Transformation by the BCR-ABL Oncogene. The Journal of Biological Chemistry, Volume 271 (Sep. 20, 1996) Pages 23255-23261

Senechal, K., Heaney, C., Druker, B., Sawyers, C. L. Structural Requirements for Function of the Crkl Adapter Protein in Fibroblasts and Hematopoietic Cells. Molecular and Cellular Biology, Volume 18 (September 1998) Pages 5082-5090

Shah, N. P., Tran, C., Lee, F. Y., Chen, P., Norris, D., Sawyers, C. L. Overriding Imatinib Resistance with a Novel ABL Kinase Inhibitor. Science, Volume 305 (Jul. 16, 2004) Pages 399-401

Shearer, B. G., Lee, S., Franzmann, K. W., White, H. A. R., Sanders, D. C. J., Kiff, R. J., Garvey, E. P., Furfine, E. S. Conformationally Restricted Arginine Analogues as Inhibitors of Human Nitric Oxide Synthase. Bioorganic and Medicinal Chemistry Letters, Volume 7 (Jul. 8, 1997) Pages 1763-1768

Tipping, A. J., Baluch, S., Barnes, D. J., Veach, D. R., Clarkson, B. M., Bornmann, W. G., Mahon, F. X., Goldman, J. M., Melo, J. V. Efficacy of dual-specific Bcr-Abl and Src-family kinase inhibitors in cells sensitive and resistant to imatinib mesylate. Leukemia, Volume 18 (August 2004) Pages 1352-1356

Von Bubnoff, N., Schneller, F., Peschel, C., Duyster, J. BCR-ABL Gene Mutations in Relation to Clinical Resistance of Philadelphia-Chromosome-Positive Leukemia to STI571: A Prospective Study. The Lancet, Volume 359 (Feb. 9, 2002) Pages 487-491

Von Bubnoff, N., Veach, D. R., Van Der Kuip, H., Aulitzky, W. E., Sanger, J., Seipel, P., Bornmann, W. G., Peschel, C., Clarkson, B., Duyster, J. A cell-based screen for resistance of Bcr-Abl positive leukemia identifies the mutation pattern for PD166326, an alternative Abl kinase inhibitor. Blood, Volume 105 (Feb. 15, 2005) Pages 1652-1659

Wakai, T., Kanda, T., Hirota, S., Ohashi, A., Shirai, Y. Hatakeyama, K. Late Resistance to Imatinib Therapy in a Metastatic Gastrointestinal Stromal Tumour is Associated With a Second KIT Mutation. British Journal of Cancer, Volume 90 (Jun. 1, 2004) Pages 2059-2061

Weigel, U., Meyer, M., Sebald, W. Mutant Proteins of Human Interleukin 2: Renaturation Yield, Proliferative Activity and Receptor Binding. European Journal of Biochemistry, Volume 180 (Mar. 15, 1989) Pages 295-300.

Weisberg, E., Catley, L., Kujawa, J., Atadja, P., Remiszewski, S., Fuerst, P., Cavazza, C., Anderson, K., Griffin, J. D. Histone deacetylase inhibitor NVP-LAQ824 has significant activity against myeloid leukemia cells in vitro and in vivo. Leukemia, Volume 18 (December 2004) Pages 1951-1963

Weisberg, E., Griffin, J. D. Mechanism of Resistance to the ABL Tyrosine Kinase Inhibitor STI 571 in BCR/ABL-Transformed Hematopoietic Cell Lines. Blood, Volume 95 (Jun. 1, 2000) Pages 3498-3505

Weisberg, E., Manley, P. W., Breitenstein, W., Bruggen, J., Cowan-Jacob, S. W., Ray, A., Huntly, B., Fabbro, D., Fendrich, G., Hall-Meyers, E., Kung, A. L., Mestan, J., Daley, G. Q., Callahan, L., Catley, L., Cavazza, C., Azam, M., Neuberg, D., Wright, R. D., Gilliland, D. G., Griffin, J. D. Characterization of AMN107, a selective inhibitor of native and mutant Bcr-Abl. Cancer Cell, Volume 7 (February 2005) Pages 129-141

White, M. F., Livingston, J. M., Backer, Lauris, V., Dull, T. J., Ullrich, A., Kahn, C. R. Mutation of the Insulin Receptor at Tyrosine 960 Inhibits Signal Transmission but Does Not Affect Its Tyrosine Kinase Activity. Cell, Volume 54 (Aug. 26, 1988) Pages 641-649

Wu, M. T., MacCoss, M., Ikeler, T. J., Hirshfield, J., Arison, B. H., Tolman, R. L. Annelated Piperazinyl-7,8-dihydro-6H-thiopyrano[3,2-d]pyrimidines. Journal of Heterocyclic Chemistry, Volume 27 (1990) Pages 1559-1563

What is claimed is:

1. A compound for use in modulating a theramutein in a subject, wherein the theramutein is a protein which harbors a mutation in its corresponding endogenous protein, wherein said mutation is associated with the development of clinical resistance in a subject to a drug that modulates the corresponding non-mutated protein, the compound being selected using a method comprising:

a) incubating a first cell which expresses a theramutein at a substantially constant level with the compound, the theramutein being capable of producing a detectable phenoresponse of the first cell;

b) incubating a second cell which expresses a prototheramutein corresponding to the theramutein at a substantially constant level with a known modulator of the prototheramutein, the prototheramutein being capable of producing the phenoresponse in the second cell;

c) comparing the phenoresponse of the second cell to the known modulator of the prototheramutein to the phenoresponse of the first cell to the compound; and d) determining that the compound is a modulator of the theramutein when the phenoresponse of the first cell is modulated to at least the same degree as the phenoresponse of the second cell is modulated by the known modulator of the prototheramutein.

2. The compound of claim 1, wherein the phenoresponse of the first cell expressing the theramutein to the compound is greater than the phenoresponse of the second cell expressing the prototheramutein to the known modulator of the prototheramutein.

3. The compound of claim 1, wherein either the theramutein or its corresponding prototheramutein is a component of a signal transduction cascade.

4. The compound of claim 1, wherein either the theramutein or its corresponding prototheramutein is a protein kinase.

5. The compound of claim 1, wherein the phenoresponse of the first cell comprises a growth characteristic of the first cell and the phenoresponse of the second cell comprises the growth characteristic of the second cell.

6. The compound of claim 1, wherein the phenoresponse of the first cell comprises a transformation state of the first cell and the phenoresponse of the second cell comprises the transformation state of the second cell.

7. The compound of claim 1, wherein the phenoresponse of the first cell comprises a differentiation state of the first cell and the phenoresponse of the second cell comprises the differentiation state of the second cell.

8. The compound of claim 1, wherein the phenoresponse of the first cell comprises a phosphorylation state of a second protein in the first cell that is not the theramutein and the phenoresponse of the second cell comprises the phosphorylation state of a second protein in the second cell that is not the prototheramutein.

9. The compound of claim 1, wherein the phenoresponse of the first cell comprises a change of an ion flux across a membrane of the first cell and the phenoresponse of the second cell comprises a change of the ion flux across the membrane of the second cell.

10. The compound of claim 1, wherein the phenoresponse of the first cell comprises a change of pH within the first cell and the phenoresponse of the second cell comprises a change of pH within the second cell.

11. The compound of claim 1, wherein the phenoresponse of the first cell comprises a change in concentration of an intracellular chemical species in the first cell and the phenoresponse of the second cell comprises a change in concentration of the intracellular chemical species in the second cell.

12. The compound of claim 1, wherein the phenoresponse of the first cell comprises modulation of genetic expression of the theramutein within the first cell and the phenoresponse of the second cell comprises modulation of the genetic expression of the prototheramutein in the second cell.

13. The compound of claim 1, wherein the prototheramutein comprises a $p210^{BCR-ABL}$ oncoprotein.

14. The compound of claim 1, wherein the theramutein comprises a p210$^{BCR-ABL}$ oncoprotein that comprises a threonine (T) to an isoleucine (I) mutation at position 315.

15. The compound of claim 1, wherein the prototheramutein comprises a c-kit oncogene product, an Epidermal Growth Factor Receptor, a Platelet Derived Growth α Receptor, or a Platelet Derived Growth β Receptor.

16. The compound of claim 1, wherein the theramutein comprises a mutation in the c-kit oncogene product, a mutation in the Epidermal Growth Factor Receptor, a mutation in the Platelet Derived Growth α Receptor, or a mutation in the Platelet Derived Growth β Receptor.

* * * * *